US012686011B2

(12) United States Patent
Lee

(10) Patent No.: US 12,686,011 B2
(45) Date of Patent: Jul. 21, 2026

(54) SYSTEM AND METHOD FOR IMPROVING THE CORN WET MILL AND DRY MILL PROCESS

(71) Applicant: Lee Tech LLC, Los Gatos, CA (US)

(72) Inventor: Chie Ying Lee, Los Gatos, CA (US)

(73) Assignee: Lee Tech LLC, Los Gatos, CA (US)

( * ) Notice: Subject to any disclaimer, the term of this patent is extended or adjusted under 35 U.S.C. 154(b) by 477 days.

(21) Appl. No.: 18/133,193

(22) Filed: Apr. 11, 2023

(65) Prior Publication Data

US 2023/0285979 A1     Sep. 14, 2023

Related U.S. Application Data

(63) Continuation-in-part of application No. 17/581,434, filed on Jan. 21, 2022, now Pat. No. 11,623,966.

(60) Provisional application No. 63/140,342, filed on Jan. 22, 2021.

(51) Int. Cl.
| | |
|---|---|
| *B02B 5/00* | (2006.01) |
| *B02B 5/02* | (2006.01) |
| *C08B 30/04* | (2006.01) |
| *C12P 7/06* | (2006.01) |
| *C12P 7/16* | (2006.01) |

(52) U.S. Cl.
CPC .............. *B02B 5/02* (2013.01); *C08B 30/044* (2013.01); *C12P 7/06* (2013.01); *C12P 7/16* (2013.01)

(58) Field of Classification Search
None
See application file for complete search history.

(56) References Cited

U.S. PATENT DOCUMENTS

| | | |
|---|---|---|
| 1,942,943 A | 1/1934 | Schnabel |
| 2,190,176 A | 2/1940 | Smith |
| 2,313,275 A | 3/1943 | Schopmeyer et al. |
| | (Continued) | |

FOREIGN PATENT DOCUMENTS

| | | |
|---|---|---|
| AU | 2013200519 B2 | 2/2013 |
| CN | 1883299 A | 12/2006 |
| | (Continued) | |

OTHER PUBLICATIONS

CN-204138576-U—English translation (Year: 2015).*

(Continued)

*Primary Examiner* — Stefanie J Cohen
(74) *Attorney, Agent, or Firm* — Haverstock & Owens, A Law Corporation

(57) ABSTRACT

This novel corn milling process includes a continuous steeping step, early separation of easy-to-access starch (e.g., starch in the floury endosperm part of a corn kernel), fine milling to secure germ protein without the use of solvents or heat, and performing a phase separation to collect the product of fermentation. The continuous steeping process uses a continuous steeping tank. The steeping liquid, which includes probiotics, flows in from the bottom of the tank in a countercurrent flow. Other features include efficiently producing high purity starch or sugar using the starch in the floury endosperm of the corn kernel, producing alcohols such as ethanol and butanol that can be used as sustainable aviation fuel or feedstock for sustainable aviation fuel, and producing a high protein animal feed product that includes yeast and germ protein without using toxic solvents.

19 Claims, 29 Drawing Sheets

(56) References Cited

U.S. PATENT DOCUMENTS

| | | | |
|---|---|---|---|
| 2,600,903 A | 6/1952 | Miller | |
| 2,967,107 A | 1/1961 | Geiger et al. | |
| 3,054,676 A | 9/1962 | Lauhoff et al. | |
| 3,058,887 A | 10/1962 | Platt et al. | |
| 3,753,723 A | 8/1973 | Henderson | |
| 3,786,078 A | 1/1974 | Smith et al. | |
| 3,827,423 A | 8/1974 | Bolitho | |
| 3,973,043 A | 8/1976 | Lynn | |
| 3,975,546 A | 8/1976 | Stahmann | |
| 4,042,172 A | 8/1977 | Norzdrovsky | |
| 4,106,487 A * | 8/1978 | Randall | C08B 30/02 |
| | | | 127/23 |
| 4,130,553 A | 12/1978 | Batley, Jr. | |
| 4,171,383 A | 10/1979 | Chwalek et al. | |
| 4,255,518 A | 3/1981 | Muller et al. | |
| 4,313,061 A | 1/1982 | Thomas | |
| 4,333,871 A | 6/1982 | De Jong | |
| 4,341,713 A | 7/1982 | Stolp et al. | |
| 4,361,651 A | 11/1982 | Keim | |
| 4,396,161 A | 8/1983 | Roukolainen et al. | |
| 4,517,022 A | 5/1985 | Harvey | |
| 4,635,864 A | 1/1987 | Peterson et al. | |
| 4,772,481 A | 9/1988 | Rohwer | |
| 4,835,100 A | 5/1989 | Dixon | |
| 4,857,325 A | 8/1989 | Albeck | |
| 4,978,618 A | 12/1990 | Kalina | |
| 5,177,008 A | 1/1993 | Kampen | |
| 5,244,159 A | 9/1993 | Newman | |
| 5,248,099 A | 9/1993 | Lahner et al. | |
| 5,294,434 A | 3/1994 | King | |
| 5,364,335 A | 11/1994 | Franzen et al. | |
| 5,475,099 A | 12/1995 | Knauf | |
| 5,516,974 A | 5/1996 | Sasae | |
| 5,994,113 A | 11/1999 | Kauppinen et al. | |
| 6,080,401 A | 6/2000 | Reddy | |
| 6,190,462 B1 | 2/2001 | Markland et al. | |
| 6,254,914 B1 | 7/2001 | Singh et al. | |
| 6,274,358 B1 | 8/2001 | Holtz et al. | |
| 6,569,653 B1 | 5/2003 | Alard | |
| 6,899,910 B2 | 5/2005 | Johnston et al. | |
| 7,297,236 B1 | 11/2007 | Vander Griend | |
| 7,563,469 B1 | 7/2009 | Navarro et al. | |
| 7,687,648 B2 | 3/2010 | Smallridge et al. | |
| 7,700,094 B1 | 4/2010 | Nsereko | |
| 7,858,140 B2 | 12/2010 | Paustian et al. | |
| 9,012,191 B2 | 4/2015 | Lee | |
| 9,352,326 B2 | 5/2016 | Lee | |
| 9,388,475 B2 | 7/2016 | Lee | |
| 9,695,381 B2 | 7/2017 | Lee | |
| 9,777,303 B2 | 10/2017 | Jakel et al. | |
| 10,190,086 B2 | 1/2019 | Narendranath | |
| 11,166,478 B2 | 11/2021 | Lee | |
| 11,427,839 B2 | 8/2022 | Lee | |
| 11,680,278 B2 | 6/2023 | Lee | |
| 12,065,513 B2 | 8/2024 | Lee | |
| 12,084,707 B2 | 9/2024 | Lee | |
| 12,351,852 B2 | 7/2025 | Lee | |
| 12,365,744 B2 | 7/2025 | Lee | |
| 2001/0014360 A1 | 8/2001 | Paluch | |
| 2002/0122944 A1 | 9/2002 | Ogle et al. | |
| 2003/0180415 A1 | 9/2003 | Stiefel | |
| 2004/0009160 A1 | 1/2004 | Villamar | |
| 2004/0071757 A1 | 4/2004 | Rolf | |
| 2004/0087808 A1 | 5/2004 | Prevost et al. | |
| 2004/0187863 A1 | 9/2004 | Langhauser | |
| 2004/0258782 A1 | 12/2004 | Hoffman et al. | |
| 2005/0009133 A1 | 1/2005 | Johnston et al. | |
| 2005/0028810 A1 | 2/2005 | Lee | |
| 2005/0100996 A1 | 5/2005 | Lantero, Jr. et al. | |
| 2005/0170067 A1 | 8/2005 | Shao et al. | |
| 2005/0249837 A1 | 11/2005 | Massimio et al. | |
| 2005/0281792 A1 | 12/2005 | Short | |
| 2006/0127453 A1 | 6/2006 | Harel | |
| 2006/0154353 A1 | 7/2006 | Duan | |
| 2006/0292677 A1 | 12/2006 | Ostrander | |
| 2007/0066476 A1 | 3/2007 | Ullmann | |
| 2007/0148318 A1 | 6/2007 | Rubio et al. | |
| 2007/0184159 A1 | 8/2007 | Shima et al. | |
| 2007/0184541 A1 | 8/2007 | Karl et al. | |
| 2007/0210007 A1 | 9/2007 | Scheimann et al. | |
| 2007/0231311 A1 | 10/2007 | Kroening | |
| 2008/0095881 A1 | 4/2008 | Ber | |
| 2008/0210541 A1 | 9/2008 | Wenger et al. | |
| 2008/0279983 A1 | 11/2008 | Lohrmann et al. | |
| 2009/0029432 A1 | 1/2009 | Abbas et al. | |
| 2009/0047382 A1 | 2/2009 | Cates | |
| 2009/0061490 A1 | 3/2009 | Edwards et al. | |
| 2009/0093027 A1 | 4/2009 | Balan et al. | |
| 2009/0181153 A1 | 7/2009 | Bendorf et al. | |
| 2009/0227004 A1 | 9/2009 | Dale | |
| 2010/0028484 A1 | 2/2010 | Kriesler et al. | |
| 2010/0082312 A1 | 4/2010 | Macharia | |
| 2010/0093860 A1 | 4/2010 | Boon et al. | |
| 2010/0120128 A1 | 5/2010 | Liang | |
| 2010/0159547 A1 | 6/2010 | Falcounbridge | |
| 2010/0159552 A1 | 6/2010 | Benson et al. | |
| 2010/0196994 A1 | 8/2010 | Van Leeuwen et al. | |
| 2010/0260918 A1 | 10/2010 | Wang | |
| 2010/0324274 A1 | 12/2010 | DeFrees | |
| 2011/0086149 A1 | 4/2011 | Bootsma | |
| 2011/0100359 A1 | 5/2011 | North | |
| 2011/0106277 A1 | 5/2011 | Sayyar-Rodsari | |
| 2011/0123657 A1 | 5/2011 | Vandenbroucke et al. | |
| 2011/0150853 A1 | 6/2011 | Mann et al. | |
| 2011/0177560 A1 | 7/2011 | Galvez, III et al. | |
| 2011/0223307 A1 | 9/2011 | Bertoldo de Barros et al. | |
| 2011/0250310 A1 | 10/2011 | Mateus | |
| 2011/0250312 A1 | 10/2011 | Lewis | |
| 2011/0269185 A1 | 11/2011 | David | |
| 2011/0283602 A1 | 11/2011 | Gallop et al. | |
| 2011/0315541 A1 | 12/2011 | Xu | |
| 2012/0048716 A1 | 3/2012 | Sonnek | |
| 2012/0077232 A1 | 3/2012 | Budaraju et al. | |
| 2012/0077244 A1 | 3/2012 | Budaraju et al. | |
| 2012/0107454 A1 | 5/2012 | Hoffman et al. | |
| 2012/0125859 A1 | 5/2012 | Collins | |
| 2012/0168387 A1 | 7/2012 | Tran et al. | |
| 2012/0183643 A1 | 7/2012 | Dale | |
| 2012/0199531 A1 | 8/2012 | Winsness | |
| 2012/0244590 A1 | 9/2012 | Lee | |
| 2012/0245123 A1 | 9/2012 | Lopez Pedrosa et al. | |
| 2012/0252065 A1 | 10/2012 | Rozenszain et al. | |
| 2012/0270275 A1 | 10/2012 | Fenton et al. | |
| 2013/0121891 A1 | 5/2013 | Dieker | |
| 2013/0130343 A1 | 5/2013 | Purtle et al. | |
| 2013/0206342 A1 | 8/2013 | Dahmes | |
| 2013/0224333 A1 | 8/2013 | Nanjundaswamy et al. | |
| 2013/0236936 A1 | 9/2013 | Lee | |
| 2013/0288376 A1 | 10/2013 | Lee | |
| 2013/0316041 A1 | 11/2013 | Maranz | |
| 2013/0337517 A1 | 12/2013 | Razavi-Shirazi | |
| 2013/0344045 A1 | 12/2013 | Faure | |
| 2014/0004571 A1 | 1/2014 | Garrett | |
| 2014/0053829 A1 | 2/2014 | Lee | |
| 2014/0102950 A1 | 4/2014 | Bethke | |
| 2014/0186868 A1 | 7/2014 | Siegert | |
| 2014/0206055 A1 | 7/2014 | Ramos | |
| 2014/0242251 A1 | 8/2014 | Bootsma | |
| 2014/0273140 A1 | 9/2014 | Langhouser | |
| 2014/0319066 A1 | 10/2014 | LoCascio | |
| 2014/0343254 A1 | 11/2014 | Gerardi | |
| 2015/0152372 A1 | 6/2015 | Kohl | |
| 2015/0176034 A1 | 6/2015 | Ramos | |
| 2015/0223493 A1 | 8/2015 | Lee | |
| 2015/0231535 A1 * | 8/2015 | Lee | B01D 29/6476 |
| | | | 210/457 |
| 2015/0240266 A1 | 8/2015 | Lee | |
| 2015/0307822 A1 | 10/2015 | Rossell et al. | |
| 2016/0060658 A1 | 3/2016 | Lee | |
| 2016/0222135 A1 * | 8/2016 | Lee | C12P 7/16 |
| 2016/0374364 A1 | 12/2016 | Lee | |
| 2017/0022529 A1 | 1/2017 | Jakel et al. | |
| 2017/0058300 A1 | 3/2017 | Aurandt | |
| 2017/0166834 A1 | 6/2017 | Jakel | |

(56)                    References Cited

U.S. PATENT DOCUMENTS

| | | | |
|---|---|---|---|
| 2017/0166835 A1 | 6/2017 | Jakel | |
| 2018/0044620 A1 | 2/2018 | Bootsma | |
| 2018/0225669 A1 | 8/2018 | Brotherson | |
| 2018/0343891 A1 | 12/2018 | Lee | |
| 2019/0017080 A1 | 1/2019 | Bootsma | |
| 2019/0119711 A1 | 4/2019 | Lee | |
| 2019/0211365 A1 | 7/2019 | Jakel | |
| 2019/0241834 A1 | 8/2019 | Lee | |
| 2021/0024964 A1 | 1/2021 | Lee | |
| 2021/0059277 A1 | 3/2021 | Lee | |
| 2021/0113966 A1 | 4/2021 | Benson et al. | |
| 2022/0022492 A1 | 1/2022 | Lee | |
| 2022/0205006 A1 | 6/2022 | Cao et al. | |
| 2022/0235150 A1 | 7/2022 | Lee | |
| 2022/0348969 A1 | 11/2022 | Lee | |
| 2023/0272437 A1 | 8/2023 | Lee | |
| 2023/0277956 A1 | 9/2023 | Lee | |
| 2023/0285979 A1 | 9/2023 | Lee | |
| 2023/0406963 A1 | 12/2023 | Lee | |
| 2024/0417761 A1 | 12/2024 | Lee | |
| 2025/0043030 A1 | 2/2025 | Lee | |
| 2025/0320530 A1 | 10/2025 | Lee | |

FOREIGN PATENT DOCUMENTS

| | | | |
|---|---|---|---|
| CN | 1966706 A | | 5/2007 |
| CN | 101080483 A | | 11/2007 |
| CN | 101453884 A | | 8/2009 |
| CN | 101621935 A | | 1/2010 |
| CN | 101795578 A | | 8/2010 |
| CN | 102448321 A | | 5/2012 |
| CN | 204138576 U | * | 2/2015 |
| CN | 104703957 A | | 6/2015 |
| CN | 106615685 A | | 5/2017 |
| CN | 107034240 A | | 8/2017 |
| CN | 107208116 A | | 9/2017 |
| CN | 107208166 A | | 9/2017 |
| DE | 4239342 A1 | | 5/1994 |
| EP | 0772978 B1 | | 11/1991 |
| EP | 722669 B1 | | 5/2002 |
| GB | 511525 A | | 8/1939 |
| GB | 852995 A | | 11/1960 |
| WO | 01/14595 A2 | | 3/2001 |
| WO | 2006104504 A2 | | 10/2006 |
| WO | 2012075481 A1 | | 6/2012 |
| WO | 2012145230 A1 | | 10/2012 |
| WO | 2012160191 A2 | | 11/2012 |
| WO | 2012166290 A1 | | 12/2012 |
| WO | 2013034747 A1 | | 3/2013 |
| WO | 2014031700 A2 | | 2/2014 |
| WO | 20140127852 A2 | | 8/2014 |
| WO | 2015066669 A1 | | 5/2015 |
| WO | 2016033548 A1 | | 3/2016 |
| WO | 2016123258 A1 | | 8/2016 |
| WO | 2021086865 A1 | | 5/2021 |
| WO | 2022159719 A1 | | 7/2022 |

OTHER PUBLICATIONS

The Re-Examination Notice, mailed on Jan. 14, 2026, Chinese Patent Application No. 202080073152.8, 3 pages.
The Office Action dated Jul. 25, 2025 from Brazilian Patent Application No. BR112022008178-2.
The Office Action dated Jul. 27, 2025 from Chinese Patent Application No. 202380047671.0.
The Notification of Transmittal of International Search Report and the Written Opinion of the International Searching Authority, or the Declaration dated Jul. 19, 2023 from PCT Patent Application No. PCT/US23/14159.
The Notification Concerning Transmittal of International Preliminary report on Patentability dated Sep. 12, 2024 for PCT Application No. PCT/US2023/014159.

The International Preliminary report on Patentability dated Dec. 26, 2024 for PCT Application No. PCT/US2023/025624.
The Second Office Action dated Mar. 25, 2023 from Chinese Patent Application No. 202080073152.8.
The Notice of Rejection Decision dated May 27, 2023 from Chinese Patent Application No. 202080073152.8.
The Rejection Decision dated Mar. 29, 2024 for Chinese Patent Application No. 202080070146.7.
The Notice of Allowance dated Apr. 4, 2024 for Chinese Patent Application No. 202280017556.4.
The Examiner's Report dated Dec. 11, 2025, from Canadian Application No. 3,159,554.
The Notification of Transmittal of International Search Report and the Written Opinion of the International Searching Authority, or the Declaration dated Oct. 11, 2023, from PCT Patent Application No. PCT/US23/25624.
The second Office Action, dated Aug. 1, 2023, from Chinese Patent Application No. 202080070146.7.
Google Search Result (Retrieved on May 22, 2024) (Year: 2024).
The Rejection Decision mailed on Jan. 4, 2026, from Chinese Patent Application No. 202380047671.0, pages.
2nd Office Action from Chinese Patent Application No. 202380047671.0, mailed on Nov. 2, 2025.
International Search Report and Written Opinion from PCT Application No. PCT/US15/47577.
"Organic" organic.org; published Dec. 25, 2012, accessed on Mar. 3, 2017, available at htt://web.archive.org/web/20121225201858/http://www.organic.org/home /faq.
Alfagreen supreme: available at:https://web.archive.org/web/20121207050409 02/thttp://www.alfagreensupreme.com.ourproducts:html:published Jul. 12, 2012, accessed on Mar. 6, 2017.
Egg, whole, raw, fresh form composition of Foods Raw, Processed, Prepared , USDA National Nutrient Database for Standard Reference, Release 22, Sep. 2009,; available at :http:// www.ars.usda.gov/northweast-area/beltsville-human-nutrition-research-center/nutrient-data-laboratory/docs/sr22-download-files/: access on Oct. 17, 2017.
Swiss chard, What's New and Beneficial About Swiss Chard: The World's Healthiest Foods; available at : http://web.archive.org/web/20130117060212/http://www.whfoods.com/genpage.php?tname=foodspice&dbid=16;published on Jan. 17, 2013: accessed on 10/19/20174.
Singh et al., "Effect of Corn Oil on Thin Stillage Evaporators", Cereal Chemistry, pp. 846-849, 1999.
Blog, Birdworms & Buttermilk, Extracting Chlorophyll from Leafy Greens; available at: http://birdworms.com/2010/06/26/extractingchlorophyllfromleafygreens/; accessed on Oct. 6, 2016; published on Jun. 2010.
Timbekova et al., Chemistry and Biological Activity of Triterpenoid glycosides from Medicago.
Gonzalez-Martin, Use of NIRS technology with a remote reflectance fibre-optic probe for predicting mineral composition(Ca, K, P, Fe, Mn, Na, Zn), protein and moisture in alfalfa; Anal Bioanal Chem (2007) 387:2199-2205.
What Are Enzymes?: published Mar. 7, 2013; available at : https;//web.archive.org./webs/20130307025120/hrrp://www.enzyme-facts.com/enzymes.html; accessed on Aug. 11, 2017.
"Hydrocarbon." In the Columbia Encyclopedia, by Paul Lagasse, and Columbia University. 7th ed. Columbia University Press, 2017. http://search.credoreference.com/content/entry/columency/hydrocarbon/0?institutionId=743.
"Starch." In the American Heritage (R) Dictionary of the English Language, edited by the Editors of the American Heritage Dictionaries. 5th ed. Houghton Mifflin, 2011. http://search.credoreference.com/content/entry/hmdictenglang/starch/0?institutionId=743.
Kung, A review on silage additives and enzymes, Proceeding of the 59th Minneapolis Nutrition Conference, Sep. 1998; p. 121-135.
Heist, A Guide to Successful Yeast Propagation, Ethanol Producer Magazine, 2008.
Dotty 1, New natural medical antibiotic; Chlorophyll & Spinach, available at http://www.acne.org/messageboard/topic/254668-new-natural-medical-antibiotic-chlorophyllspinach/; published Nov. 30, 2009; accessed on Jul. 3, 2017.

(56)         References Cited

OTHER PUBLICATIONS

Spinach, vol. 1, No. 14, University of the District of Columbia, Center for Nutrition, Diet and Health, published Jan. 23, 2014, accessed on Jul. 30, 2017, available at : https://web.archive.org/web/20140123214335/https://www.udc.edu/docs/causes/online/Spinach%2014.pdf.

Shahina Z. et al., "Variation of Protease Production by the Bacteria (Bacillus Fastidiosus) and the Fungus (Aspergillus Funiculosus)", Journal of Microbiology Research [online], 2013 [retrieved on Oct. 17, 2016], vol. 3, issue 4, retrieved from the Internet: <DIO: 10.5923//j.microbiology.2013030402>, pp. 135-142, see entire documents, especially p. 135.

International Search Report from PCT/US16/38436 dated Oct. 31, 2016.

The International Search Report dated Dec. 18, 2018, for International Application No. PCT/ US18/56340.

The Office Action for Canadian Patent Application No. 2,951,715 dated Jul. 9, 2019.

The Office Action for Brazilian Patent Application No. BR112015003793-3 dated Jul. 23, 2019.

The Office Action dated May 9, 2019 for Canadian Patent Application No. 2,882,173.

The Brazilian Office Action for Patent Application No. BR112017016172-9 Dated: 26, 2019.

The Brazilian Office Action for Patent Application No. BR112017027884-7 Dated: Jan. 2, 2020.

The International Preliminary Report form PCT Application No. PCT/US2018/056340, dated Apr. 30, 2020.

The Chinese Office Action dated Jun. 3, 2020 for Chinese Patent Application No. 201680007372.4.

GESE Success, Letters Educational , UK, 2006, p. 19 ( Year : 2006).

The Office Action for the Argentina Patent Application No. 20160101901 Dated: Aug. 19, 2020.

The Brazilian Office Action dated Aug. 8, 2020 for Brazilian Patent Application No. BR112017004017-4.

The Office Action from the Canadian Patent Application No. 2,951,715 dated Aug. 28, 2020.

Labedz et al., Precise Mass Determination of Single Cell With Cantilever-Based Microbiosensor System, PLOS One, http//:doi.otg/10.137/journal.pone.018838, Nov. 21, 2017,pp. 1-14.

The International Search Report and Written Opinion for the Application No. PCT/US20/55174 dated Mar. 18, 2021.

Xu et al., Continuous ethanol production using self-flocculating yeast in a cascade of fermentors' Enzyme and Microbial Technology 37 (2005) 634-640, entire document esp p. 635-636.

https://en.wikipedia.org/windex.php?title=Clean-in-place&oldid=889731953'Clean-inplace'Mar. 27, 2019, entire document esp p. 2.

Best way to keep dog food and treats fresh—Vacuum seal!, vacmasterfresh.com, Aug. 26, 2015 [online], [retrieved Feb. 11, 2021]. Retrieved from the Internet<https://www.vacmasterfresh.com/fresh-bites-blog/ best-way-to-keep-dog-food-and -treats-fresh-vacuum-seal/>(Year:2015).

The Pelleting Process, California Pellet Mill Co., May 17, 2017[online], [retrieved Feb. 11, 2021]. Retrieved from the Internet<https://www.cpm.net/downloads/ Animal%20Feed%20Pelleting.pdf>(Year:2017).

Vibrating Fluid Bed Dryers, Carrier Vibrating, May 12, 2017[online], [retrieved Feb. 17, 2021].Retrieved from the Internet<https://www.carriervibrating.com/equipment/dryers/vibrating/>(2017).

Imran M. et. al., Role of Enzymes in Animal Nutrition: A Review, PSM Vet. Res., 01(2)(2016): 38-45. (Year: 2016).

How many different chemical reactions ca a single enzyme catalyze?, Truong-Son N, Jan. 3, 2016 [online], [retrieved Mar. 4, 2021]. Retrieved from the Internet<https://socratic.org/questions/jo-many-different-chemical-reactions-can-a single-enzyme-catalyze>(Year:2016).

The International Search Report and Written Opinion for the International Application No. PCT/US2020/057558 dated Jan. 27, 2021.

The Office Action for the Chinese Application No. 201680007372.4 dated Feb. 22, 2021.

The Office Action for the Brazilian Patent Application No. BR 11 2015 003793-3 Feb. 2, 2021.

The Office Action dated Dec. 4, 2020, for Chinese Patent Application No. 201680003607.2.

The International Preliminary Report dated May 12, 2022 for the International Application No. PCT/US2020/057558.

International Search Report and Written Opinion of the International Search Authority dated Apr. 11, 2022 for International Application No. PCT/US2022/13332, 16 pages.

International Preliminary Report on Patentability dated Apr. 21, 2022 for International Application No. PCT/US2020/055174, 9 pages.

The First Office Action dated Dec. 26, 2022 from Chinese Patent Application No. 202080073152.8.

The First Office Action dated Jan. 10, 2023 from Chinese Patent Application No. 202080073152.8.

The International Preliminary report on Patentability dated Oct. 23, 2025 for International Application No. PCT/US2023/018136.

The Office Action dated Jan. 26, 2024 for Chinese Patent Application No. 202280017556.4.

International Search Report mailed Aug. 23, 2023, International Application No. PCT/US2023/018136, 20 pages.

* cited by examiner

500

1400

Corn Kernel

1410 Hull

1420 Floury Endosperm

1430 Horny Endosperm (cells filled with starch granules in a protein matrix)

1440 Germ

1450 Tip Cap

Cross section 1:
Paddle and chamber design move corn inwards

Cross section 2:
Paddle and chamber design move corn outwards

SYSTEM AND METHOD FOR IMPROVING THE CORN WET MILL AND DRY MILL PROCESS

CROSS-REFERENCE TO RELATED APPLICATION(S)

This application is a continuation-in-part of U.S. patent application Ser. No. 17/581,434, filed Jan. 21, 2022 and titled "SYSTEM AND METHOD FOR IMPROVING THE CORN WET MILL AND DRY MILL PROCESS," which will be issued as U.S. patent Ser. No. 11,623,966 and claims priority to the U.S. provisional patent application Ser. No. 63/140,342, titled "System and Method for Improving the Corn Wet Mill and Dry Mill Process," filed on Jan. 22, 2021, which are both incorporated by reference in their entirety for all purposes.

FIELD OF THE INVENTION

The present invention relates to the corn wet mill and dry mill processes and produces high purity starch as feedstock for synthetic biology, alcohols and oils as biofuels, and other co-products such as high-protein animal feed. The present invention also relates to soybean processing.

BACKGROUND

The corn wet milling process, for the last fifty years, has been used to produce starch slurries which are then converted to corn syrup for human consumption. This low-cost corn syrup has been used to replace sugar in many products. There is evidence that over-consumption of high-fructose corn syrup adversely affects human health. At the same time, the world population's consumption of petroleum-based products has created a global warming problem. Corn wet mills are seeking ways to use their existing infrastructure to produce products other than corn syrup that are more beneficial for human health and the environment.

Many companies use corn as a feedstock to replace fossil fuel-based hydrocarbons. Over 200 dry mill ethanol plants have been built and produce over 15.8 billion gallons of fuel ethanol in the USA per year. The dry mill process represents a 2000-year-old technology for converting starch in grain to alcohol. There have been some improvements, but these are only a start. More new "green" technology processes will follow in future, such as the production of butanol from starch.

FIG. 1 illustrates a typical dry mill process 100. A corn supply is fed through a hammer mill (milling) Step 109 to decrease the particle size. The screen size in the hammer mill is normally 2 mm to 3.6 mm. The corn flour produced in hammer mill particle size reduction Step 109 typically contains a very wide particle size distribution in a bell shape ranging from less than 50 micron to as large as 2 to 3 mm. Milling Step 109 is followed by a liquefaction Step (Steps 101, 102, 103A and 103B) where the ground corn meal is mixed with cook water to create a slurry in a slurry tank Step 101 and an enzyme such as alpha amylase is typically added, followed by a jet cooker Step 102 (optional) to heat the liquefied starch to a higher temperature, if needed. The pH is adjusted here to about 5.0 to 6 and the temperature maintained between about 50° C. to 105° C. to convert the insoluble starch in the slurry to soluble starch in two liquefication tank Steps 103A and 103B.

The stream after the liquefaction Steps 103A and B has about 26 to 38% dry solids (DS) content, with all the components contained in the corn kernels, including sugars, protein, fiber, starch, germ, grit, and oil and salts, for example. There generally are three types of insoluble solid particles in the liquefaction stream: fiber, germ, and grit, with all three solids having about the same particle size distribution.

Liquefaction Steps 103A and B are followed by a simultaneous saccharification and fermentation Step 104. This simultaneous step is referred to in the industry as "Simultaneous Saccharification and Fermentation" (SSF). In some commercial dry grind ethanol processes, saccharification and fermentation occur separately (not shown). Both individual saccharification and SSF can take as long as 50 to 60 hours. Fermentation converts the sugar to alcohol using a fermenter. Following saccharification and fermentation Step 104 is a distillation (and dehydration) Step 105, which utilizes a still to recover the alcohol produced in Step 104.

Finally, the "back end" of Process 100, which follows distillation (and dehydration) Step 105, includes a centrifugation Step 106 using a decanter. This involves centrifuging the residuals, "whole stillage", produced in distillation Step 104 and dehydration Step 105, to separate the insoluble solids ("wet cake") from the liquid ("thin stillage"). The "wet cake" includes fiber, of which there are three types: (1) pericarp, with average particle sizes typically about 1 mm to 3 mm; (2) tip cap, with average particle sizes about 500 microns; (3) and fine fiber, with average particle sizes of about 250 microns. The liquid from the centrifuge contains about 6% to 8% dry solids (DS).

The thin stillage enters evaporators in an evaporation Step 107 to boil away water. This leaves a thick syrup that contains the soluble (dissolved), fine suspended (generally less than 50 um) and buoyant suspended solids from fermentation Step 104. This generally amounts to about 25% to 40% dry solids. The concentrated slurry may be subjected to an optional oil recovery step (not shown) where the slurry can be centrifuged to separate oil from the syrup. The oil can be sold as a separate high-value product. The oil yield is normally about 0.4 lb./Bu of corn with high free fatty acids content. This oil yield recovers only about ¼ of the oil in the corn. About one-half of the oil inside the corn kernel remains inside the germ after distillation Step 105, and cannot be separated in the typical dry grind process using centrifuges. The free fatty acid content, which is created when the oil is held in the fermenter for approximately 50 hours, reduces the value of the oil. The (de-oil) centrifuge step removes less than 50% of oil present in thick syrup because the protein and oil make an emulsion, which cannot be satisfactorily separated by centrifugation alone as practiced today.

The centrifuged wet cake and the de-oiled syrup, which still has more than 10% (dry matter concentration) oil, can be mixed and the mixture may be sold to beef and dairy feedlots as Distillers Wet Grain with Soluble (WDGS). Alternatively, the syrup can be mixed with the wet cake, then the concentrated syrup mixture may be dried using drying at Step 108 and sold as Distillers Dried Grain with Soluble (DDGS) to dairy and beef feedlots. This DDGS has all the protein and 75% of the oil in corn. However, the value of DDGS is low due to the high percentage of fiber, and in some cases, the oil is a hindrance to animal digestion. The percentage of starch in DDGS normally is as low as 5 to 6%.

The typical dry mill process also can produce a clean sugar solution by a filtration method to remove all the insoluble solids (e.g., fiber and protein) from the liquefied starch solution. However, this clean sugar solution still contains all the soluble solids, such as ash from inside the corn, plus small amounts of corn oil. Many new green technology processes need much purer starch, without oil and soluble solids, as feedstock.

A typical corn kernel 1400 is illustrated in FIG. 14. Kernel 1400 includes a hull 1410, a floury endosperm 1420, a horny endosperm 1430, having cells filled with starch granules in a protein matrix, a germ 1440, and a tip cap 1450. A typical corn composition is illustrated in Table 1, below.

feed produced in most of today's wet mills. Co-product options include pure starch, pure sugar, yeast/germ protein meal, ethanol, and butanol. This process can efficiently produce a high yield of sustainable aviation fuel (e.g., an alcohol biofuel created by mixing sugar and culture) which is then combined with a small amount of oil; phase separation is then used to remove the biofuel from the culture

TABLE 1

Yellow Dent Corn Composition
Dry basis

| | % on Kernel | Starch | Protein | Oil | Ash | Sugars | Fiber |
|---|---|---|---|---|---|---|---|
| Endosperm | 82.90% | 88.40% | 8% | 0.80% | 0.30% | 0.60% | 1.90% |
| Germ | 11% | 11.90% | 18.40% | 29.60% | 10.50% | 10.80% | 18.80% |
| Pericarp | 5.30% | 7.30% | 3.70% | 1% | 0.80% | 0.30% | 86.90% |
| Tip Cap | 0.80% | 5.30% | 9.10% | 3.80% | 1.60% | 1.60% | 78.60% |
| Whole kernel | 100.00% | 75% | 8.90% | 4% | 1.50% | 1.70% | 8.90% |
| wt. in Lb./Bu | 47 | 35.25 | 4.183 | 1.88 | 0.705 | 0.799 | 4.183 |
| Endosperm | 38.963 | 34.44329 | 3.11704 | 0.311704 | 0.116889 | 0.233778 | 0.740297 |
| Germ | 5.17 | 0.61523 | 0.95128 | 1.53032 | 0.54285 | 0.55836 | 0.97196 |
| Pericarp | 2.491 | 0.181843 | 0.092167 | 0.02491 | 0.019928 | 0.007473 | 2.164679 |
| Tip Cap | 0.376 | 0.019928 | 0.034216 | 0.014288 | 0.006016 | 0.006016 | 0.295536 |
| pericap + ipcap | 2.867 | 0.201771 | 0.126383 | 0.039198 | 0.025944 | 0.013489 | 2.460215 |
| % comp | 100.00% | 7.04% | 4.41% | 1.37% | 0.90% | 0.47% | 85.81% |
| change after fomenter | | −32.648 | 0.375 | | 0.4 | 2 | |
| Total by product | 15.127 | 0.602 | 4.558 | 1.88 | 1.105 | 2.799 | 4.183 |
| % lab analysis | 100 | 3.979639 | 30.13155 | 12.42811 | 7.304819 | 18.50334 | 27.65254 |
| soluble solid | 3.904 | | | | 1.105 | 2.799 | |
| yeast | 0.83333333 | | 0.375 | | | | 0.458333 |
| germ | 3.45356 | | 0.95128 | 1.53032 | | | 0.97196 |
| corn protein | 4.169041 | | 3.11704 | 0.311704 | | | 0.740297 |
| pericap + tipcap | 2.827567 | 0.201771 | 0.126383 | 0.039198 | | | 2.460215 |
| Total | 15.1875013 | 0.201771 | 4.569703 | 1.881222 | 1.105 | 2.799 | 4.630805 |

SUMMARY OF THE INVENTION

This novel corn wet milling process includes a continuous steeping approach/system, a process of early separation of easy-to-access starch, fine milling to secure germ protein without the use of solvents or heat, and phase separation to collect the product of fermentation.

The process can produce high purity sugar as feedstock for synthetic biology, assorted biofuels, high-digestibility animal feed, and other valuable coproducts. A new continuous steeping tank with probiotic-infused liquid reduces total steeping time with a lower capital investment.

After the first milling of the corn kernels, the easy-to-access starch from the floury endosperm of the corn kernel is separated from the horny endosperm and the germ. The easy-to-access starch can be thoroughly washed to a high purity level. On the other hand, the horny endosperm includes harder-to-access starch bound with protein and oil. The harder-to-access starch, protein & oil are processed separately.

Novel components of this process can be used separately or in different combinations to produce multiple possible co-products beyond the traditional DDGS and gluten meal mixture, keeping the concentration of alcohol low enough to maintain the health status of the culture.

Improvement #1: Continuous Steeping Tank Design

A typical wet mill system uses 6-8 batch tanks. In contrast, as shown in FIG. 18 in accordance with some embodiments, this system includes one large tank with 6-12 internal chambers. Each chamber has 4-8 paddles moving the corn kernels progressively through the chambers by pushing kernels outwards and down to the next chamber or inwards and down to the next chamber, alternating moving directions at each chamber.

The paddles are controlled by a variable speed motor connected to a central shaft. A tank with more chambers is used in applications when more steeping time is needed.

The steeping liquid flows in from the bottom of the tank, in a countercurrent flow. For a wet mill processing corn, the steeping liquid includes four probiotic microorganisms (*lactobacillus-plantarum, lactobacillus* amylovorus, *lactobacillus* mucosae, and *Lactobacillus fermentum*) known to improve animal digestion and immune system.

In less than 24 hours, the steeping liquid increases $10^9$ CFU in probiotic concentration, and lactic acid concentration increases by 20% (dry basis). Because of the higher lactic acid concentration, the steeping time can be decreased from 50 hours to 30 hours to raise the moisture in the corn from 10% to 50%.

Improvement #2: A Process for Maximizing the Purity of Starch Retrieved from a Typical Corn Wet Mill In a typical corn wet mill system, starch from all parts of the corn kernel is processed through a 12-stage countercurrent washing system with a water-to-starch slurry ratio of 1:1 to produce starch that includes a lot of soluble proteins.

In contrast to a typical process, in some embodiments, after the first milling, the easy-to-access starch from the floury endosperm of the corn kernel is separated from the horny endosperm and the germ. The germ includes harder-to-access starch bound with protein and oil.

As shown in FIG. 19A, only the easy-to-access starch from the floury endosperm starch is then processed through the 12-stage countercurrent washing system. The amount of water used is similar to the typical process, resulting in a water-to-starch ratio that is higher (i.e., more than 1:1, 2:1, 3:1, or higher) than in the typical process. As a result, more soluble protein is washed away, resulting in a higher-purity starch slurry. This pure starch can then be used as carbohydrate feedstock for the growing synthetic biology, biochemical, and renewable chemical industries.

Improvement #3: Addition of Yeast to Germ to Create a Higher-Value Feed Product for Aquaculture As shown in FIG. 19A, after the germ is separated (but still wet), it is combined with yeast, which propagates using the small amount of starch that exists in the germ. The resulting mixture is then dewatered to make a feed product that includes germ and yeast protein. This product can improve wet mill margins over the typical production of gluten meal for chickens.

Improvement #4: A Process to Separate the Germ Protein while Preserving Protein Structure without Denaturing In the typical corn wet mill process, solvents and heat are used to separate the germ protein and oil. However, solvents typically used in the typical corn wet mills are toxic to humans. Also, the heat used denatures the germ protein, making it harder for animals or humans to digest.

In contrast to the typical process, in some embodiments, as shown in the FIG. 20A, the germ is ground to <50 microns without creating an emulsion, then the fine fiber cake, starch and protein are separated. The resulting protein is therefore produced without using toxic solvents and is more nutritious whether used in animal feed or for human consumption.

Improvement #5: A Process for Saccharification of Starch Slurry into a High-Purity Sugar Solution Typical corn wet mills that seek to produce high-purity corn-based sugar solution use a costly membrane separation process.

In contrast to the typical process, in some embodiments, as shown in FIGS. 19B and 20B, an alternative process by which the pure starch slurry derived primarily from the starch found in the harder-to-access horny endosperm is converted into a sugar solution with less than 0.0001% soluble protein (versus soluble protein of 0.05-0.1% in typical wet mill today). This sugar solution can then be used as a carbohydrate feedstock in the synthetic biology, biochemical, renewable chemical and food industries with a smaller carbon footprint than traditional sugar processes. It can also be further fermented into ethanol, butanol or other biofuels.

Improvement #6: A Process for Converting the Harder-to-Access Corn Starch into Ethanol In a typical wet mill, the starch from all parts of the corn kernel is processed into high-fructose corn syrup.

In contrast to the typical process, in some embodiments, as shown in FIG. 19C and FIG. 20C, this process converts only a portion of the starch—the starch from the horny endosperm and the germ—into ethanol.

Improvement #7: A Process for Converting the Harder-to-Access Corn Starch into Sustainable Aviation Fuel or Other Alcohol Biofuels Such as Butanol The production of ethanol entails fermenting a starch slurry to produce ethanol. As shown in FIGS. 19E and 20E in accordance with some embodiments, the liquified and saccharified solution can instead be combined with different cultures (both naturally-occurring and bio-prospected or custom-engineered) to produce different bio-based fuel products, including butanol or other alcohols, for use as a sustainable aviation fuel or feedstock for sustainable aviation fuel.

Improvement #8: A Process for Using Phase Separation to Remove the Product of Fermentation to Preserve the Health of the Culture and while Maximizing Yield of an Alcohol, Including Butanol.

Different cultures of microorganisms ferment sugars to produce different types of alcohol, including ethanol and butanol. As fermentation progresses, the concentration of alcohol in the mixture grows. At some point, the concentration of alcohol causes the death of the microorganism(s), limiting the alcohol yield of the process.

In typical corn mill processes that produce ethanol, the yeast can survive in a solution containing up to 14% ethanol; distillation towers are then used to evaporate and condense the alcohol. However, the microorganisms that produce butanol cannot survive in solutions with higher than 2% concentration of butanol.

To overcome this challenge and maintain the continued health of the culture, as shown in FIGS. 19E and 20E in accordance with some embodiments, the culture-sugar-alcohol mixture is combined with a small amount of oil. The fermentation product (e.g., butanol) attracts to the oil, liquid-liquid phase separation occurs and the butanol-oil mixture can be separated from the aqueous sugar and culture solution. The oil incorporated to instigate the phase separation can be the corn oil previously extracted from the corn kernel, any other plant-based oil, an animal-based oil, such as tallow, or a petroleum-based oil.

Improvement #9: Limit Water in the Sugar Solution to Reduce Energy Usage in the Process Different cultures of microorganisms require different levels of sugar concentration. For example, ethanol needs a 24% sugar solution while butanol needs a 6-8% sugar solution. As shown in FIGS. 19E and 20E, the process manages the amount of water added so that the solution reaches no more than the target sugar concentration. The wet mill plant can then conserve water and avoid using additional energy to evaporate water or further concentrate the solution.

Improvement #10: Use Soybeans Other than Corn in this Process and with this Equipment to Produce Soy-Based Foods for Human Consumption without Using a Carcinogenic Solvent To produce soybean oil, most soy processors currently crush the beans and mix them with the solvent hexane before pressing the beans to extract the oil. However, hexane is a carcinogen and can cause nerve damage. Moreover, the resulting soybean flour has less nutritional value because the soy protein has been denatured.

In some embodiments, the process, as shown in FIG. 21A, enables extraction of soybean oil and other soy-based products without use of any toxic solvents.

DETAILED DESCRIPTION OF THE PREFERRED EMBODIMENTS

Figure 14:
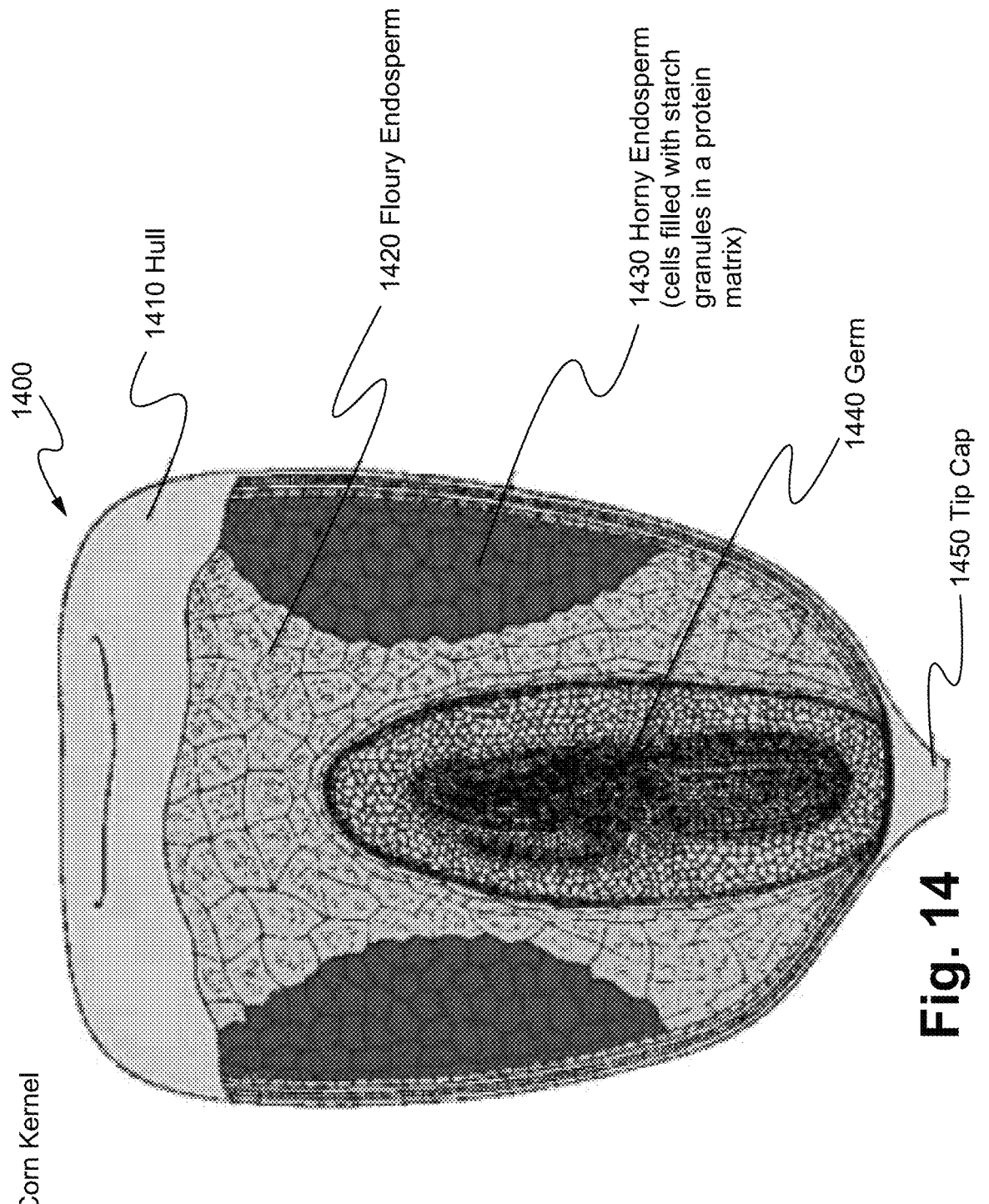
FIG. 14 illustrates a corn kernel in accordance with some embodiments.

A Yellow Dent Corn Kernel is illustrated in FIG. 14 and its composition is illustrated in Table 1. There are 34.4 lbs. of starch per bushel of corn. Most starch is contained in two types of endosperm: floury endosperm and horny endosperm. The starch inside floury endosperm is loosely packed inside the endosperm and quite easy to separate out (e.g., easy-to-separate starch). It can be used to produce pure starch as feedstock for green technology processes. The starch in horny endosperm (e.g., hard-to-separate starch) is contained in cells filled with granular starch in a protein matrix. The starch in horny endosperm is not easy to separate out as it is bound with protein.

Figure 10:
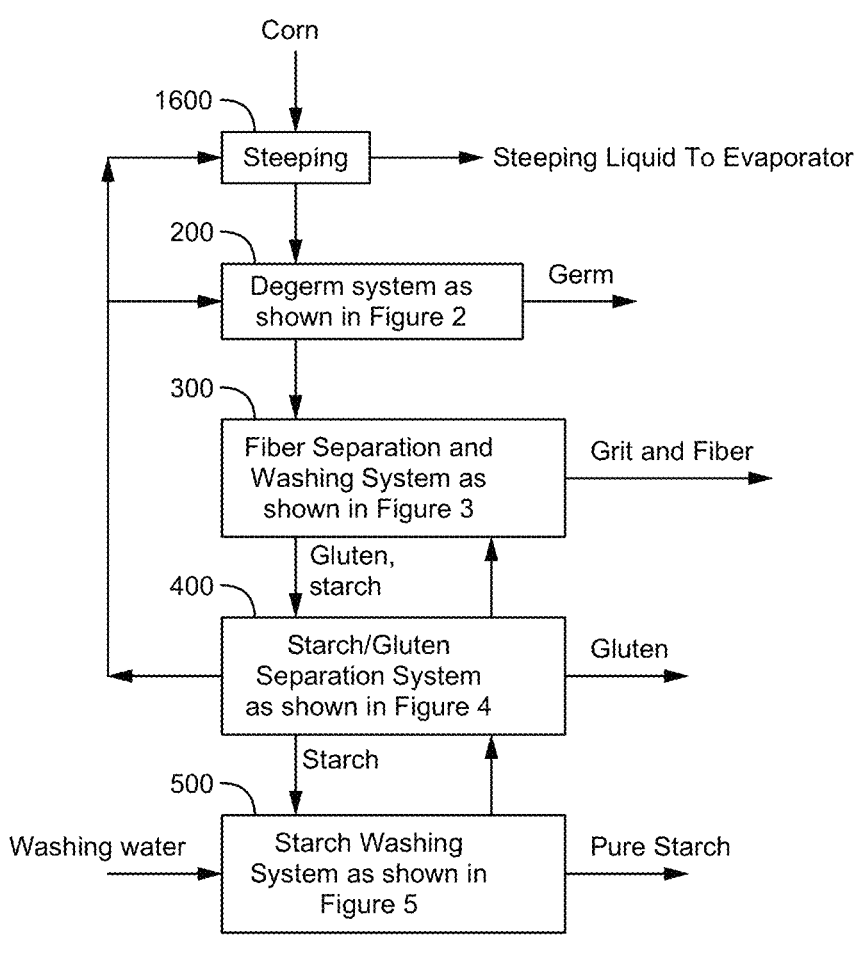
FIG. 10 illustrates a wet mill flow diagram in accordance with some embodiments.

In some embodiments, a process is illustrated, which combines starch (in most pure form from the floury endosperm) and all the rest of the corn compounds (pericarp, tip cap, fine fiber, corn protein, germ and grit) as feedstock for a dry mill process to produce alcohol and by-products, such as organic oil for human consumption, corn oil for biodiesel, animal feed for cows, chicken, pigs, fish, and household pets, etc. A similar wet mill system is illustrated in Process 1000 of FIG. 10.

In some embodiments, a process only separates about half (e.g., 15 lb./bu) of "free" starch from the floury endosperm with a simple low-cost improved wet mill process. The process uses the rest of the corn as feedstock to produce alcohol and higher value-added byproducts with an improved dry mill process, is which described in detail below. In comparison, a typical dry mill process converts all the starch in corn to alcohol and uses more 2000-year-old technology.

In some embodiments, a process provides an effective way to separate the starch from the floury endosperm first and uses the rest of corn as feedstock for producing alcohol and high value co-products with an improved dry mill process.

A) Improved Wet Mill Process in Accordance with Some Embodiments

Figure 11:
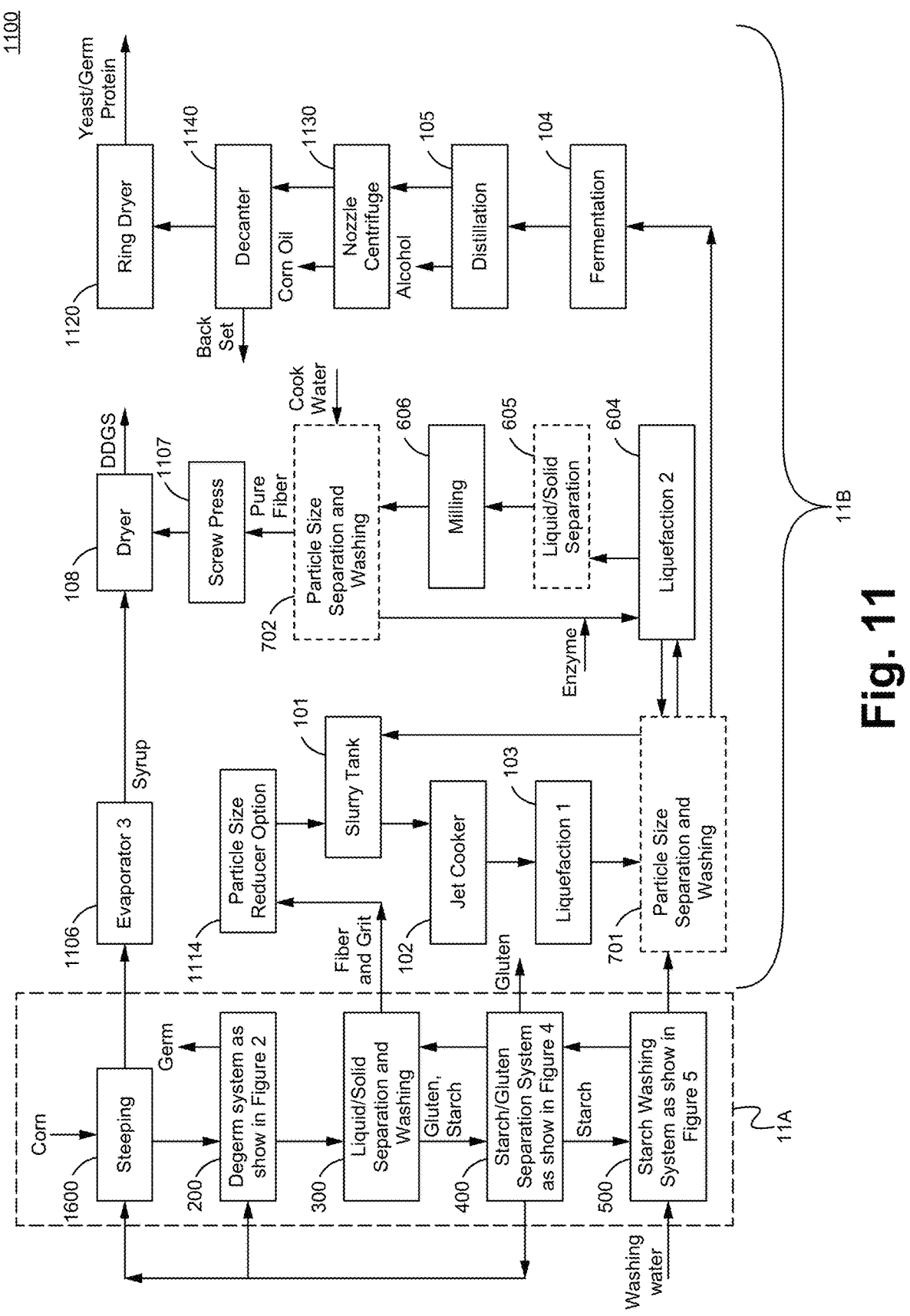
FIG. 11 illustrates improved wet mill process to produce fuel alcohol in accordance with some embodiments.

As illustrated in Process 1100 of FIG. 11, the corn goes through five steps to produce a pure starch slurry as a feedstock for green technology processes. The rest of the corn is used as feedstock for the dry mill process to produce alcohol and byproducts such as animal feed. The five steps process includes: a) soaking/steeping process 1600 is used for softening and hydrating the corn to have more than 45% moisture; b) de-germing process 200 which uses about 120 Baumé starch slurry as a liquid media to separate germ from grit and fiber by using density differences through the use of two different sets of dual degerm cyclone processes 200; c) using a new three section paddle screen process 300 to wash off starch from grit and fiber before being used as feedstock to produce alcohol and valuable byproducts such as animal feed; d) using a starch/gluten separation process 400 with a dual nozzle centrifuge to remove gluten from starch and produce byproducts including gluten meal as chicken feed; and e) purifying the starch slurry in a 12-stage starch washing process 500 with a 10 mm starch washing cyclone net and a counter-current washing set-up.

In FIG. 11, process 11A illustrates a portion of the process for producing pure starch, liquid starch or pure corn sugar (e.g., for biotech feedstock) in accordance with some embodiments. Process 11B illustrates the other portion of the process for making alcohol in accordance with some embodiments.

Following are Short Descriptions of Each Step in More Detail:

1) Soaking/steeping process 1600 in the FIG. 11: The corn kernels are soaked/steeped in a 100 to 600 PPM sulfur dioxide water solution at about 50° C. (just below starch gelatin temperature) for 5 to 60 hours to soak and soften the corn kernel. The soaking/steeping time depends on desired starch yield and purity needs. Longer soaking/steeping gives higher starch yield as well as higher purity starch. The soaking/steeping process 1600 can be a continuous or a batch system. Larger plants or existing wet mill plants can use the typical batch system. New and small plants can use a new continuous soaking/steeping system. The process water used for the soaking/steeping process 1600 comes from the gluten nozzle centrifuge overflow in a system such as in Process 400 of the FIG. 4. The process water can add lactic acid producing cultures to produce lactic acid before being sent to the steeping tank to speed up this soaking/steeping process.

Soaking/steeping process 1600 is normally set in counter-current mode to maximize extraction of soluble solids (e.g., ash) from the corn. The soaking/steeping corn kernels fully absorb water and have more than 45% moisture in less than 10 hours. The steeping liquid from this soaking/steeping step has about 8 to 10% solids, and is then sent to evaporator 3 at Step 1106 to concentrate the stream to around 30 to 40% DS (dry substance) syrup. This syrup contains most plant nutrients ($K^+$ and $P^+$) plus a lot of lactic acid (up to 10% in DB (dry basis)) which can be used as a natural organic insect repellent to keep bugs away from young plants. The concentrated syrup also can be mixed with fiber from a screw press at Step 1107, then dried in a dryer at Step 108 to produce DDGS as cattle feed.

Figure 1:
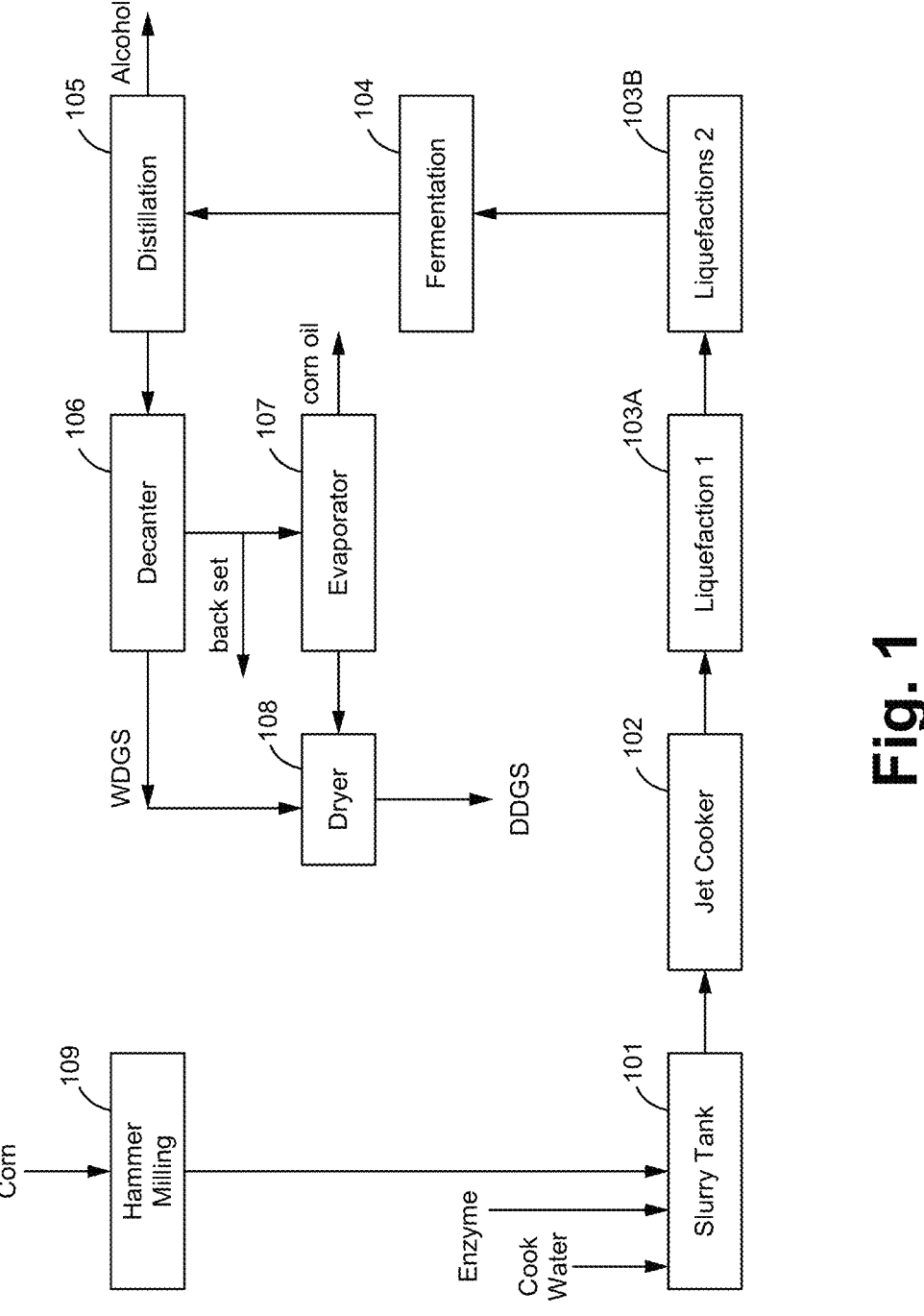
FIG. 1 illustrates a typical dry mill process.
Figure 2:
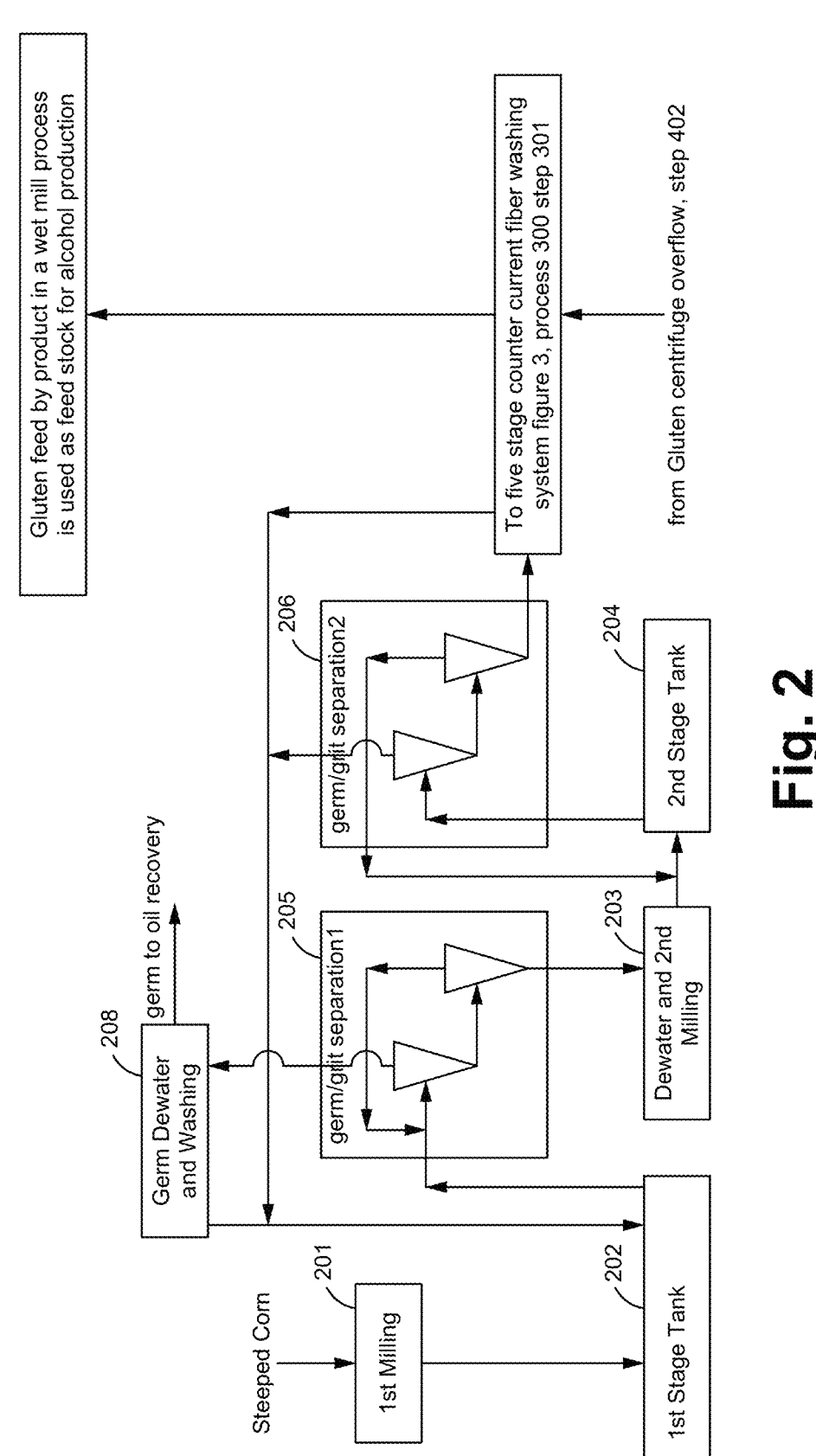
FIG. 2 illustrates a degerm process using germ cyclone (e.g., germ separation) in accordance with some embodiments.

2) The de-germ process 200 in FIG. 11 after Process 1600, which can be the same or similar to Process 200 of FIG. 2: The soaking/steeping corn kernels with more than 45% moisture is fed to the de-germ process 200 in FIG. 2. The soaking/steeping corn is fed to the 1$^{st}$ milling at Step 201 of FIG. 2 to tear open the corn to release the starch and drop to the 1$^{st}$ stage tank at Step 202 to form an about 12° Baumé starch slurry. A grind mill or roller mill can be used to open the corn kernels. This 12° Baumé starch slurry is used as a liquid media to float the germ in two dual germ cyclone processes, which includes a 9-inch degerm cyclone followed by an 8-inch de-germ cyclone. Optionally, a 6-inch cyclone process (a 6-inch A cyclone followed by another 6-inch B cyclone) can also be used in a small plant.

At Step 205, the 12° Baumé starch slurry with germ, grit and fiber particles are fed to a 1$^{st}$ set of dual germ cyclones in the 1$^{st}$ germ/grit separation. Since the germ particles are lighter than the liquid, the germ particles come off at the top of the first germ (9 inch) cyclone as an overflow, which are next sent to germ dewater and washing at Step 208 to produce pure germ for further extracting corn oil thereafter. Still at Step 205, the underflow from the first (9 inch) cyclone is fed to a second (8 inch) cyclone. Still at Step 205, the overflow from the second (8 inch) cyclone is sent back to the 1$^{st}$ stage tank set at Step 202. The grit and fiber heavier than the liquid come out from the bottom of the second cyclone as underflow, followed by dewatering and milling at Step 203 and sent to a 2$^{nd}$ stage tank at Step 204. The 12° Baumé starch slurry with residual germ particles that are not removed during the 1$^{st}$ germ/grit separation at Step 205 are fed to the 2$^{nd}$ germ/grit separation at Step 206 with the other set of dual degerm cyclone processes at Step 206 to recover more germ.

Figure 3:
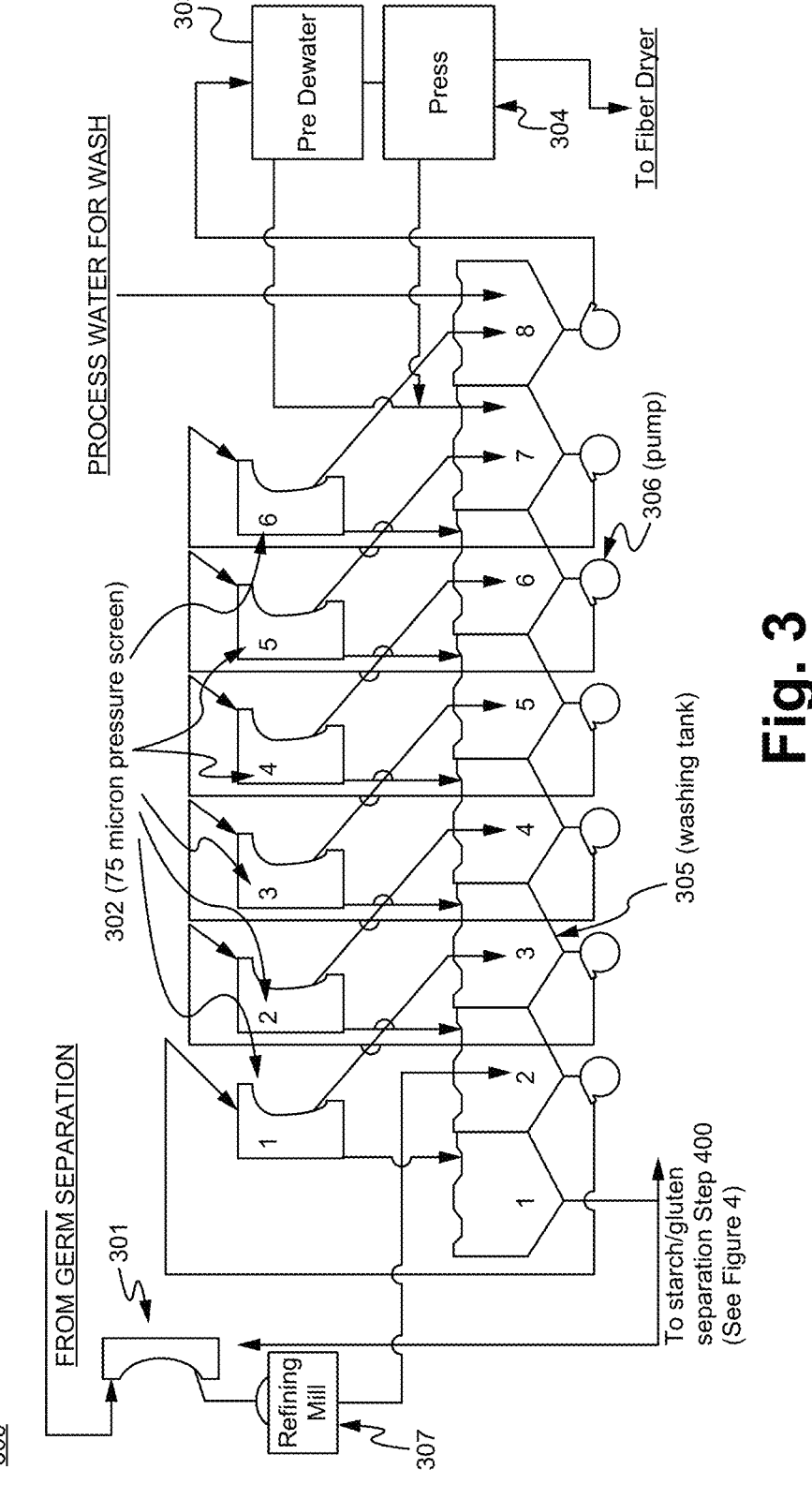
FIG. 3 illustrates a fiber washing process (e.g., fiber separation) with multi-stage pressure screen counter-current washing in accordance with some embodiments.

In the second set dual germ cyclone process, the overflow from the first germ cyclone is recycled back to the 1$^{st}$ stage tank at Step 202. The underflow from the first cyclone is fed to the second cyclone and overflow from the second cyclone is recycled back to the 2$^{nd}$ stage tank at Step 204. The underflow from the second cyclone is fed to a three section paddle screen at Step 300 (continue at Process 300 of the FIG. 3) to wash the free starch out of the grit/fiber before sending it to produce alcohol and byproducts such as animal feed.

3) Liquid/solid separation and washing at Process 300 in Process 1100 of the FIG. 11: The new three section paddle screen described in the U.S. Provisional patent application 63/131,035 is incorporated herein by reference, which can be used to separate grit and fiber from the starch slurry as a degerm process 200 underflow. This new paddle screen has a three sectional screen: a) a first screen with 50-micron slots open, for example, parallel to the flow; b) 2$^{nd}$ and 3$^{rd}$ screen sections with 75-micron slots open, for example, parallel to the flow. The underflow from the last de-germ cycle contains a 12° Baumé starch slurry with grit, fiber, and larger solid particles is fed to this three-section paddle screen at Step 300. The overflow from the gluten centrifuge at Step 402 of FIG. 4 can be used as washing water in this step. The filtrate from the first screen section can be fed to starch/gluten separation in Process 400. The filtrate from the 2$^{nd}$ and 3$^{rd}$ screen section can be fed to the 1$^{st}$ stage tank at Step 201 to mix with ground corn from Step 201 to form a 12° Baumé starch slurry in the 1$^{st}$ stage tank at Step 201.

Figure 4:
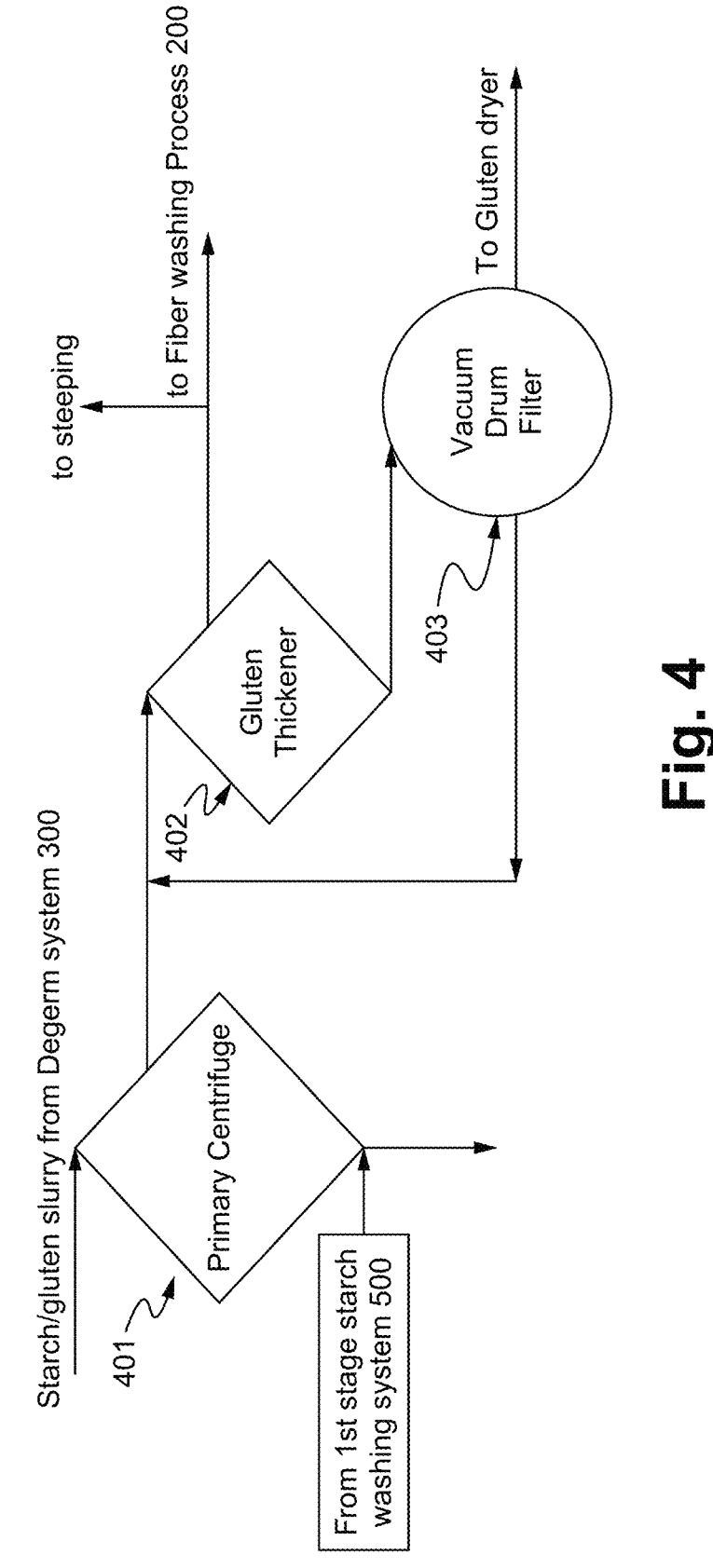
FIG. 4 illustrates a starch/gluten separation process (e.g., starch and protein separation) in accordance with some embodiments.

4) Wet milling process 1100 of FIG. 11 includes starch/gluten separation process 400 of FIG. 4: The 12° Baumé starch slurry from the first filtration from the three-section paddle screen at Process 300 is sent to the starch/gluten separation at Process 400. The 12° Baumé starch slurry is sent to a primary centrifuge at Step 401 to separate gluten from starch in starch/gluten separation process 400 in Process 400 of FIG. 4.

At Step 401, the starch slurry (around 22° Baumé) comes out as the heavy phase from a primary nozzle centrifuge. The washing water from a first stage starch washing at Process 500 of FIG. 11 is fed from the bottom of the primary nozzle centrifuge at Step 401 as replacement washing water at the outer edge of the inter bowl of the primary centrifuge at Step 401 to wash gluten from the starch before the starch comes out as the heavy phase from the nozzle of the primary nozzle centrifuge at Step 401. The gluten that is lighter than the starch will come out as the light phase from the top of primary centrifuge at Step 401. It is then fed to a gluten thickener centrifuge at Step 402 to further concentrate the slurry to more than 30% by volume gluten, as underflow.

At Step 402, clean process water comes out as the light phase from the top of gluten nozzle centrifuge. The clean water is used as process water for the de-germ at Process 200, grit and fiber separation and washing at Process 300, and steeping water for soaking/steeping at Process 1600. The underflow from the gluten thickener centrifuge at Step 402 is sent to a vacuum drum filter to further dewater the gluten to produce about 40% Dry Solids gluten cake. The cake is further dried in a dryer to produce gluten meal, which can be used as chicken feed.

Figure 5:
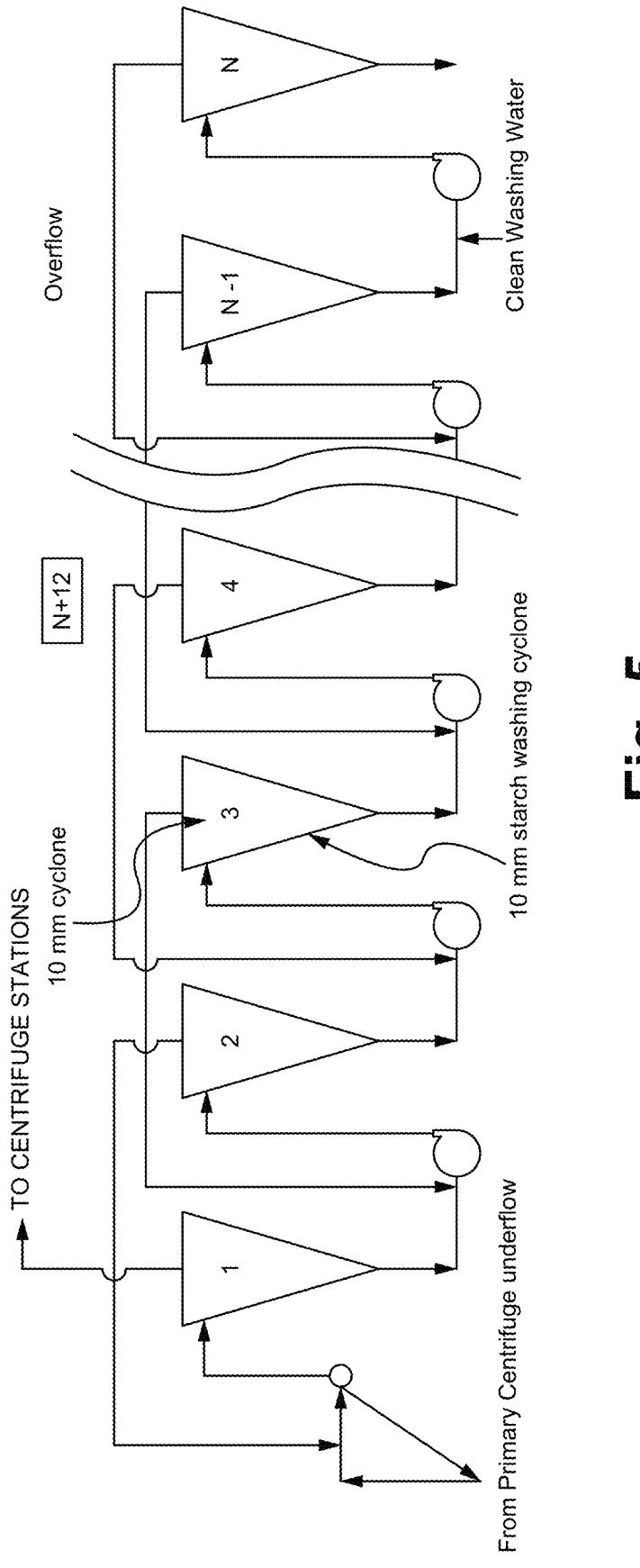
FIG. 5 illustrates a starch washing process (e.g., starch washing and purification) in accordance with some embodiments.

5) Starch washing Process 500 of Process 1100 in FIG. 11, which can be the same or similar as it is further described in more detail in FIG. 5. An approximately 20° to 22° Baumé starch slurry from the primary centrifuge underflow is mixed with the overflow from the 2$^{nd}$ stage of a multi- (normally 12) stage 10 mm starch washing cyclone net. The slurry is then fed to the 1$^{st}$ stage 10 mm starch washing cyclone net to perform dilute washing and to separate and purify the starch slurry by removing soluble and insoluble protein from the starch slurry with a counter-current washing setup. The starch slurry flows downstream from the 1$^{st}$ stage to a 2$^{nd}$ stage, then continues to a 3$^{rd}$ stage and so on until it comes out as a last (12th) stage starch washing cyclone underflow as a pure 23° Baumé starch slurry with less than 0.35% protein on a dry basis. The clean water used as the washing water enters the last (12th) stage, then flows upstream to perform the dilution washing/separation from stage 12 to stage 11. The water then continues to flow countercurrent to stage 10, and so forth until it comes out from the 1$^{st}$ stage starch washing cyclone overflow, which will be used as the washing water in the primary centrifuge in starch/gluten separation at process 400 (described in detail in the FIG. 4).

The starch slurry flows though fiber washing Process 300, gluten/starch separation Process 400, and starch washing Process 500, to maximize starch yield and purity. When this high starch yield and purity in the starch slurry is not needed, some of the starch purification steps can be eliminated to meet the starch purity specification for any particular green technology process.

The solid phase from Liquid/solid separation in Process 300 of the FIG. 11 contains much less starch than corn. This can be taken into consideration to use this as a feedstock for alcohol production. It is important to remove the fiber and germ in the front end (prior to fermentation and during the liquefication) in order to produce high alcohol content in the beer.

The solid phase (grit and fiber) from liquid/solid separation at Process 300 of FIG. 11 can go through another optional particle size reducing at Step 1114 before going to the slurry tank at Step 101, followed by a jet cooker at Step 102 and liquefaction tank 1 (higher than 26° Baumé) at Step 103 to liquefy the starch. The slurry is then fed to liquid/solid separation at Step 701 to separate solid (grit and fiber) from liquid (liquefied starch). The solid (grit and fiber) from liquid/solid separation at Step 701 is sent to liquefaction tank 2 at Step 604 (lower than 5° Baumé) to further liquefy the starch in a much lower Baumé setting. This is followed by liquid/solid separation at Step 605, then milling at Step 606 to break solid (grit) further. The slurry is then fed to liquid/solid separation and washing at Step 702.

Cook water is used to wash any starch/grit/protein off the fiber to produce pure fiber before fermentation. The washed fiber follows to screen press at Step 1107 to produce 43% DS cake. It is then mixed with the syrup from the evaporator at Step 1106 and fed to the dryer at Step 108 to produce DDGS. The steeping liquid from soaking/steeping at Process 1600 contains mainly soluble solids from inside the corn. It is sent to evaporator 3 at Step 1106 to concentrate the liquid to 30 to 40% DS syrup. It is then mixed with the fiber to produce DDGS.

The above liquefication tanks with high Baumé (>26° Be) liquefication at Step 103 and low Baumé (<5° Be) liquefication at Step 604 flow are connected to the new three-section paddle screen with high rate washing capability at Step 701 in accordance with some embodiments. The screen of the 1$^{st}$ section can be 75 microns (can be 50 to 200 microns, depending on oil and alcohol yield) with the screen slots parallel to the direction of flow. The 2$^{nd}$ and 3$^{rd}$ section screens can be 200 microns (100 to 600 microns, depending on oil and alcohol needed) with the screen slots open parallel to fluid flow. The filtrate from the first screen section can be sent to fermentation at Step 104. The filtrate (washing liquid) from the 2$^{nd}$ and 3rd screen sections can be recycled back to slurry tank at Step 101 of FIG. 11. The liquid from three section paddle screen at Step 702 can used as washing water to wash off any germ and grit and fine fiber particles smaller than 200 microns. The filtrate with those middle size solid particles is recycled back to the slurry tank.

The whole stillage, after fermentation at Step 104 followed by a distillation at Step 105, is sent to a nozzle centrifuge at Step 1130 to separate oil from protein. The oil stream comes out as the light phase from the clarifier as feedstock for biodiesel production. The protein stream comes off as the heavy phase from clarifier at Step 1130 and is sent to protein decanter at Step 1140 for dewatering to produce a yeast protein wet cake. The cake is further dried in a ring dryer at Step 1120 to produce high grade protein for household pets and fish farms. The overflow from protein decanter at Step 1140 is recycled as a backset stream.

B) Improved Dry Mill Process

As illustrated in FIG. 14 and Table 1, there is about 34 lb/bu starch inside corn kernels. The starch in the floury endosperm is "free" starch, loosely packed inside and very easy to separate to "free" pure starch granules. Thus, the "free" starch disclosed in the Present Disclosure is referred to as "free starch" or "freed starch" when such starch is released out from the kernels.

The starch in the horny endosperm is in the form of starch granules in a protein matrix (called grit), which is not easily broken up to release the starch. One object of this disclosure is to provide a simple and effective way to separate starch from the floury endosperm (e.g., free starch) and produce a purer form of corn sugar for biotech processes. Then all the rest of the corn kernel components (pericarp, tip cap, germ, and grit) are used as a feedstock for an improved dry mill process to produce alcohol and high value byproducts (oil and animal feeds.) Thus, when it is referred to as a free starch or freed starch, such starch is primarily or more than a substantial portion (e.g., greater than 50%, 75%, or 99%) originally contained in the floury endosperm of the corn.

Figure 15:
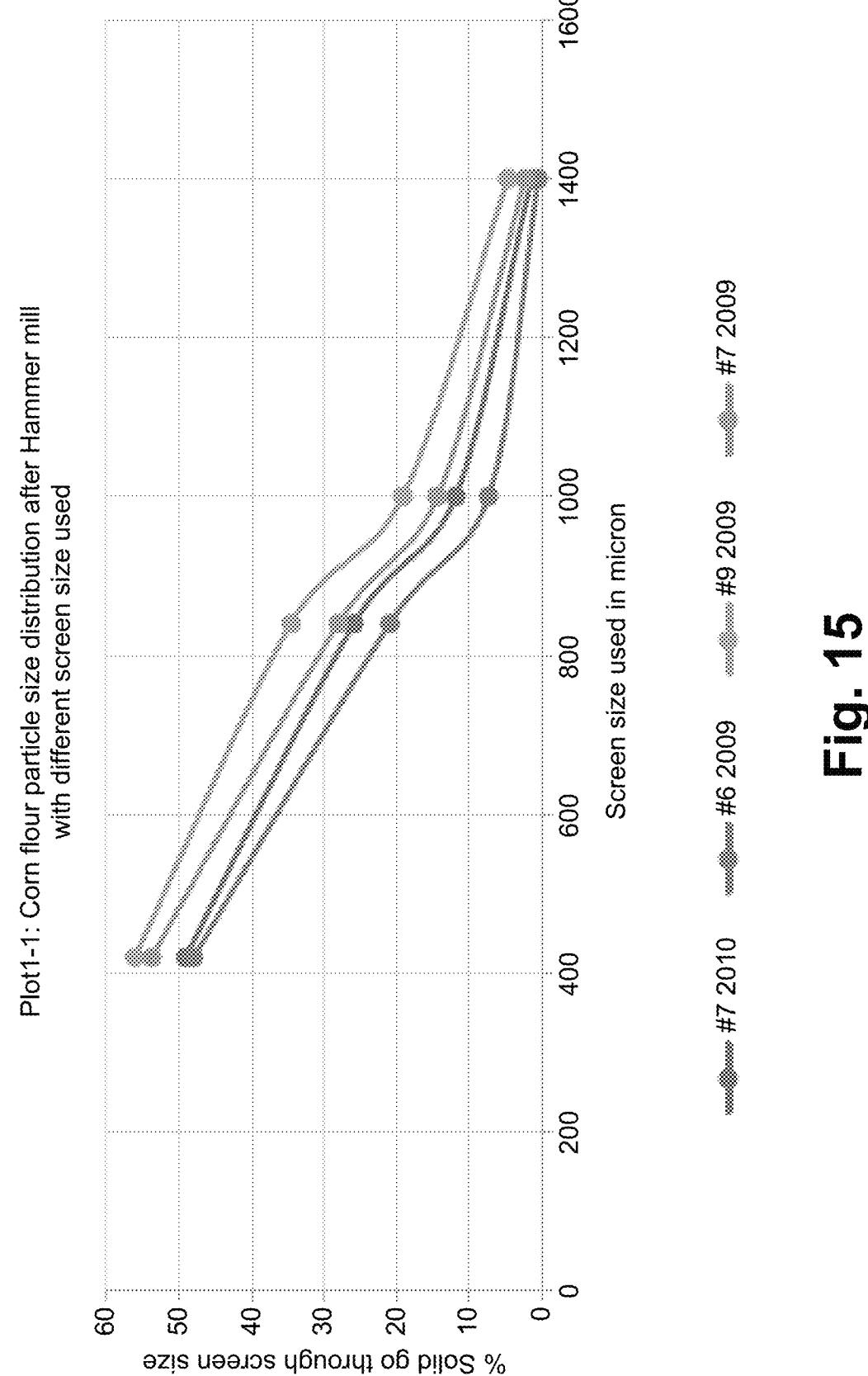
FIG. 15 illustrates corn flour particle size analysis after hammer milling, with different screen sizes in accordance with some embodiments.

As illustrated in FIG. 15, plot 1-1 shows a corn particle size distribution after hammer milling with various screen sizes. It shows that about 50% of the corn flour particles are larger than 500 microns and a majority of the particles are pericarp, tip cap, germ, and grit.

Figure 16:
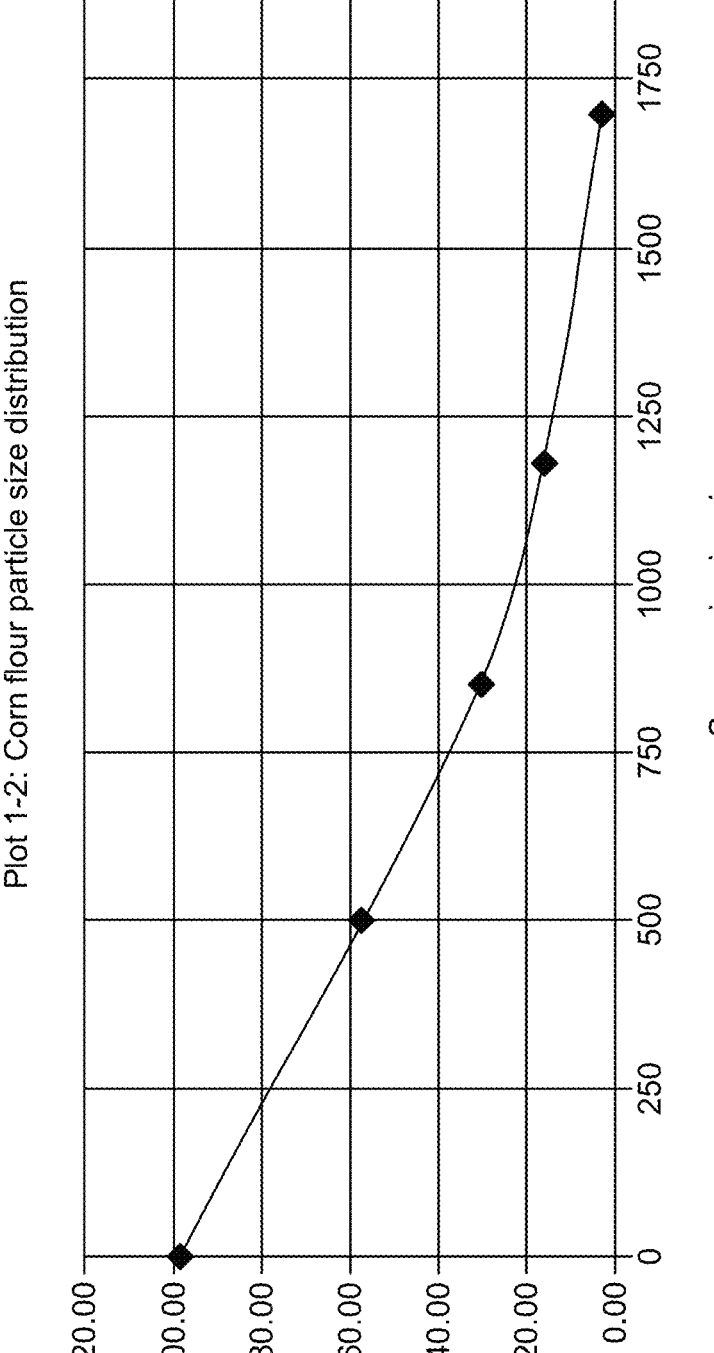
FIG. 16 illustrates corn flour size distribution in accordance with some embodiments.

Referring to FIG. 16, plot 1-2 shows the average particle size in corn flour in USA dry mill plants. It shows that about 10% of the corn flour has a particle size smaller than 125 microns, 20% corn flour is smaller than 240 microns, 30% corn flour is smaller than 375 microns and 40% corn flour is smaller than 500 microns. Those small particles are mainly starch from floury endosperm and horny endosperm.

Figure 17:
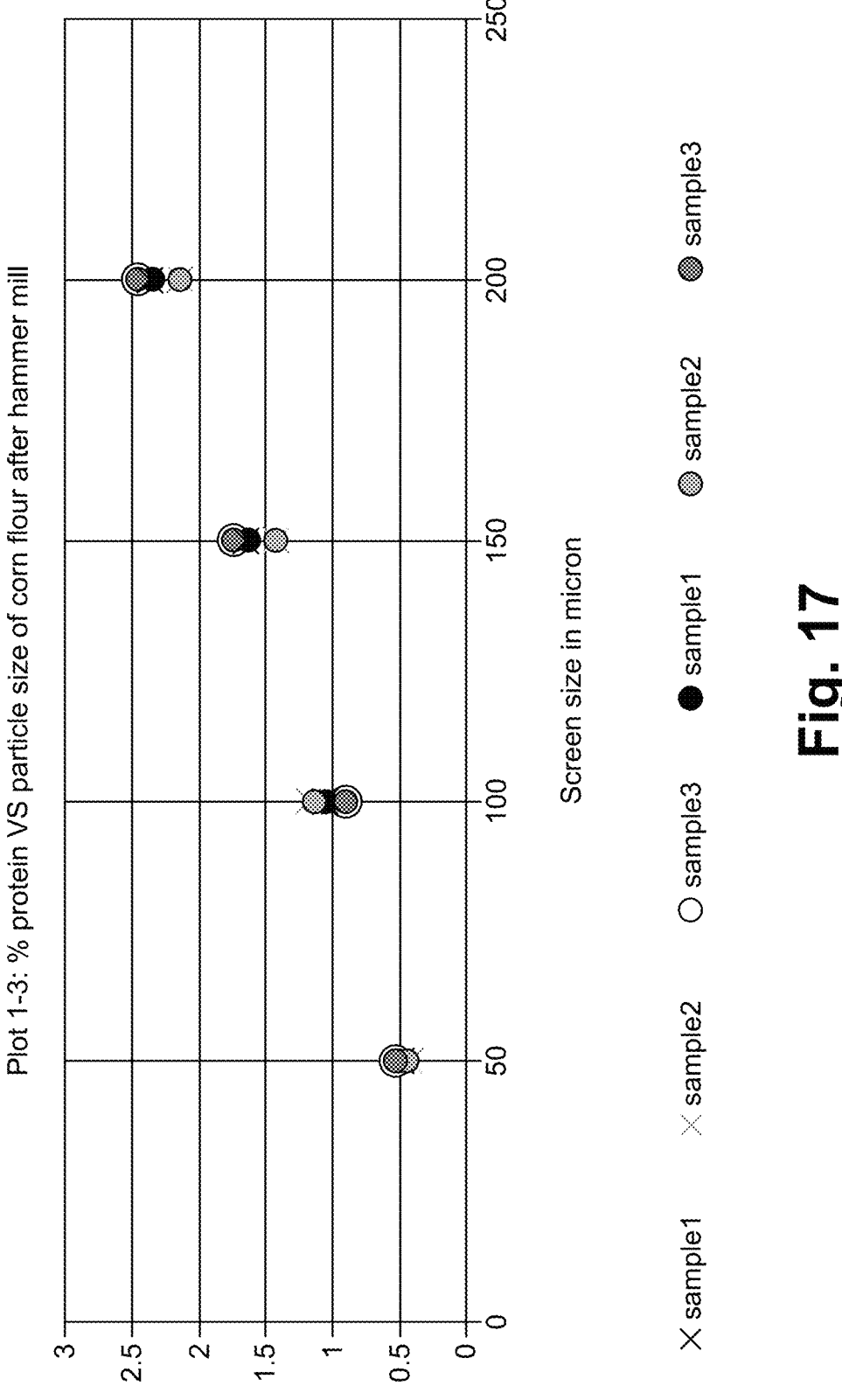
FIG. 17 illustrates protein v. particle size of corn flour after hammer milling in accordance with some embodiments.

The percentage of protein in those small corn flour particles are shown in FIG. 17, plot 1-3. This shows that smaller particles are starch from the floury endosperm with lower protein. Therefore, it is possible to separate and produce "free starch" or freed starch from the floury endosperm. This "free" starch yield and purity (% protein) can be controlled by the screen size used in separation at Step 703 of FIG. 7. Any screen separation method, such as a vibration screen, can be used in this screening step. The particles smaller than the screen openings go through the screen at Step 703, to liquefication at Step 704 and saccharification at Step 705, to produce corn syrup. They are then sent to the mud centrifuge at Step 706 to separate any oil/germ as light (mud) phase then followed by the precoat drum filter at Step 707 to remove any fine solids and produce clean pure corn syrup for biotech processes.

In some embodiments, grinding the larger particles one or more times increases pure starch yield or improves pure starch purity. Any solid particle size reducer such as roller mill or pin mill can be used. The larger particles stay on top of the screen at Step 703 and can be used as feedstock for an improved dry mill process to produce various byproducts.

Following are some improvements to the dry mill process in accordance with some embodiments.

Figure 7:
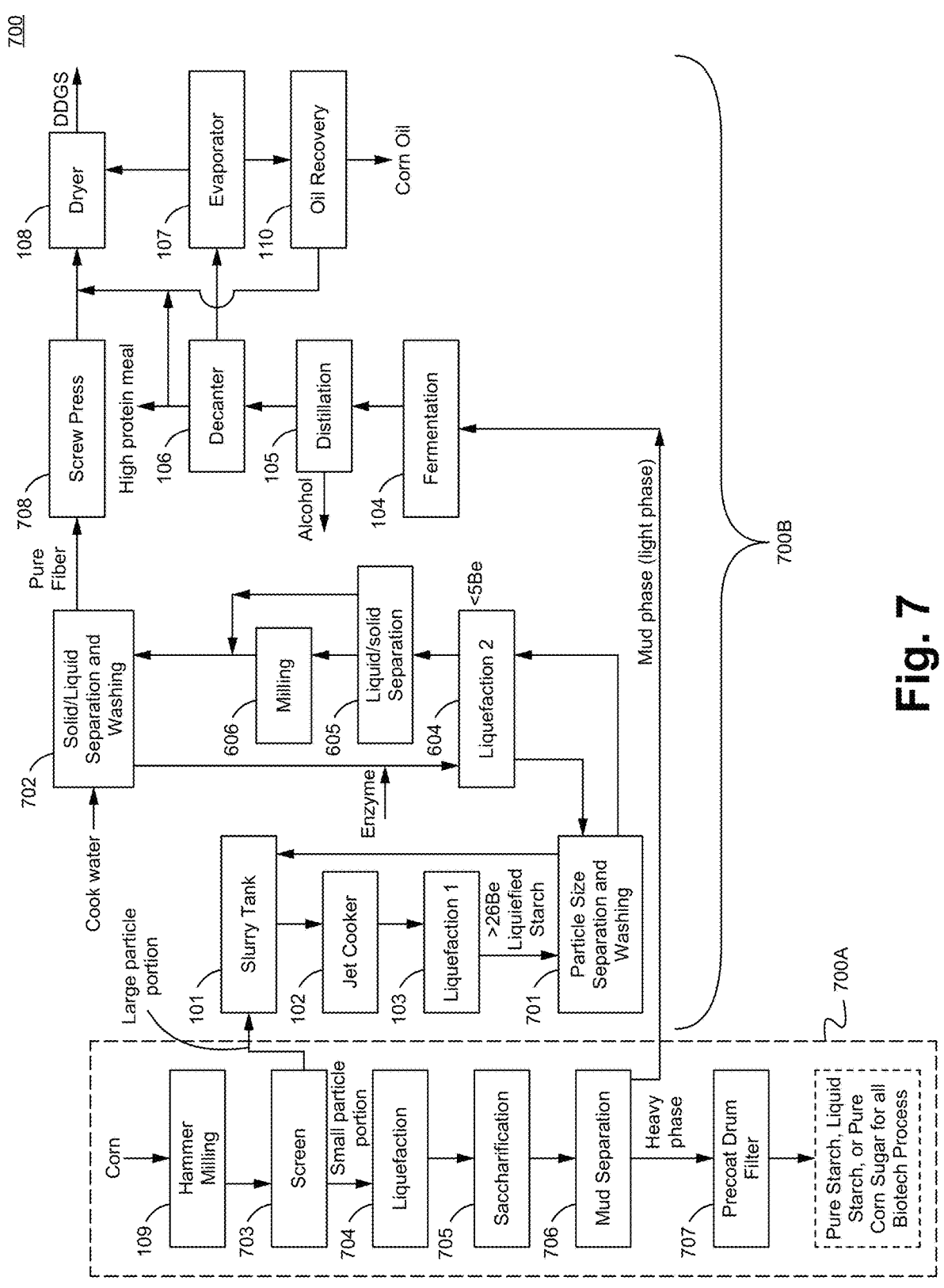
FIG. 7 illustrates an improved dry mill process to produce pure starch for biotech processes and produce pure fiber before fermentation in accordance with some embodiments.

1) Process 700 of FIG. 7: Improved Dry Mill Process with Removed Fiber Before Fermentation.

The larger solid particles from screen separation at Step 703 are sent to the slurry tank at Step 101 with filtrate from liquid/solid separation at Step 701, which are used as cook water as a starting point of the liquefication process, followed by a jet cooker at Step 102 and liquefication 1 at Step 103 to liquefy the majority of starch at a higher temperature (above 110° C.) and higher Baumé slurry. The high Baumé liquefied starch slurry with grit, germ and fiber is sent to liquid/solid separation and washing at Step 701. The new three-section paddle screen is used separate a high Baumé liquefied starch slurry with small grit and germ particles (depending on screen size used on this paddle screen) from the first screen section and sent to fermentation at Step 104. The overflow from liquefication 2 at Step 604 can be used as the washing water for the second and third screen sections of the three-section paddle screen to wash off the liquefied starch from the solid particles (grit, germ and fiber).

In FIG. 7, Process 700A illustrates a portion of the process for producing pure starch, liquid starch or pure corn sugar (e.g., for a biotech feedback) in accordance with some embodiments. Process 700B illustrates the other portion process for making alcohol in accordance with some embodiments.

At Step 604, the output is a wet washed cake, sent to liquefication 2. The solids will continue to soak/cook in a low Baumé (e.g., less than 5 Be) slurry to further soften grit and germ particles. This is followed by liquid/solid separation and dewatering at Step 605, then particle size reduction milling at Step 606 to break up the grit and germ particles to release more starch and oil. This is followed by liquid/solid separation and washing at Step 702 to produce pure fiber (less than 3% starch, less than 4% oil and less than 15% protein) at around 3 lb./bu yield. This pure fiber is ideal feedstock for secondary alcohol production and paper industry use. It can also be followed by a screw press at Step 708 to produce 43% DS cake. The cake can be mixed with de-oiled syrup at Step 110, then dryer at Step 108 to produce 20 to 30% pro-fat cattle feed per market needs. The high protein cake from decanter at Step 106 can all or partially be added to the dryer at Step 108 to increase the pro-fat in the DDGS up to 30%.

The whole stillage, after fermentation at Step 104 and distillation at Step 105, is sent to the decanter at Step 106 to remove the solids (mainly protein and fine fiber). The overflow (thin stillage from decanter at Step 106) is sent to evaporation at Step 107, to concentrate the fluid to 30 to 35% DS syrup, followed by oil recovery at Step 110 to recover oil for biodiesel production. The oil recovery from oil recovery at Step 110 occurs after fermentation, and is dark in color and high in fatty acid content (up to 10%) and not ideal to be used for human consumption. The oil should be recovered before fermentation if it is to be used for human consumption, as described below.

Figure 6:
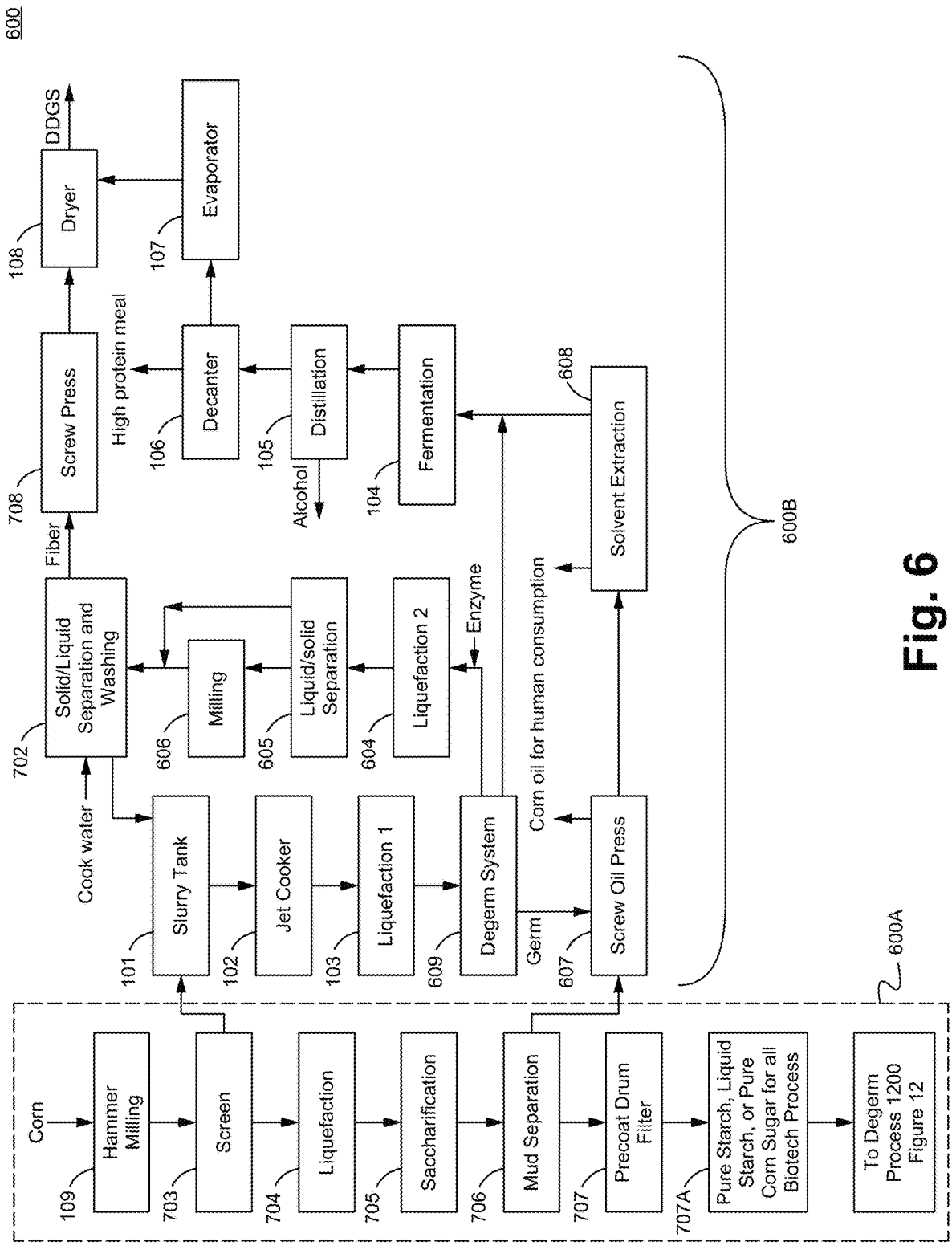
FIG. 6 illustrates an improved dry mill process to produce pure starch for biotech processes and separate fiber and germ before fermentation in accordance with some embodiments.

2) Process 600 of FIG. 6: An Improved Dry Mill Process with Removal of Fiber and Germ Before Fermentation The corn flour, after the hammer mill at Step 109, is sent to screen size separation at Step 703, to separate fine solid particles (mainly starch from the floury endosperm) from coarse solids (mainly germ, grit, and fiber). The fine solid portion proceeds to liquefication at Step 704 and Saccharification at Step 705 to produce corn syrup. It is then sent to a mud centrifuge at Step 706 to separate any oil/germ as light phase mud. The light mud proceeds to a precoat drum filter at Step 707 to remove any fine solids and produce clean, pure corn syrup for biotech processes.

Figure 12:
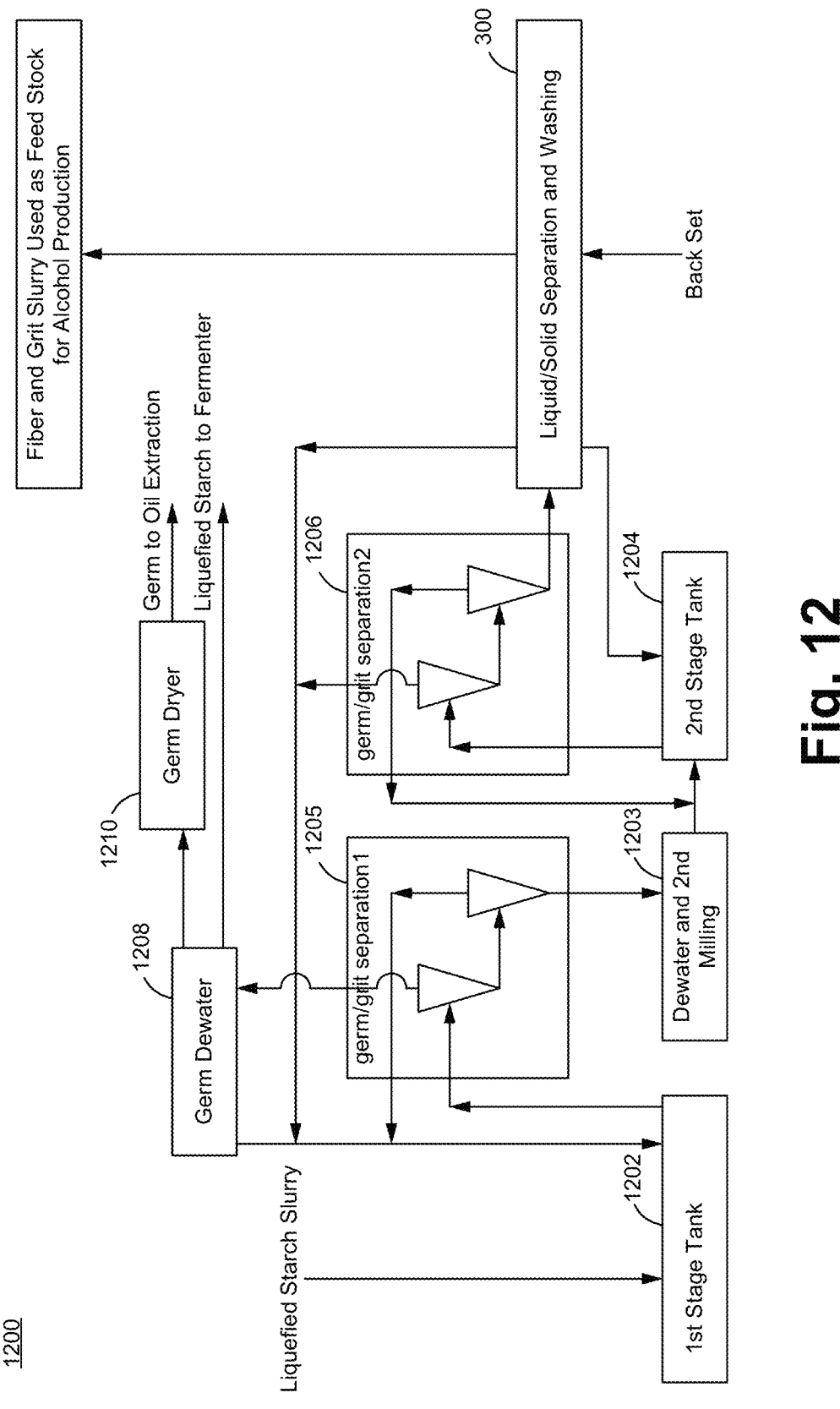
FIG. 12 illustrates a two-stage dual germ cyclone process to recover germ after liquefication in improved dry mill process in accordance with some embodiments.

The larger solid particles from screen separation at Step 703 are sent to a slurry tank at Step 101, with filtrate from liquid/solid separation at Step 701 used as cook water to start liquefication. Jet cooker at Step 102 and liquefication 1 at Step 103 are used to liquefy a majority of the starch at higher temperatures (above 110° C.) becoming a high Baumé slurry. The high Baumé liquefied starch slurry with grit, germ and fiber is sent to degerm at Step 609 (as shown in FIG. 12) to separate germ from grit and fiber by density difference, using liquefied starch slurry as the liquid media. A two-stage dual germ cyclone can be used for this degerm process. A 9 inch cyclone can be followed by an 8 inch cyclone, or a 6 inch A cyclone followed by a 6 inch B cyclone, as is commonly used in the industry.

Process 1200 of FIG. 12: The liquefied starch slurry with germ, grit and fiber particles are pumped to a first set of dual germ cyclones at Step 1205, to separate germ from grit and fiber by density differential. The germ particles lighter than the liquefied starch slurry will come off as the light phase from the top of the first germ cyclone. The germ is then washed and dewatered at Step 1208 to produce germ for production of corn oil.

The grit and fiber particles heavier than the liquefied starch slurry comes off the bottom of second set dual germ cyclone at Step 1206. The grit and fiber are then subjected to 2$^{nd}$ milling at Step 1203 to break up the grit (horny endosperm) to release more starch. The milled grit and fiber are then sent to the $2^{nd}$ stage tank at Step 1204. The heavy liquefied starch slurry with broken grit from the $2^{nd}$ stage tank at Step 1204 is fed to $2^{nd}$ set dual germ cyclone at Step 1206. The light phase from the first degerm cyclone contains the liquefied starch slurry with any germ particles not recovered from first set dual germ cyclone, and is recycled back to first stage tank. The heavy phase from the bottom of the second germ cyclone is discharged to liquid/solid separation at Process 300 (new three-section paddle screen) to separate fine particles (less than 50 microns) of starch and gluten from larger particles (grit and fiber). The fine particle stream with liquefied starch is recycled back to a second stage tank at Step 1204. The back-set stream used as wash water in the three-section paddle screen is used to wash off the liquefied starch from the grit and fiber particles in the $2^{nd}$ and $3^{rd}$ screen sections. The wash liquid is recycled back to first stage tank at Step 1202.

The washed grit and fiber particles from the three-section paddle screen at Process 300 is sent to low Baumé liquefication 2 at Step 604 to continue soaking/cooking to soften the grit. The degerm operation can occur after high Baumé liquefication 1 at Step 103 of FIG. 6 or between high Baumé liquefication 1 at Step 103 and low Baumé liquefication 2 at Step 604, or after low Baumé liquefication 2 at Step 604.

The softened grit from liquefication 2 at Step 604 with low Baumé liquefied starch slurry fed to liquid/solid separation at Step 605 to dewater, followed by milling at Step 606 to break up the grit particles to release more starch. The slurry is then sent to liquid/solid separation and washing at Step 702 to produce pure fiber as feed stock for secondary alcohol production and paper industry use or sent to screen press at Step 708 for dewatering. It is then mixed with syrup from evaporator at Step 107 and sent to dryer at Step 108 to produce low protein DDGS for cow feed.

The whole stillage after fermentation at Step 104 and distillation at Step 105 is sent to decanter at Step 106 to recover high protein meal. The germ from degerm Process 1200 at Step 609 of FIG. 6 can further extract oil by combining screw press at Step 607 and solvent extraction at Step 608. The oil quality is better (light in color and low in free fatty acid). The oil yield can be as high as 1.6 lb/Bu, but the germ protein denatures in the high temperatures (over 1000° F.) used with this oil extraction, leading to a product with less nutritional value. Ethanol can be used as a solvent and an extremely high shear device such as a Supraton can be used to break the oil cell protein wall to produce good quality oil with high oil yield (up to 1.4 lb/bu) plus high value germ protein meal for fish farms.

Figure 8:
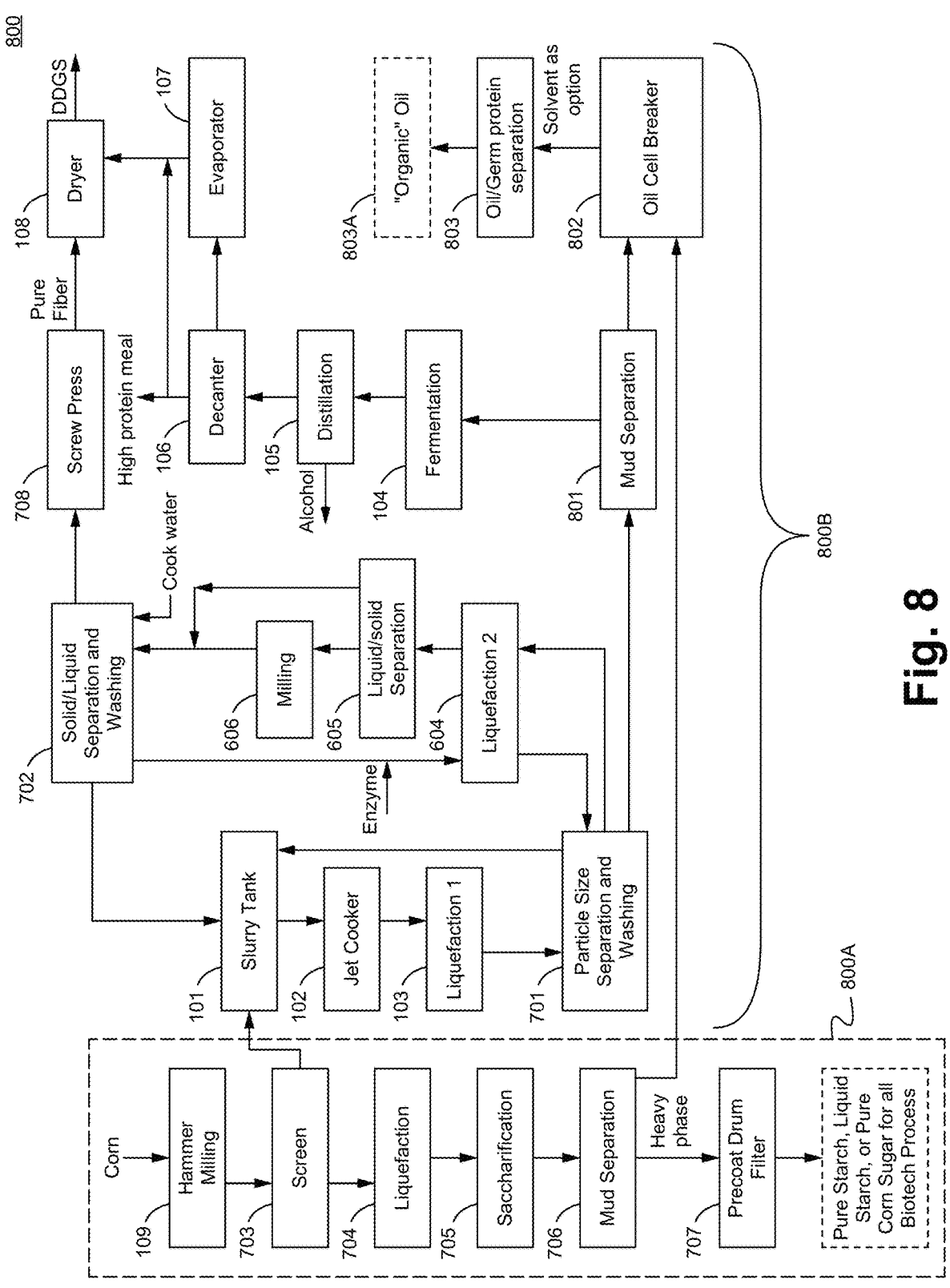
FIG. 8 illustrates an improved dry mill process to produce pure starch for biotech processes and produce pure fiber and "organic oil" before fermentation in accordance with some embodiments.

3) Process 800 of FIG. 8 illustrates an Improved Dry Mill Process with Removal of Fiber and Organic Oil Before Fermentation at Step 104 in Accordance with Some Embodiments.

The corn flour, after the hammer mill at Step 109, is sent to screen size separation at Step 703, to separate fine solids (mainly starch from the floury endosperm) from the coarse solids (mainly germ, grit and fiber). The fine solids portion is sent to liquefication at Step 704 and Saccharification at Step 705 to produce corn syrup, then sent to mud centrifuge at Step 706 to separate any oil/germ as a light (mud) phase. Next is precoat drum filter at Step 707 to remove any fine solids to produce clean pure corn syrup for biotech processes. The larger solid particles from screen separation at Step 703 are sent to slurry tank at Step 101 with filtrate from liquid/solid separation at Step 702 as cook water to start the liquefication steps by following jet cooker at Step 102 and liquefication 1 at Step 103 to liquefy the majority of the starch at higher temperatures (above 110° C.) and higher Baumé slurry.

The high Baumé liquefied starch slurry with grit, germ and fiber particles is sent to liquid/solid separation and washing at Step 701. The new three section paddle screen with small screen opening (e.g., 100 microns (can be 50 to 400 micron)) is used to separate and wash any larger solid particles (grit, germ, and fiber) to low Baumé liquefication 2 at Step 604. Further soaking/cooking grit, germ and fiber particles will become softer and easier to break up. The grit and germ particles, after soak/cooking in liquefication 2 at Step 604, are sent to liquid/solid separation at Step 605 for dewatering. Next comes milling at Step 606 to further break up the grit and germ particles to release starch and oil. The broken germ and grit particles are sent to other liquid solid separation and washing at Step 702 to produce pure fiber for secondary alcohol production or paper industry use or further dewatering by screw press at Step 708. Then, it is mixed with syrup from evaporator at Step 107 to produce low profat DDGS after dryer at Step 108. The cook water is used to wash the liquefied starch off the fiber in the $2^{nd}$ and $3^{rd}$ screen sections in the three section paddle screens apparatus before coming out as wet fiber cake.

The filtrate from the $2^{nd}$ and $3^{rd}$ section screen are recycled back to liquefication 2 at Step 604. The filtrate from $1^{st}$ section screen with small germ and grit particles are sent to slurry tank at Step 101. The high Baumé liquefied starch (filtrate from first section paddle screen at Step 701) is sent to mud centrifuge at Step 801 to remove mud (oil/germ/protein phase) before being sent to fermentation.

The whole stillage after fermentation at Step 104 and distillation at Step 105 is sent to decanter at Step 106 to produce high protein cake for animal feed and a portion is mixed with fiber to form high protein WDGS or DDGS. The overflow from decanter at Step 106 is sent to evaporator at Step 107 to concentrate to 30 to 35% DS syrup and mixed with fiber from screw press at Step 708 to produce DDGS. The overflow from decanter at Step 106 is back set.

The mud phase from both mud centrifuge at Step 801 and at Step 706 is sent to high shear milling device at Step 802 such as a Supraton to further break the oil cell wall inside the germ to release more oil. The breaking of the germ (germ protein) and oil are fed to a three-phase decanter at Step 803 to do oil/germ protein separation and produce "organic" oil as a light phase for human consumption. The germ protein, as the heavy phase from decanter is sent to fermentation at Step 104. A nontoxic solvent such hexane, butanol even ethanol can be added to decanter at Step 803 to increase oil yield, but this increases the need for more equipment (solvent recovery system) cost. If ethanol is used, the solvent recovery system can be part of distillation to save equipment cost and operation cost as well.

Figure 9:
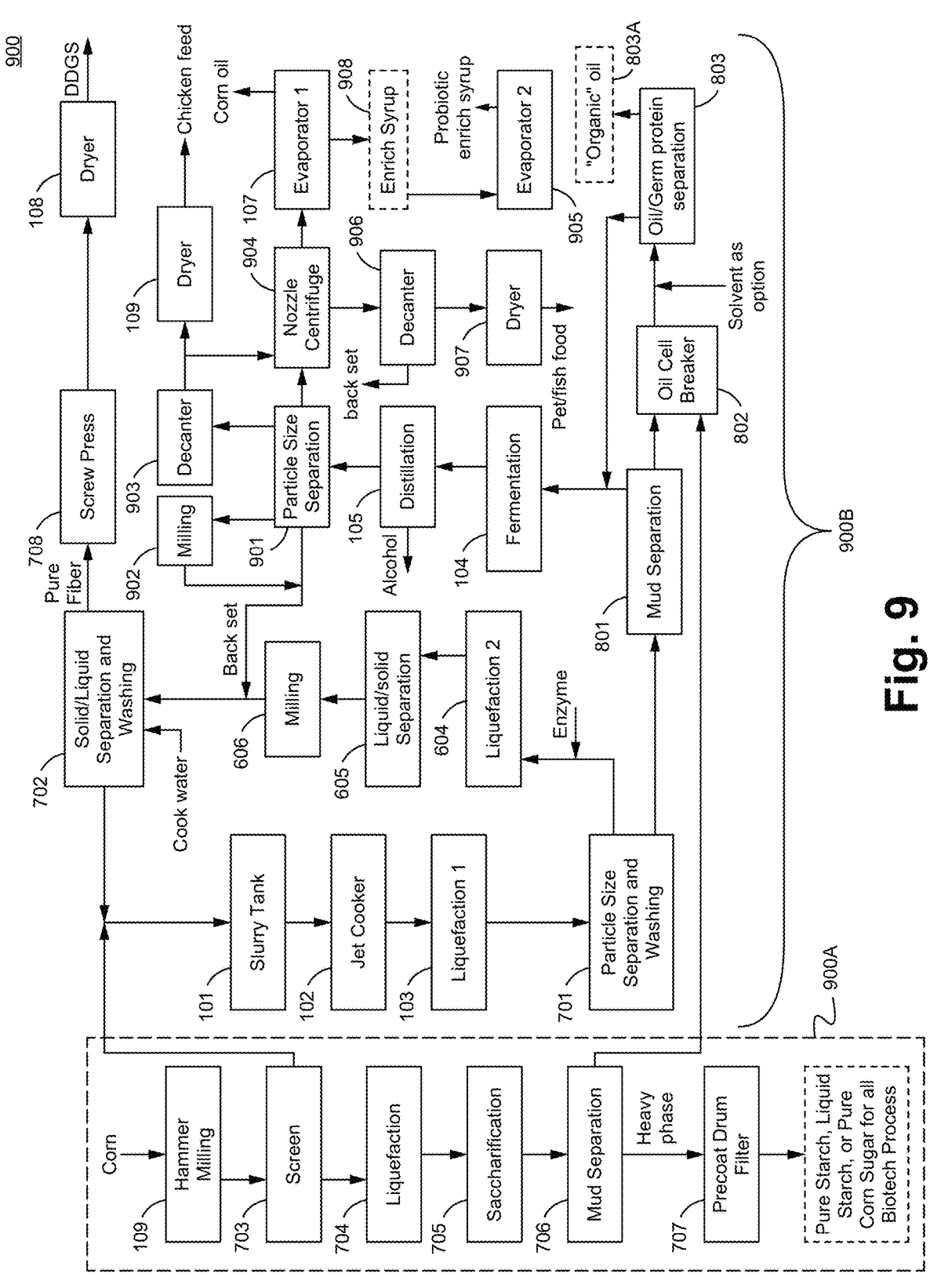
FIG. 9 illustrates an improved dry mill process to produce pure starch for biotech processes and produce pure fiber and "organic oil" before fermentation and animal feeds after fermentation in accordance with some embodiments.

4) Process 900 of FIG. 9 Illustrates an Improved Dry Mill Process Produce Pure Corn Syrup for Biotech Processes as Well as Remove Pure Fiber and Organic Oil Produced Before Fermentation and Produce Valuable Animal Feed Products from the Post Fermentation Process in Accordance with Some Embodiments.

After the hammer mill at Step 109, the corn flour is fed to screen size separation at Step 703 to separate fine solids, mainly the starch of the floury endosperm, from the coarse solids, which are mainly germ, grit, and fiber.

The fine solid portion is sent through liquefication at Step 704 and Saccharification at Step 705 to produce corn syrup. It is then sent to mud centrifuge at Step 706 to separate oil in the germ as the light (mud) phase, followed by precoat drum filter at Step 707 to remove any fine solids and produce clean pure corn syrup, which can be used for biotech processes. The larger solid particles from screen separation at Step 703 are sent to slurry tank at Step 101 with filtrate from liquid/solid separation at Step 702 used as cook water to start the liquefication step, followed by jet cooker at Step 102 and liquefication 1 at Step 103 to liquefy a majority of the starch at higher temperatures (above 110° C.) and higher Baumé slurry. The high Baumé liquefied starch slurry with grit, germ and fiber particles is sent to liquid/solid separation and washing at Step 701. The three-section paddle screen with small screen openings, e.g., 100 microns (can be 50 to 400 micron) separates and washes any larger solid particles (e.g., grit, germ and fiber) from low Baumé liquefication 2 at Step 604. The separated grit, germ and fiber particles are subjected to further soaking and cooking to become softer and easier to break up. The grit and germ particles, after soaking and cooking in liquefication 2 at Step 604 are sent to liquid/solid separation at Step 605 for dewatering, then to milling at Step 606 to further break up the grit and germ particles to release starch and oil.

The broken-up germ and grit particles are sent to liquid/solid separation and washing at Step 702 to produce pure fiber for secondary alcohol production or for the paper industry. They can be subjected to further dewatering by screw press at Step 708 to produce low profat DDGS after dryer at Step 108.

The cook water can be used to wash liquefied starch off the fiber in the 2$^{nd}$ and 3$^{rd}$ screen sections of the three-section paddle screen, before exiting as wet fiber cake. The filtrate from the 2$^{nd}$ and 3$^{rd}$ screen sections are recycled back to liquefication 2 at Step 604. The filtrate from the 1st screen section with small germ and grit particles is sent to slurry tank at Step 101. The high Baumé liquefied starch as filtrate from first section paddle screen at Step 701 is sent to the mud centrifuge at Step 801 to remove mud (e.g., the oil/germ/protein phase) before being sent to ferment.

The mud phase from both mud centrifuges at Steps 801 and 706 are sent to a high shear milling device at Step 802 such as a Supraton to further break the oil cell wall inside the germ particles to release more oil. The broken germ particles containing germ protein and oil are fed to a two or three phase decanter at Step 803 to perform an oil/germ protein separation and produce "organic" oil as a light phase for human consumption. The germ protein, as the heavy phase from decanter at Step 803, is sent to fermentation at Step 104. A solvent such hexane, butanol or ethanol can be added to the decanter at Step 803 to increase oil yield. However, this increases the need for more equipment (solvent recovery system) and increases cost. If ethanol is used, the solvent recovery system can be part of the distillation process to save equipment costs.

The whole stillage, after fermentation at Step 104 and distillation at Step 105 is sent to liquid/solid separation at Step 901 to separate any larger grit and germ particles and dewater the slurry before being sent to milling at Step 902. The further broken-up germ and grit particles from both milling at Step 606 and 902, plus the back set stream, are sent to liquid/solid separation at Step 702 and to a washing step and recycled back to the slurry tank at Step 101 for increased oil and alcohol yield. The filtrate from liquid/solid separation at Step 901 is sent to a decanter at Step 903 to produce high-protein meal wet cake, followed by a dryer at Step 109 to produce gluten meal for chicken and pig feed. The overflow from the decanter at Step 903 is sent to a nozzle centrifuge at Step 904 to separate an oil-rich stream as the light phase and a protein-rich stream as the heavy phase. The protein-rich heavy phase is sent to protein decanter at Step 906 to produce high-value yeast/germ protein wet cake follow by a ring dryer at Step 907 to produce high-value HP50 protein meal for household pet food and fish farm food. The overflow from decanter at Step 906 is back set. The oil rich light phase from nozzle centrifuge at Step 904 is sent to evaporator 1 at Step 107 to concentrate the liquid to 30 to 35% DS syrup. To recover the oil, this 30% DS syrup is sent to enrich syrup at Step 908 to convert resident sugar to lactic acid by addition of lactic acid producing probiotic cultures, such as *Lactobacillus plantarum* ZJ316, *Lactobacillus* amylovorus, *Lactobacillus fermentum*, or *Lactobacillus* mucosae. This secondary fermentation produces up to 20% (in DB) lactic acid and 10$^9$ CFU probiotic units.

This enriched syrup can be concentrated up to 85% DS syrup by a low temperature vacuum evaporator 2 at Step 905 to avoid high temperatures that can destroy the nutritional value inside the syrup. Alternatively, a waste heat recovery system (not shown) can be used to recover waste heat from the dryer to help evaporate the syrup to 85% DS. This high concentration syrup also can bypass the dryer and be added to super dry feed to maintain 10% moisture in the feed products. This 85% DS enriched syrup also can used as an animal food supplement or part of baby animal milk or as a bonding agent in production of probiotic pellet feed. The syrup can be added to animal drinking water formula.

The above improved dry mill processes are examples of many possible ways to use the larger grit, germ, and fiber particles as feedstock to produce alcohol and some by-products for animal feed. The selection of the specific process depends on the quality and quantity of pure starch needed plus the required alcohol yield and quality and the quality of the byproducts.

Many particle size reduction devices can used for milling at Steps 606 and 902, such as a grind mill (some shear force and some cutting); a roller mill (low energy and no cutting); a pin mill (no cutting, but impact force to break the particles); or a Supraton (highly intensive shear milling). The choice will depend on the quality and quantity of byproducts desired, plus the alcohol yield desired.

The three-section paddle screen with high-rate washing should be used for liquid/solid separation at Step 605 and particle size separation and washing at Steps 701, 702 and 901. The three sections of the screen can have different screen size openings, plus different screen designs and orientations (wedge wire slot opening vertical or parallel, round hole screen sheet, or wire screen etc.). Therefore, this device can be used for a very efficient solid classification by solid shape and size. For example, the device can separate fine fiber and germ particles with a wedge wire, with slot openings parallel to fluid flow, to receive the thin, long fiber particles. This device also gives extremely high rate of washing liquid to solid ratio (>1), replacement washing plus ease in selecting where to position the source of washing liquid.

Figure 13:
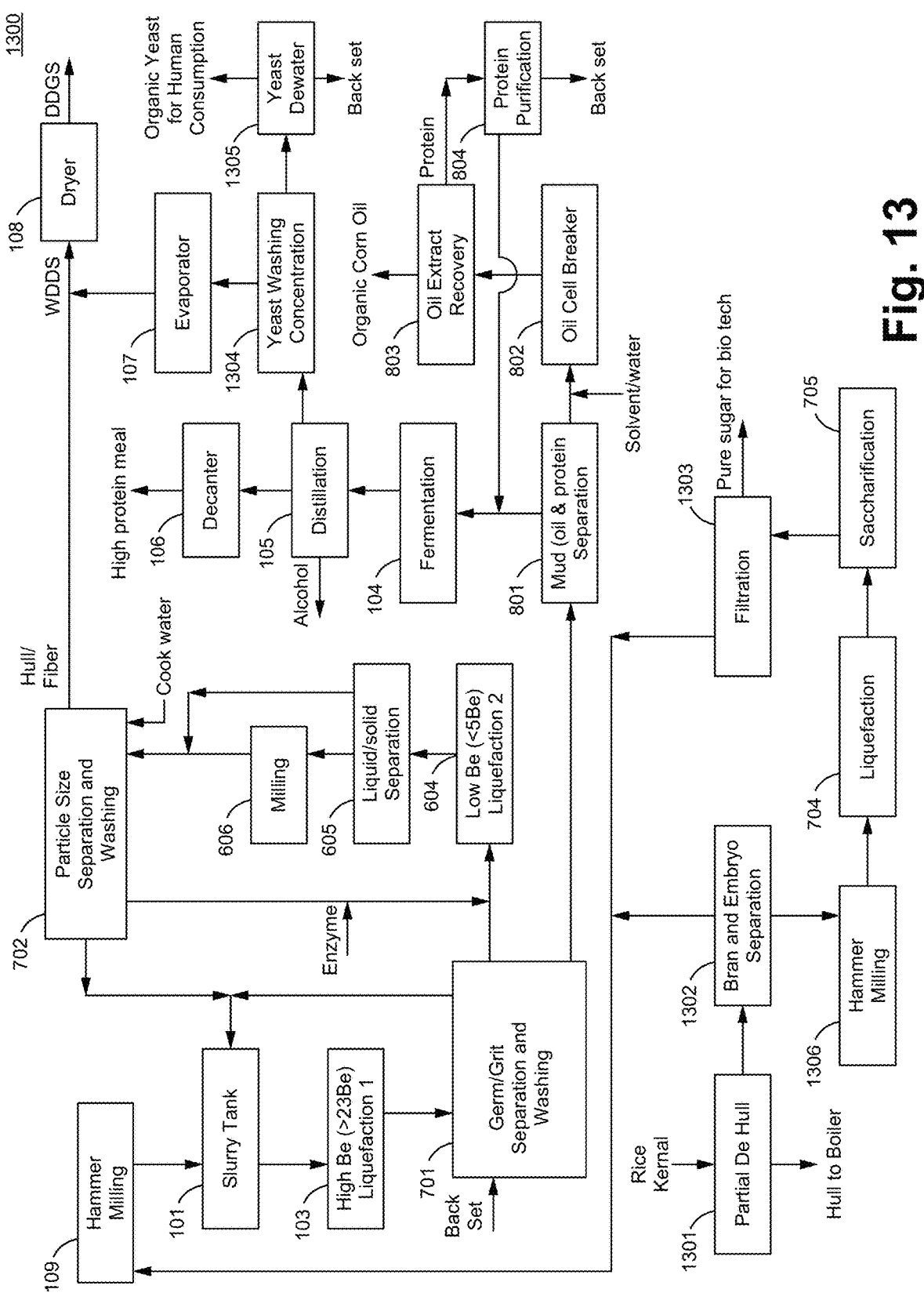
FIG. 13 illustrates a process for using partially dehulled brown rice to produce alcohol and pure starch for biotech processes, plus products including organic oil, rice protein and yeast protein for human consumption in accordance with some embodiments.

5) Process 1300 of FIG. 13 Illustrates Using Partially Dehulled Brown Rice to Produce Alcohol and Pure Starch, Organic Oil, Rice Protein and Yeast Protein for Human Consumption.

A feedstock of rice grains is fed to a partial dehulling device at Step 1301 to partially dehull the grains. The hull is not completely removed in this step. Some hull can be left with the grain, which contains the starch. The removed hull is sent to a boiler as a fuel source.

The starch and remaining hull particles are sent to bran and embryo separation at Step 1302 for bran and embryo separation. The bran and embryo are the protein and oil containing portions, respectively. To produce pure starch, the protein and oil containing portions need to be removed. The protein and oil free starch is sent to a hammermill at Step 1306. The milled rice starch is then sent to Step 704 for liquefaction, then Step 705 for saccharification, then Step 1303 to remove the pure starch for biotech applications. The bran and embryo separated during at Step 1302 are combined with fine fiber from Step 1303 and sent to Step 109 for milling. The rice flour, milled in a hammer mill at Step 109 is sent to a slurry tank at Step 101, and then liquefication at Step 103. After Step 103 liquefaction 1, the slurry is sent to Step 701. Back set is also added to Step 701.

The separated oil and protein containing portions are sent to a mud centrifuge at Step 801 to separate any oil/germ as a light (mud) phase, followed by a precoat drum filter at Step 802, to remove any fine solids.

The protein and oil containing particles are fed to a two or three phase decanter at Step 803 to separate the oil from the protein and produce "organic" oil as a light phase for human consumption. The germ protein comes off as the heavy phase from decanter at Step 803 and is sent to protein purification at Step 804. After the pure protein is removed, the liquid stream is sent to fermentation at Step 104. After fermentation at Step 104, the alcohol is sent to Step 105 for distillation for alcohol recovery. The stillage from distillation is sent to a yeast concentration at Step 1304. The concentrated yeast is dewatered at Step 1305 for organic yeast recovery for human consumption. The rejected water is used as backset. A solvent (such hexane, butanol, even ethanol) can optionally be fed to decanter at Step 802 to increase oil yield, but more equipment is needed (solvent recovery system). If ethanol is used, the solvent recovery system can be part of the ethanol distillation process to save equipment and operating cost. This step can produce clean pure corn syrup for biotech processes. The larger solid particles from screen separation at Step 701 are sent to slurry tank at Step 101 with filtrate from liquid/solid separation at Step 702. The high Baumé liquefied starch slurry with grit, germ and fiber particles is sent to liquid/solid separation and washing at Step 701.

The three-section paddle screen with small screen openings in the first section (e.g., 100 microns, or between 50 to 400 microns) should be used to separate and wash any larger solid particles (grit, germ and fiber). These particles can be added to low Baumé liquefaction 2 at Step 604. Further soaking and cooking of the grit, germ and fiber particles cause them to become softer and easier to break up. The grit and germ particles, after soaking and cooking in liquefication 2 at Step 604 are sent to liquid/solid separation at Step 605 for dewatering, then to milling at Step 606 to further break up the grit and germ particles to release starch and oil. This breakup of germ and grit particles is sent to other liquid solid separation and washing at Step 702. The broken particles are combined with the stream after evaporator at Step 107 and are sent to the dryer in at Step 108 to produce DDDS. The cook water is used for washing the liquefied starch off the fiber in the $2^{nd}$ and $3^{rd}$ screen sections in the three-section paddle screen device before coming out as wet fiber cake. The filtrate from the $2^{nd}$ and $3^{rd}$ screen sections is recycled back to liquefication 2 at Step 604. The filtrate from the 1st screen section with small germ and grit particles is sent to slurry tank at Step 101. The high Baumé liquefied starch as filtrate from the first section of the paddle screen at Step 701 is sent to mud centrifuge at Step 801 to remove mud (oil/germ/protein phase) before being sent to fermentation.

The mud phase from both mud centrifuges at Steps 801 and 706 are sent to high shear milling device at Step 802 such as a Supraton, to further break the oil cell wall inside the germ to release more oil.

This invention can apply to all types of grain such as sorghum, wheat, barley, millet and rice etc in addition to corn.

Process Variations

Figure 18:
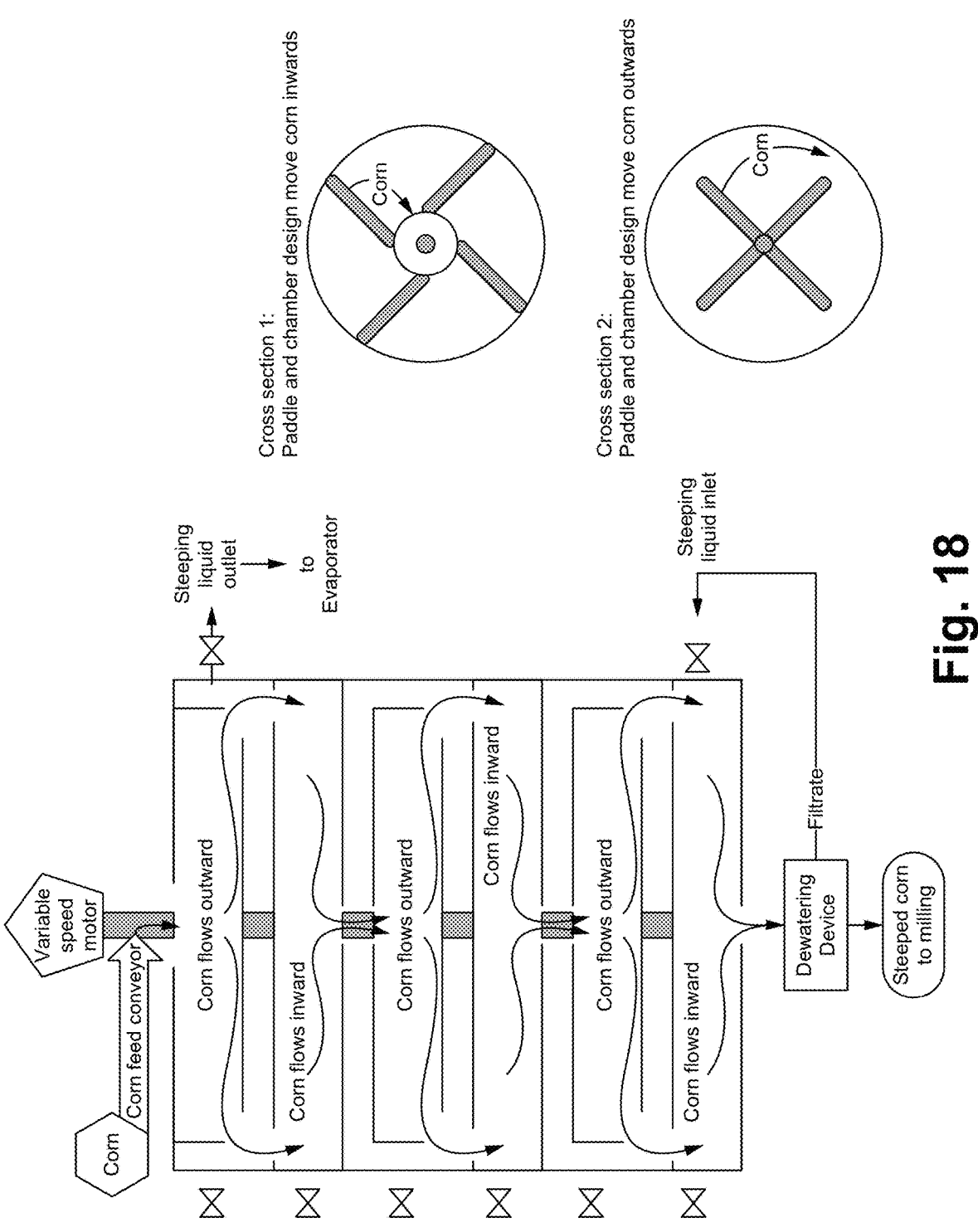
FIG. 18 illustrates a continuous steeping tank in accordance with some embodiments.

FIG. 18 illustrates a continuous steeping tank in accordance with some embodiments. In some embodiments, this large steeping tank has approximately equivalent height and diameter. The steeping tank contains horizontal divisions which separate the larger tank into multiple chambers. Each chamber has opening(s) either close to the tank wall or in the center. The type of opening for each chamber is the opposite of the type in the chamber above it, creating an alternating pattern. Each chamber contains paddles that move corn towards the openings, of a different design depending on whether the corn is moving towards the edge openings or the center opening. The paddles are connected to a central shaft which in turn is connected to a variable speed motor which controls the corn steeping time by adjusting the amount of time the corn remains in each chamber.

Figure 19A:
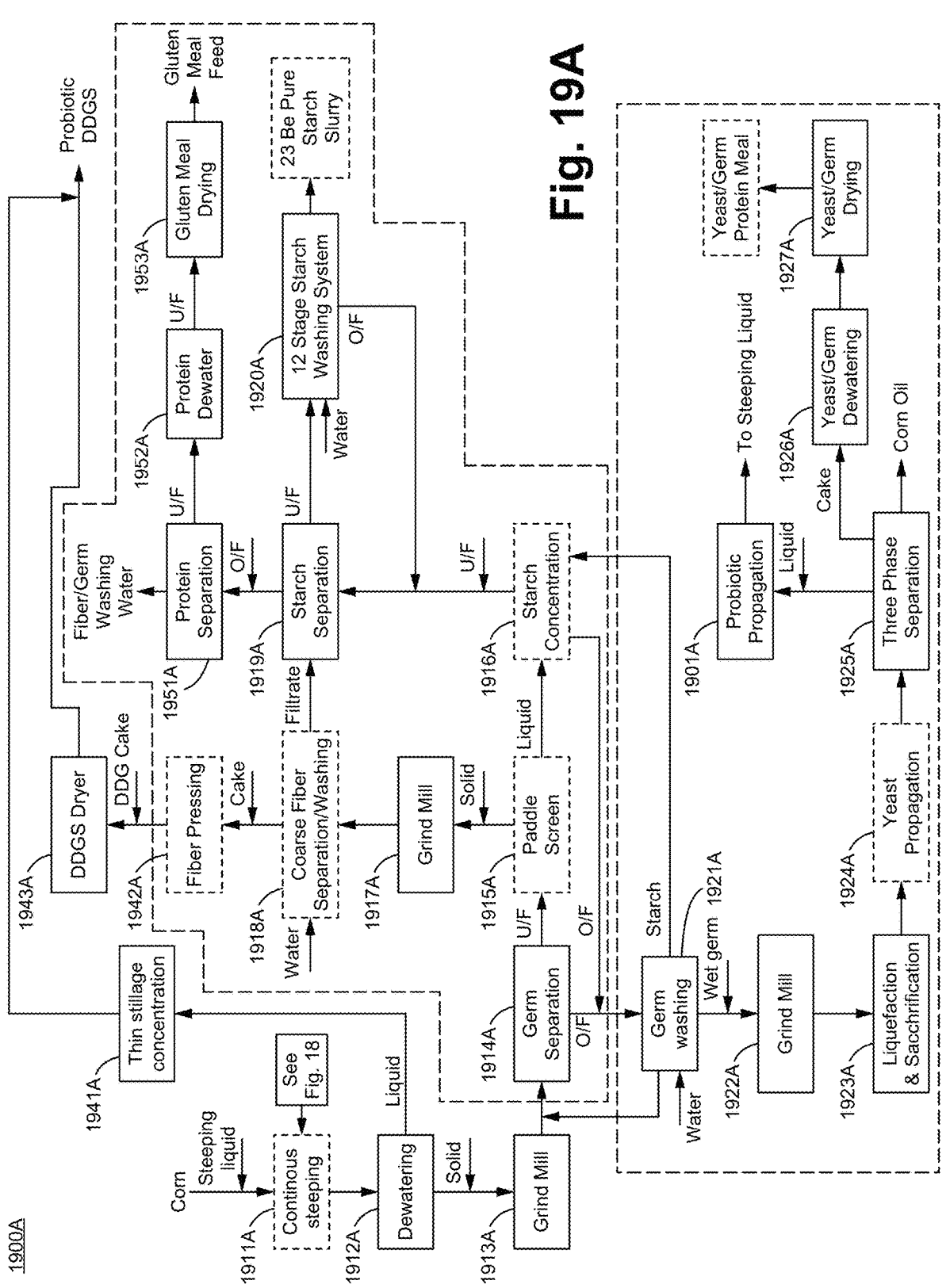
FIG. 19A illustrates an improved wet mill process that produces maximum pure starch and high value germ and yeast protein meal in accordance with some embodiments.

FIG. 19A illustrates a wet mill process 1900A producing maximum pure starch slurry, high value germ, and yeast protein meal in accordance with some embodiments.

Process 1900 improves upon a typical wet mill process with the following changes including (1) replacing the current 6-8 batch steeping tanks with one continuous steeping tank, to cut capital costs and simplify operations, (2) installing a multi-section paddle screen to wash starch off fiber and produce low starch fiber, (3) installing a solid ring design grind mill to grind wet germ particles to less than 50 microns to release oil and produce germ protein, (4) producing a pure starch slurry from the starch in the floury endosperm with very low soluble proteins, suitable for use in many new green technology processes, (5) converting the starch from the horny endosperm, which is bound with fiber and protein, into a sugar solution and using this low Baumé sugar solution to produce yeast cells as aqua feed, (6) increasing lactic acid in steeping liquid by adding probiotic cultures to cut steeping time and produce probiotic feed, and (7) producing a high nutrient DDGS with low oil and low starch content for cattle feed.

Detailed Steps of Process 1900

At Step 1911A of continuous steeping, corn kernels enter the process and are immersed in liquid in a continuous steeping process, which is illustrated in the system of FIG. 18. (A batch steeping process is the typically used alternative.) Corn starts at 10% moisture and increases to 45% to 50% moisture by weight at the end of this step.

At Step 1912A of dewatering, free water is separated from the swollen corn kernels.

At Step 1913A of a grind mill for $1^{st}$ milling, a grind mill or other milling device tears the kernels apart to release the starch from the floury endosperm only. LeeTech's patented solid ring design grind mill (U.S. Pat. No. 9,352,326) is suitable for this step, as it enables greater control over the level of grinding, and is incorporated by reference for all purposes.

At Step 1914A of germ separation, a germ cyclone (as most commonly used) or other separation device separates the germ from the starch slurry.

At Step 1915A of a paddle screen for liquid/solid separation, a paddle screen or other separation device separates the mixture, which contains starch from the floury endosperm, grit, and germ with 90% moisture, into two streams: one stream with liquid and starch, and the other stream contains germs and grit with 80% moisture and no free starch. LeeTech's patented paddle screen (U.S. Pat. No. 9,718,006) is suitable for this step, and is incorporated by reference for all purposes.

At Step 1916A of starch concentration, a cyclone concentrator creates two flows of starch slurry. The incoming starch slurry contains 10-13° Baumé starch. After the cyclone concentrator, the underflow contains 23° Baumé starch and the overflow contains 5-7° Baumé starch. Using a cyclone concentrator lessens the capacity needed for the primary centrifuge in the subsequent starch processing step (Step 1919A), saving energy consumption over exclusive use of a centrifuge.

At Step 1917A of a grind mill for 2nd milling, a grind mill or other mill breaks up the remaining germ and grit from the horny endosperm, which contains starch bound with protein, oil and fiber. LeeTech's patented solid ring design grind mill (U.S. Pat. No. 9,352,326) is suitable for this step, which is incorporated by reference for all purposes.

At Step 1918A of coarse fiber separation/washing, a paddle screen or other screen separation device with different screen size washes the fiber (from the pericap and tip cap) clean of starch, protein, oil. LeeTech's patented paddle screen (U.S. Pat. No. 9,718,006) is suitable for this step, and is incorporated by reference for all purposes.

At Step 1919A of starch separation, a primary centrifuge separates the starch from the protein. The starch in the underflow is directed into the 12-stage starch washing system and the protein in the overflow is directed to the clarifier centrifuge (see step 1951A).

At Step 1920A of 12-stage starch washing, a countercurrent washing system reduces the protein content of the slurry from 4% to less than 0.4% protein (and including only 0.1% soluble protein), creating a pure starch slurry.

At Step 1921A of germ washing, after the germ separation (Step 1914A), the germ is washed to separate any remaining starch. That starch is directed to the cyclone concentrator (Step 1916A), while the germ proceeds to milling (Step 1922A).

At Step 1922A of a grind mill for germ particle size reduction, a grind mill or other milling device reduces the particle size of the germ particles to less than 50 microns, breaking the bonds between the oil, protein and starch. LeeTech's patented solid ring design grind mill (U.S. Pat. No. 9,352,326) is suitable for this step, and is incorporated by reference for all purposes.

At Step 1923A of liquefaction and saccharification, starch in the germ is converted into shorter chains and then converted to sugar (glucose).

At Step 1924A of yeast propagation, yeast is permitted to consume some sugar to propagate but not enough to produce significant quantities of alcohol.

At Step 1925A of three-phase separation, a three-phase decanter is used for separating the mixture into 3 phases. The oil phase yields corn oil suitable for biodiesel (but less suitable for human consumption due to high free-fatty-acid consent). The solid phase contains a cake of yeast and germ protein. The liquid phase includes water and soluble with minimal oil, alcohol, and protein.

At Step 1901A of probiotic propagation, the probiotics in this aqueous mixture are allowed to propagate and the resulting liquid then is used as part of the original steeping liquid for the corn in the first step of the process (Step 1911A).

At Step 1926A of yeast/germ dewatering, the solid phase which contains yeast and germ protein in a cake is dewatered to reduce moisture from 75% to 65% using a vacuum drum filter, plate & frame filter, press, filtration device or other dewatering equipment.

At Step 1927A of yeast/germ drying, a dryer reduces the moisture content of the mixture to 10% to produce a yeast/germ protein meal that is a high value aquafeed.

At Step 1941A of thin stillage concentration, after the initial dewatering (Step 1912A), a nozzle centrifuge concentrates the dewatering liquid to a clean thin stillage syrup (70% or more dry solids). The probiotic syrup can be used as a binding agent to produce enriched probiotic DDGS tablets.

At Step 1942A of fiber pressing, a fiber press reduces moisture in the cake from 80% to 60% moisture.

At Step 1943A of DDGS drying, a dryer further dries the cake, which is then combined with the probiotic syrup from Step 1941A, to create probiotic DDGS tablets for cattle feed.

At Step 1951A of protein separation, after the primary centrifuge (Step 1919A), the protein and water in the overflow goes into the clarifier centrifuge or other separation device which separates water from protein. The overflow water can be used for germ washing (Step 1921A) and fiber washing (Step 1918A).

At Step 1952A of protein dewatering, the protein is further dewatered using vacuum filtration or a plate and frame filter to produce 40% dry solids (DS) or a decanter to produce 35% dry solids.

At Step 1953A of gluten meal drying, a dryer (e.g., usually a rotary dryer) is used to further reduce moisture and create gluten meal feed with 50-60% protein content.

For succinctness, the rest of Steps that are already provided in the figure are not further described and are able to be performed using ordinary processes.

Figure 19B:
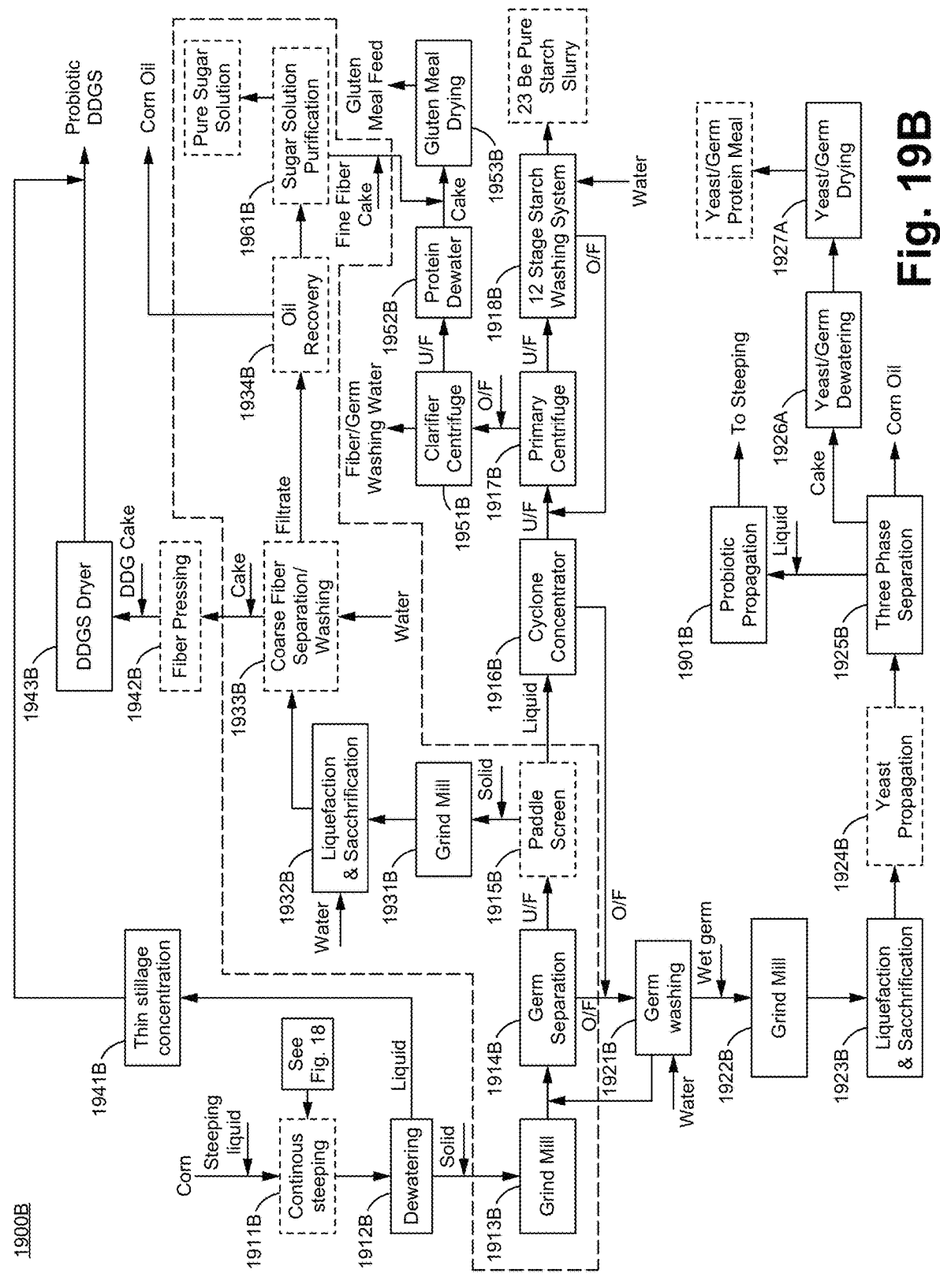
FIG. 19B illustrates an improved wet mill process that produces pure starch, germ/yeast protein meal, and pure sugar in accordance with some embodiments.

FIG. 19B illustrates an improved wet mill process 1900B producing pure starch, yeast/germ protein meal, and a sugar solution in accordance with some embodiments. This variation further improves upon the typical wet mill process beyond the changes shown in Process 1900A of FIG. 19A by producing a sugar solution with higher soluble protein from the starch bound with protein in the horny endosperm. In the following, the key variation processes are illustrated.

At Step 1932B of liquefaction & saccharification, after the second milling (Step 1931B) and before the coarse fiber separation (Step 1933B), starch from the horny endosperm is liquefied and converted into sugars.

At Step 1934B of oil recovery, after coarse fiber separation (step 1933B), a centrifuge is used to separate the corn oil from the liquified starch.

At Step 1961B of sugar solution purification, a centrifuge, filtration device or desludger centrifuge separates the sugar solution from the fine fiber cake (which is directed to the gluten meal dryer (Step 1953B).

For succinctness, the rest of Steps that are already provided in the figure are not further described and are able to be performed using ordinary processes or the process described in 1900A.

Figure 19C:
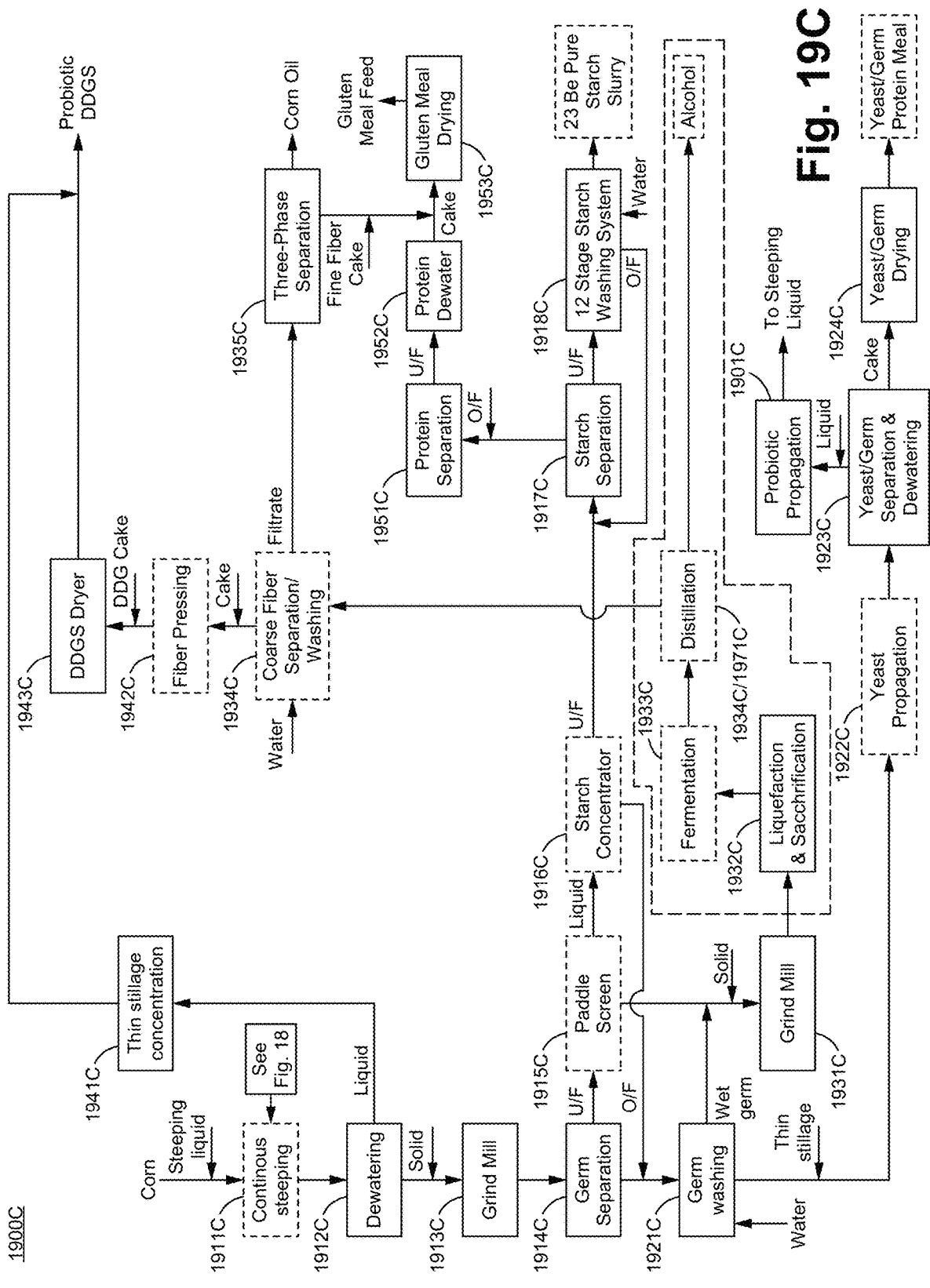
FIG. 19C illustrates an improved wet mill process that produces pure starch, germ/yeast, protein meal and alcohol in accordance with some embodiments.

FIG. 19C illustrates an improved wet mill process 1900C producing pure starch, yeast/germ protein meal and alcohol in accordance with some embodiments.

This variation further improves upon the typical wet mill process beyond the changes shown in FIG. 19A by producing alcohol (typically ethanol, but possibly a higher carbon alcohol such as propanol) from the starch bound with protein and fiber in the horny endosperm (instead of the sugar solution in FIG. 19B). In the following, the key variation processes are illustrated.

At Step 1933C of fermentation, after the starch from the horny endosperm has been liquefied and saccharified (e.g., at Step 1932C), yeast is added. The yeast converts the sugar solution into alcohol.

At Step 1934C/1971C of distillation, a distillation tower or other method of distillation collects the alcohol. The remaining oil and fiber (e.g., whole stillage) is directed to the coarse fiber separation/washing (Step 1934C).

For succinctness, the rest of Steps that are already provided in the figure are not further described and are able to be performed using ordinary processes or the process described in 1900A.

Figure 19D:
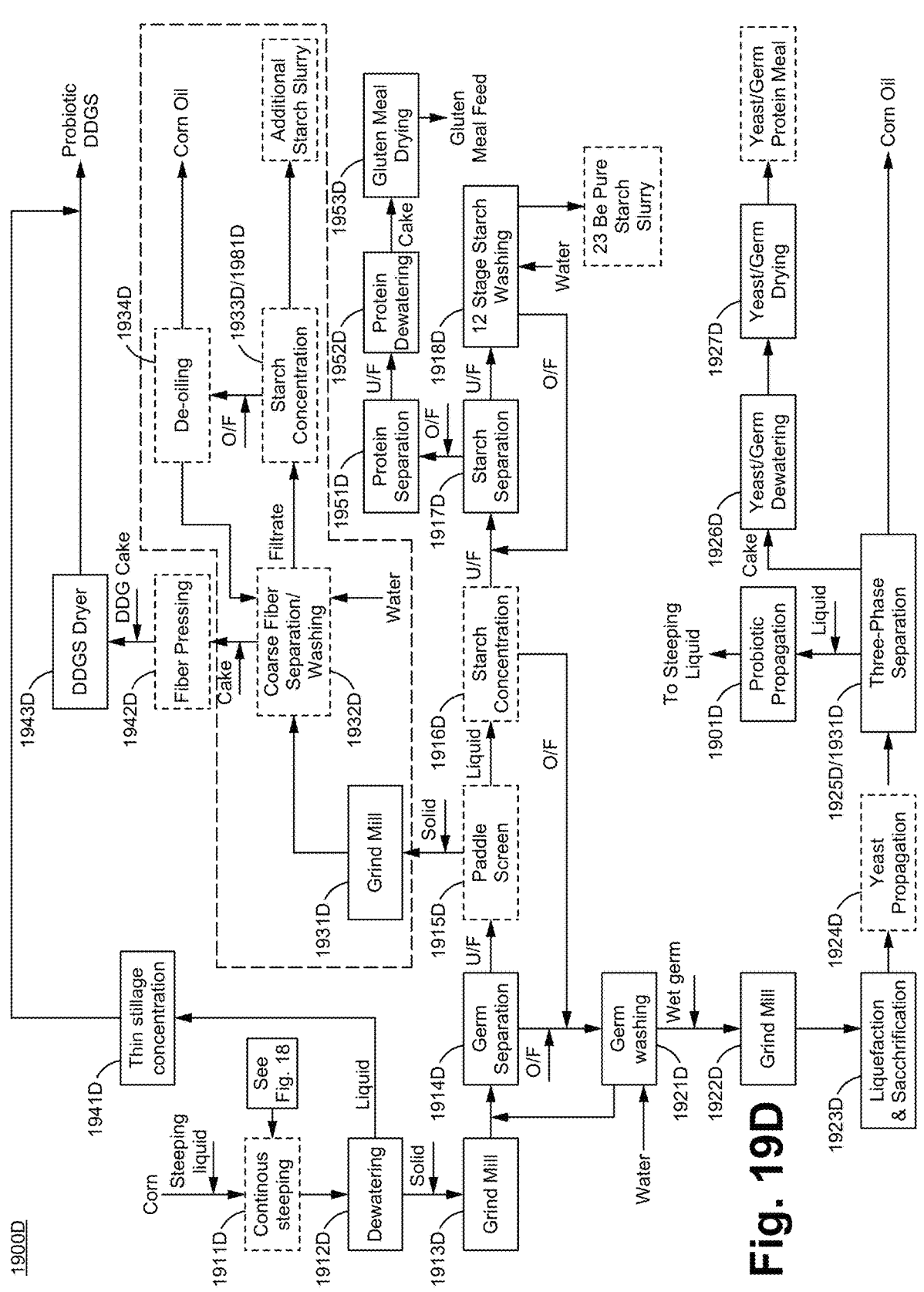
FIG. 19D illustrates an improved wet mill process that produces pure starch, germ/yeast protein meal, and additional pure starch in accordance with some embodiments.

FIG. 19D illustrates an improved wet mill process 1900D producing pure starch, yeast/germ protein meal, and additional starch in accordance with some embodiments.

This variation further improves upon the typical wet mill process beyond the changes shown in the FIG. 19A by producing additional pure starch from the starch bound with protein and fiber in the horny endosperm (instead of the sugar solution in the FIG. 19B or alcohol in the FIG. 19C). In the following, the key variation processes are illustrated.

After the grind mill in Step 1931D, the slurry goes directly to the coarse fiber separation & washing (Step 1932D) instead of going through liquefaction, saccharification and fermentation first.

At Step 1933D/1981D of starch concentration, after coarse fiber separation and washing, the filtrate is directed to a cyclone concentrator that separates another starch slurry (underflow) from oil (overflow).

At Step 1934D of de-oiling, the oil is separated from fine fiber to produce corn oil.

For succinctness, the rest of Steps that are already provided in the figure are not further described and are able to be performed using ordinary processes or the process described in 1900A.

Figure 19E:
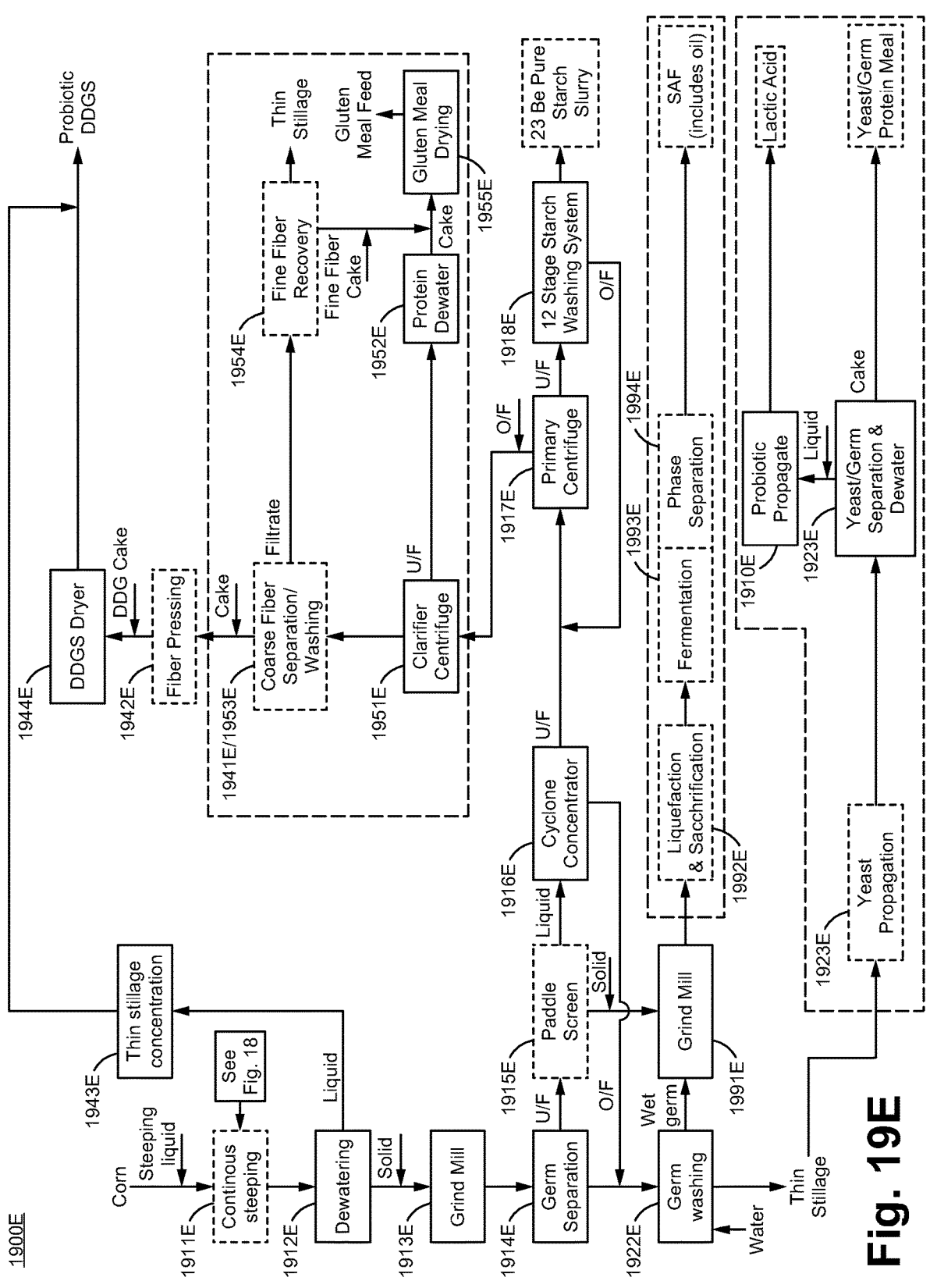
FIG. 19E illustrates an improved wet mill process that produces pure starch, germ/yeast protein meal, lactic acid, and an alcohol for sustainable aviation fuel (SAF) such as butanol in accordance with some embodiments.

FIG. 19E illustrates an improved wet mill process 1900E producing pure starch, yeast/germ protein meal, lactic acid, and sustainable aviation fuel (SAF, such as butanol or other alcohol) in accordance with some embodiments.

This variation further improves upon the typical wet mill process beyond the changes shown in FIG. 19A by converting the sugar solution from all the starch bound with protein and fiber in the horny endosperm into an alcohol that can be a bio-based sustainable aviation fuel through fermentation and phase separation. In the following, the key variation processes are illustrated.

At Step 1992E of liquefaction & saccharification, after the horny endosperm has been milled, the starch is liquefied and saccharified.

At Step 1993E of fermentation, a culture is added. The culture converts the sugar solution into an alcohol, such as butanol.

At Step 1994E of phase separation, a separation device, such as an incline plate gravity, separates the sustainable aviation fuel (e.g., butanol) from the water, which stays in the fermenter. (e.g. the butanol, with 4 carbons, does not dissolve in water so stays with the oil.)

At Step 1910E, after the probiotic propagation step, the resulting lactic acid can become a co-product itself, usable as a non-toxic, bio-based insecticide.

At Step 1954E of fine fiber recovery, after the coarse fiber separation & washing, the fine fiber is recovered from the thin stillage and the cake added into the gluten meal dryer (Step 1955E.)

For succinctness, the rest of Steps that are already provided in the figure are not further described and are able to be performed using ordinary processes or the process described in 1900A.

Figure 20A:
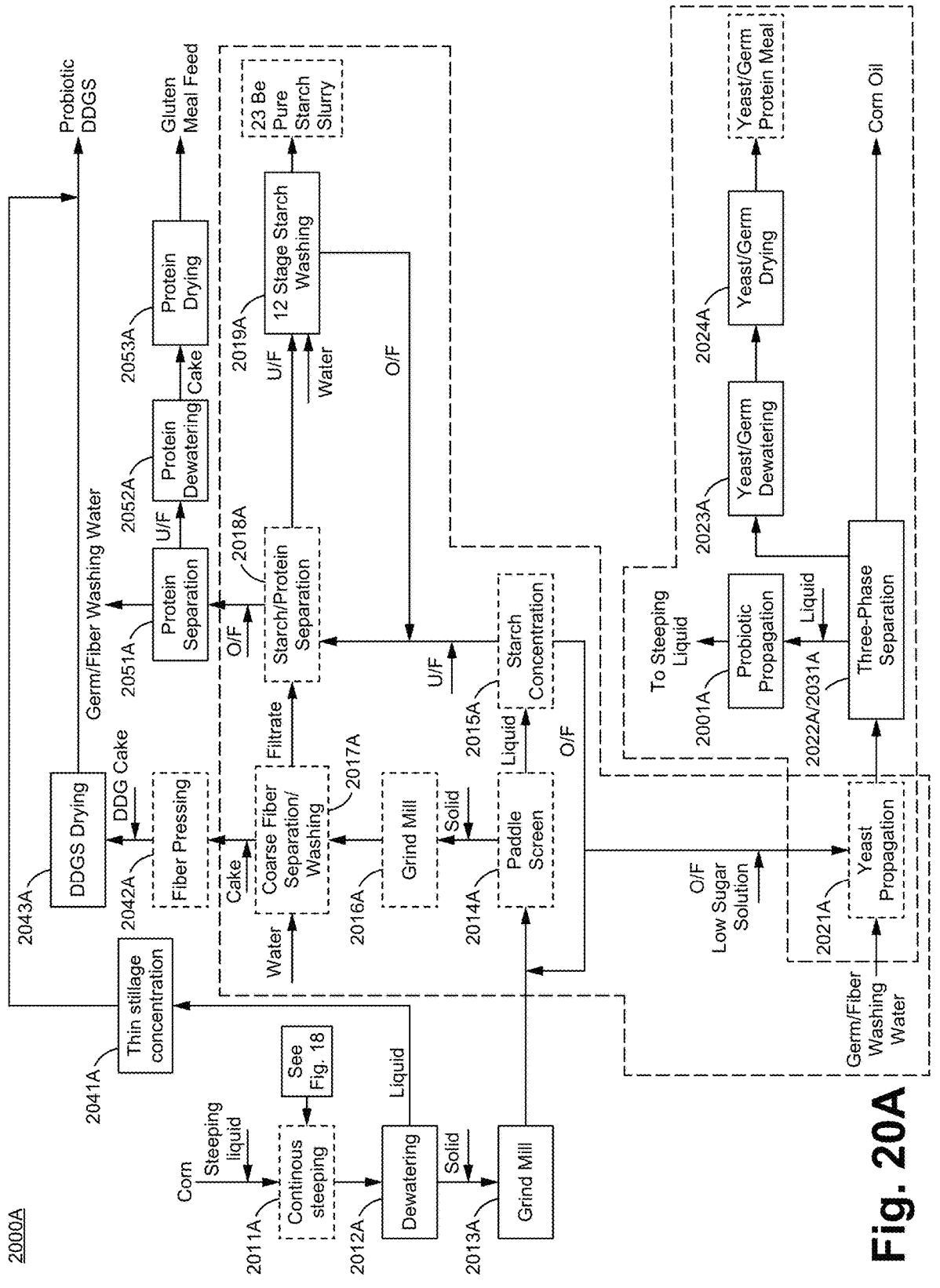
FIG. 20A illustrates a wet mill process that produces maximum pure starch, gluten meal feed, yeast/germ protein meal in accordance with some embodiments.

FIG. 20A illustrates a wet mill process 2000A producing maximum amount of pure starch and yeast/germ protein meal in accordance with some embodiments. Process 2000A includes features of reducing the required capital investment for a new wet mill, simplifying operations, and producing corn oil without toxic solvents while producing high-value yeast/germ protein as aquaculture feed. In the following, the key variation processes are illustrated.

At Step 2011A of steeping, corn enters the process and is steeped in either a batch or continuous steeping process. Corn starts at 10% moisture and increases to 50% moisture by weight.

At Step 2012A of dewatering, free water is separated from the swollen corn kernels.

At Step 2013A of a grind mill for a $1^{st}$ milling, a grind mill or other milling device tears the kernels apart to release the starch from the floury endosperm only. LeeTech's patented solid ring design grind mill (U.S. Pat. No. 9,352,326) is suitable for this step, as it enables greater control over the level of grind, and is incorporated by reference for all purposes.

At Step 2014 of a paddle screen for liquid/solid separation, a paddle screen or other separation device separates the mixture (which contains starch from the floury endosperm, grit, and germ with 90% moisture) into two streams: one with liquid and starch, and the other germ and grit with 80% moisture (and no free starch) LeeTech's patented paddle screen (U.S. Pat. No. 9,718,006) would be suitable for this step, and is incorporated by reference for all purposes.

At Step 2015A of starch concentration, a cyclone concentrator creates two flows of starch slurry. The incoming starch slurry contains 10-13° Baumé starch. After the cyclone concentrator, the underflow contains 23° Baumé starch and is directed to a primary centrifuge (Step 2018A). The overflow contains 5-7° Baumé starch with germ protein; a portion of this flow is directed back to the paddle screen (Step 2014A) and part towards the yeast/germ protein meal and corn oil production flow, specifically yeast propagation (Step 2021). Using a cyclone concentrator lessens the capacity needed for the primary centrifuge in the subsequent starch processing step (Step 2018A), saving energy consumption over exclusive use of a centrifuge.

At Step 2016A of a grind mill for a $2^{nd}$ milling, a grind mill or other mill breaks up the remaining germ and grit from the horny endosperm (which contains starch bound with protein, oil and fiber). LeeTech's patented grind mill (U.S. Pat. No. 9,352,326) is suitable for this step, and is incorporated by reference for all purposes.

At Step 2017A of coarse fiber separation & washing, a paddle screen or other screen separation device with different screen size washes the coarse fiber (from the pericap and tip cap) clean of starch, protein, oil. LeeTech's patented paddle screen (U.S. Pat. No. 9,718,006) is suitable for this step, and is incorporated by reference for all purposes.

At Step 2018A of starch/protein separation, the input to this step comes from both the coarse fiber separation and washing paddle screen (Step 2017A) and the starch concentration cyclone concentrator (Step 2015A). A primary centrifuge separates the protein from the starch. The starch in the underflow is directed into the 12-stage starch washing system and the protein in the overflow is directed to the clarifier centrifuge (see Step 2051A).

At Step 2019A, 12-stage starch washing: counter-current washing reduces the protein content of the slurry from 4% to less than 0.4% protein (and including only 0.1% soluble protein), creating a pure starch slurry. The overflow containing protein is directed back to the primary centrifuge (Step 2018A).

At Step 2021A of yeast propagation, the overflow from the starch concentrator which contains protein and starch after separation from pure starch (Step 2015A), along with the germ/fiber washing water containing some germ after separation from protein (Step 2051A), or other low sugar solution (a waste product readily available from other parts of the process) are combined with a yeast culture, which propagates but stops short of fermentation.

At Step 2022A/2031A of three-phase separation, a three-phase decanter is used for separating the mixture into 3 phases. The oil phase yields corn oil suitable for biodiesel (but less suitable for human consumption due to high free-fatty-acid content). The solid phase contains a cake of yeast and germ protein. The liquid phase includes water and soluble with minimal oil, alcohol, and protein.

At Step 2001A of probiotic propagation, the probiotics in the liquid phase from Step 2022A/2031A are allowed to propagate and the resulting liquid then is used as part of the original steeping liquid for the corn in the first step of the process, Step 2011A.

At Step 2023A of yeast/germ dewatering: the solid phase which contains yeast and germ protein in a cake is dewatered to reduce moisture from 75% to 65% using a vacuum drum filter, plate & frame filter, press, filtration device or other dewatering equipment.

At Step 2024A of yeast/germ drying, a dryer reduces the moisture content of the mixture to 10% to produce a yeast/germ protein meal that is a high value aquafeed.

At Step 2041A of thin stillage concentration, after the initial dewatering (Step 2012A), a nozzle centrifuge concentrates the dewatering liquid to a clean thin stillage syrup (70% or more dry solids). The probiotic syrup can be used as a binding agent to produce enriched probiotic DDGS tablets.

At Step 2042A of fiber pressing, the cake from coarse fiber separation/washing (Step 2017A) is subjected to a fiber press which reduces moisture in the cake from 80% to 60% moisture.

At Step 2043A of DDGS drying, the cake from the fiber press is combined with syrup from the evaporator (Step 2041A); a dryer dries the syrup/cake mixture into probiotic DDGS for cattle feed.

At Step 2051A of protein separation, after the primary centrifuge (Step 2018A), the protein and water in the overflow goes into the clarifier centrifuge or other separation device which separates water from protein. The overflow water, which contains some germ, is directed to the germ and corn oil production process (starting with Step 2021A).

At Step 2052A of protein dewatering, the water in the mixture is further reduced.

At Step 2053A of gluten meal drying, a dryer is used to further reduce moisture and create gluten meal feed with 50-60% protein content. For succinctness, the rest of Steps that are already provided in the figure are not further described and are able to be performed using ordinary processes.

Figure 20B:
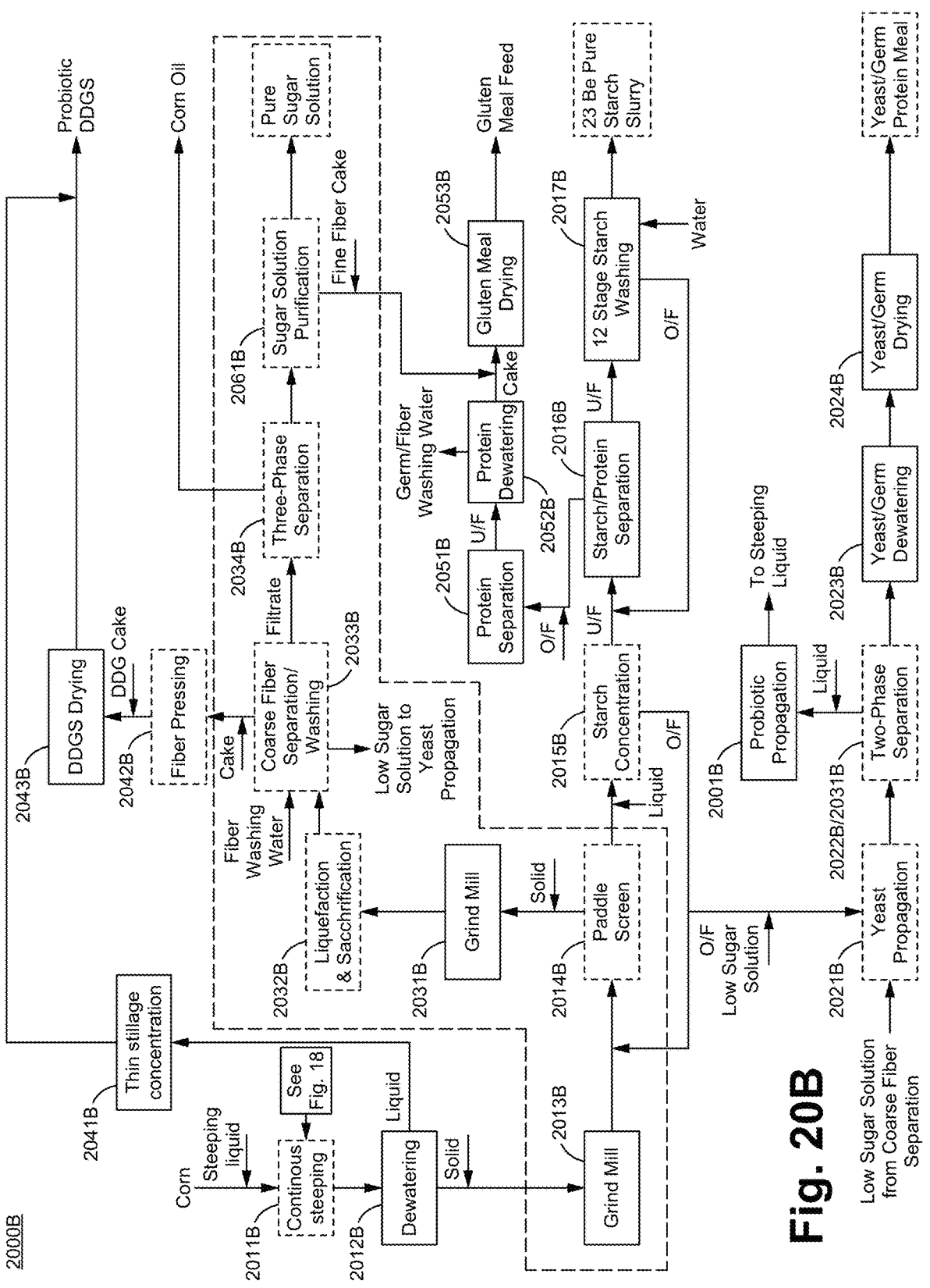
FIG. 20B illustrates a wet mill process that produces pure starch, sugar solution, gluten meal feed, and yeast/germ protein meal in accordance with some embodiments.

FIG. 20B illustrates a wet mill process producing pure starch, yeast/germ protein meal, and sugar solution in accordance with some embodiments. This variation builds on the features in FIG. 20A and also produces a sugar solution with higher soluble protein from the starch bound with protein in the horny endosperm. In the following, the key variation processes are illustrated.

At Step 2032B of liquefaction and saccharification, after the second milling (Step 2031B) and before the coarse fiber separation (Step 2033B), starch is liquefied.

At Step 2033B of coarse fiber separation/washing, some of the fiber washing liquid, a low-sugar solution, is directed towards the yeast propagation step (Step 2021B) in the yeast/germ protein meal and corn oil process.

At Step 2034B of three-phase separation, after coarse fiber separation (step 2033B), a three-phase decanter or other three-phase separation equipment is used to separate the corn oil from the liquified starch.

At Step 2061B of sugar solution purification, a centrifuge, filtration device or de-sludger centrifuge separates the pure sugar solution from the fine fiber cake, which is directed towards the gluten meal drying step.

At Step 2022B/2031B of two-phase separation, the oil from the germ has been captured elsewhere in the process, thus this step is a two-phase separation not a three-phase separation.

For succinctness, the rest of Steps that are already provided in the figure are not further described and are able to be performed using ordinary processes or the process described in 1900A.

Figure 20C:
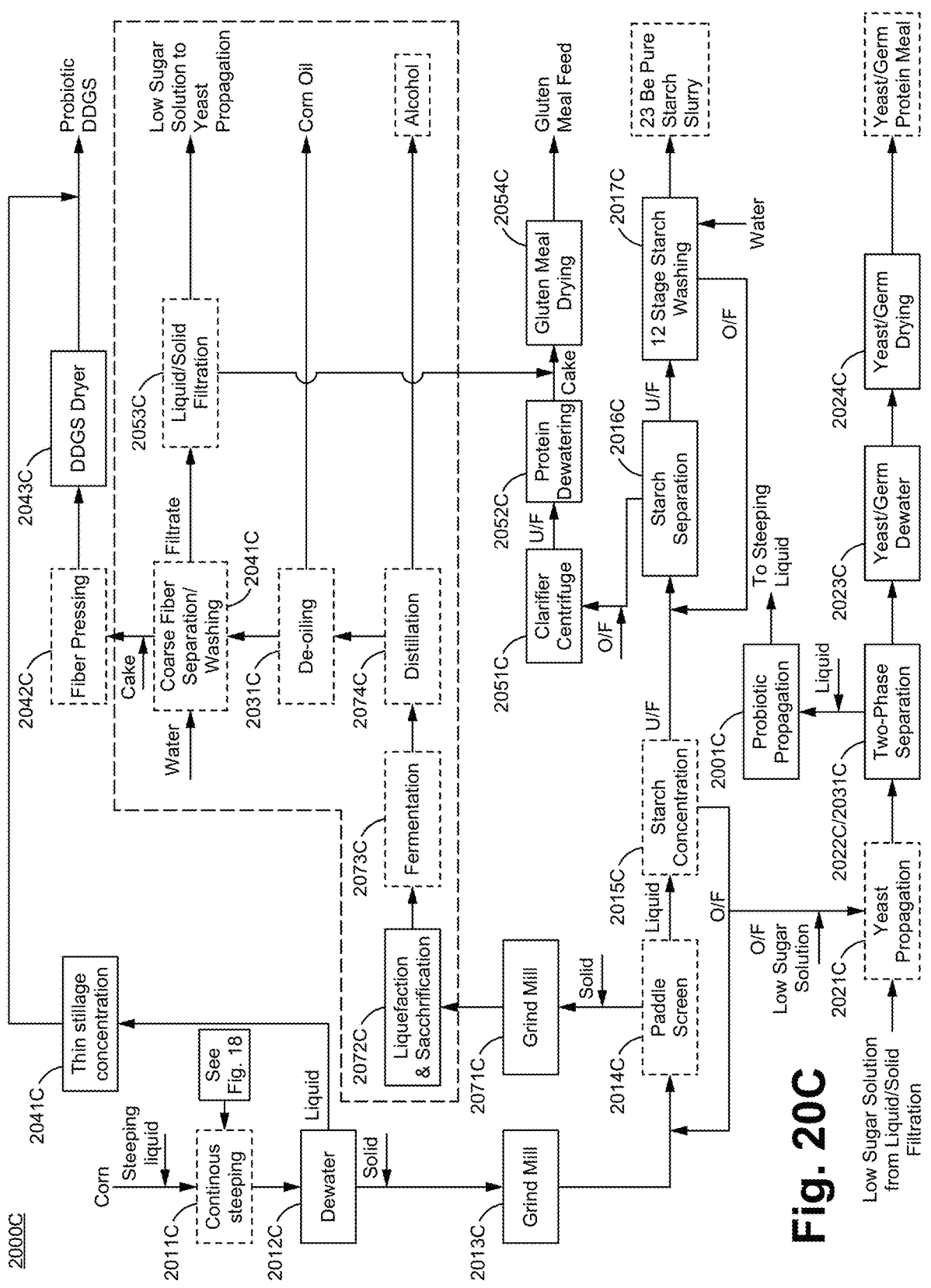
FIG. 20C illustrates a wet mill process that produces pure starch, alcohol, gluten meal feed, and yeast/germ protein meal in accordance with some embodiments.

FIG. 20C illustrates a wet mill process 2000C producing pure starch, yeast/germ protein meal and alcohol in accordance with some embodiments. This variation builds on the significant features in FIG. 20A and also produces alcohol (ethanol) from all the starch bound with protein and fiber in the horny endosperm (instead of the sugar solution in the FIG. 20B). In the following, the key variation processes are illustrated.

At Step 2073C of fermentation, after the starch from the horny endosperm has been liquefied and saccharified, yeast is added. The yeast ferments the sugar solution into alcohol.

At Step 2074C of distillation, a distillation tower or other method of distillation collects the alcohol. The alcohol breaks the oil emulsion. The remaining oil and fiber is separated and directed to deoiling (Step 2031C) and the coarse fiber separation/washing (Step 2041C).

At Step 2031C of Deoiling, the fiber is separated from the corn oil.

At Step 2053C of liquid/solid filtration, the filtrate from the coarse fiber separation/washing (Step 2041C) is filtered. The resulting liquid, a low sugar solution, is combined with the overflow from starch concentration (Step 2015C) and directed to the yeast propagation step in the yeast/germ protein meal process. The resulting solid is combined with the cake from the protein dewatering (Step 2052C) into the gluten meal dryer (Step 2054C).

For succinctness, the rest of Steps that are already provided in the figure are not further described and are able to be performed using ordinary processes or the process described in 1900A.

Figure 20D:
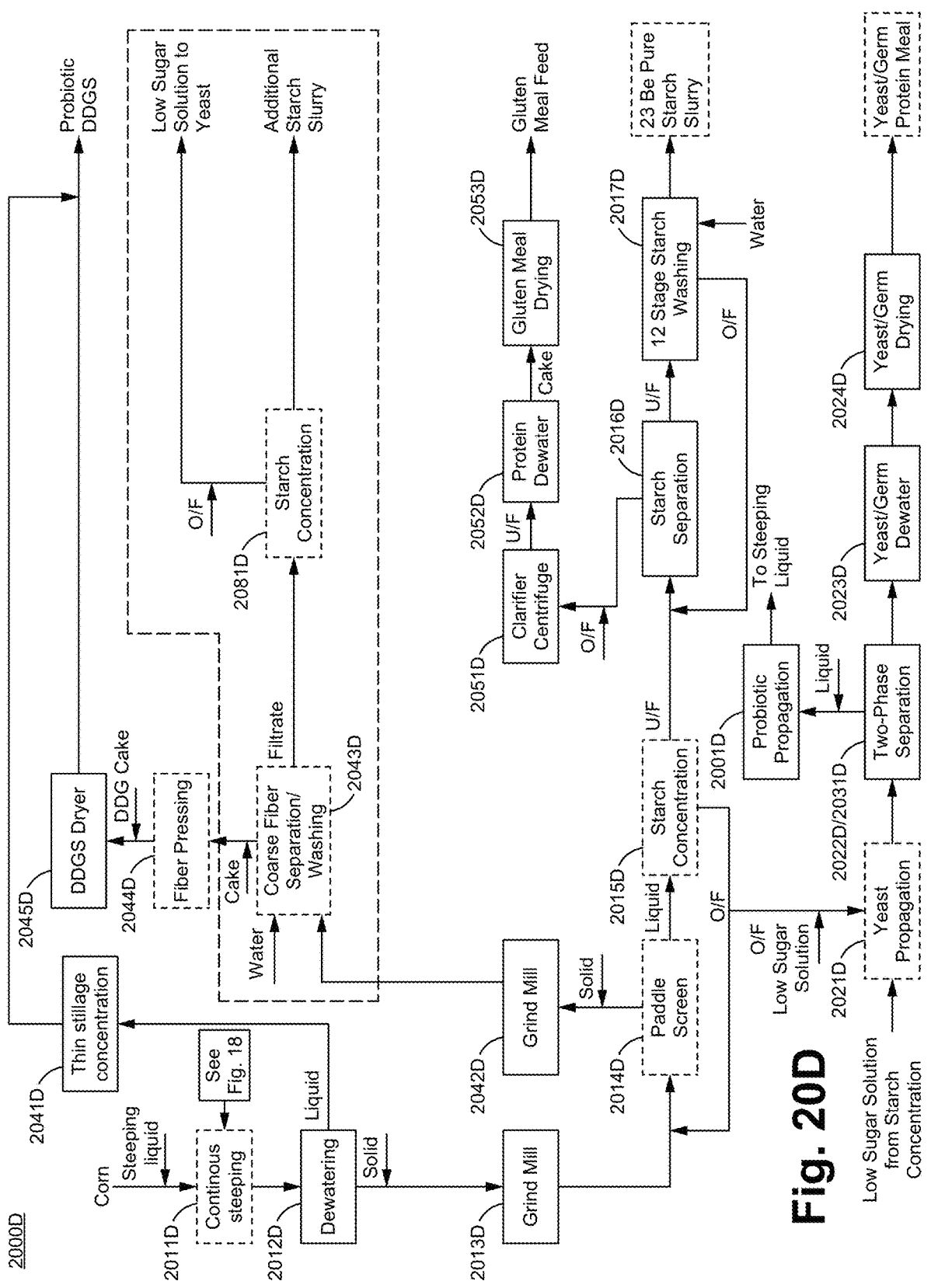
FIG. 20D illustrates a wet mill process that produces additional pure starch, gluten meal feed, and yeast/germ protein meal in accordance with some embodiments.

FIG. 20D illustrates a wet mill process 2000D producing pure starch, yeast/germ protein meal, and additional starch in accordance with some embodiments. This variation builds on the significant changes in FIG. 20A and also produces a 40% starch slurry from the starch bound with protein and fiber in the horny endosperm (instead of the sugar solution in FIG. 20B or alcohol in FIG. 20C). In the following, the key variation processes are illustrated.

After the $2^{nd}$ milling with the LeeTech's Grind Mill in Step 2042D, the slurry goes directly to the coarse fiber separation & washing (Step 2043D) instead of going through liquefaction, saccharification and fermentation first.

At Step 2081D of starch concentration, after coarse fiber separation & washing (Step 2043D), the filtrate is directed into a cyclone concentrator, which produces another starch slurry. The overflow which contains protein and water is a low sugar solution that can be contributed to the yeast propagation step (2021D) in the yeast/germ protein meal process.

For succinctness, the rest of Steps that are already provided in the figure are not further described and are able to be performed using ordinary processes or the process described in 1900A.

Figure 20E:
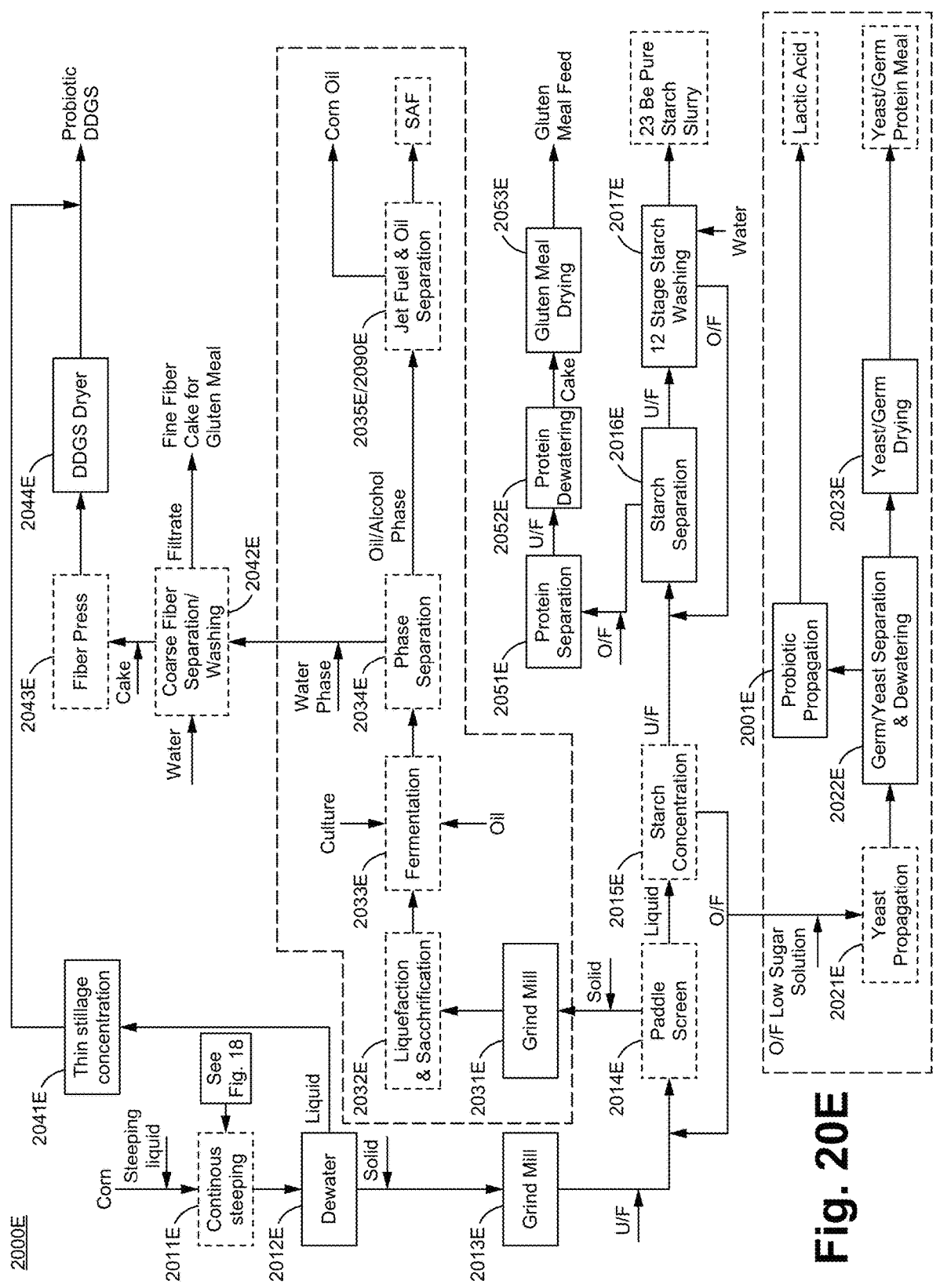
FIG. 20E illustrates a wet mill process that produces pure starch, sustainable aviation fuel (SAF, such as butanol or other alcohol), gluten meal, lactic acid, and yeast/germ protein meal in accordance with some embodiments.

FIG. 20E illustrates a wet mill process 2000E producing pure starch, yeast/germ protein meal, lactic acid, and an alcohol suitable for use as a sustainable aviation fuel (SAF) in accordance with some embodiments. This variation builds on the significant changes in 20A and also converts the sugar solution from all the starch bound with protein and fiber in the horny endosperm into a bio-based alcohol that can be used as sustainable aviation fuel, through fermentation and phase separation. In the following, the key variation processes that are different from the process of 2000D of FIG. 20D are illustrated.

At Step 2032E of liquefaction & saccharification, after the horny endosperm has been milled in the LeeTech Grind Mill in the $2^{nd}$ milling, the starch is liquefied and saccharified (This step is similar to the process in 2000C of FIG. 20C).

At Step 2033E of fermentation, a culture is added. The culture ferments the sugar solution into an alcohol, such as butanol. (This step is similar to the process in 2000C, although a different culture would be used.) Oil is also added. This oil can be the corn oil from a different part of the process, another vegetable oil, an animal-based oil such as tallow, or a petroleum-based oil.

At Step 2034E of phase separation, a separation device such as an incline plate gravity separates the alcohol for sustainable aviation fuel (e.g., butanol) from the water, which stays in the fermenter. The butanol, with 4 carbons, does not dissolve in water so stays with the oil.

At Step 2001E after the probiotic propagation step, the resulting lactic acid can become a co-product itself, usable as a non-toxic, bio-based insecticide.

For succinctness, the rest of Steps that are already provided in the figure are not further described and are able to be performed using ordinary processes or the process described in 1900A.

Figure 21A:
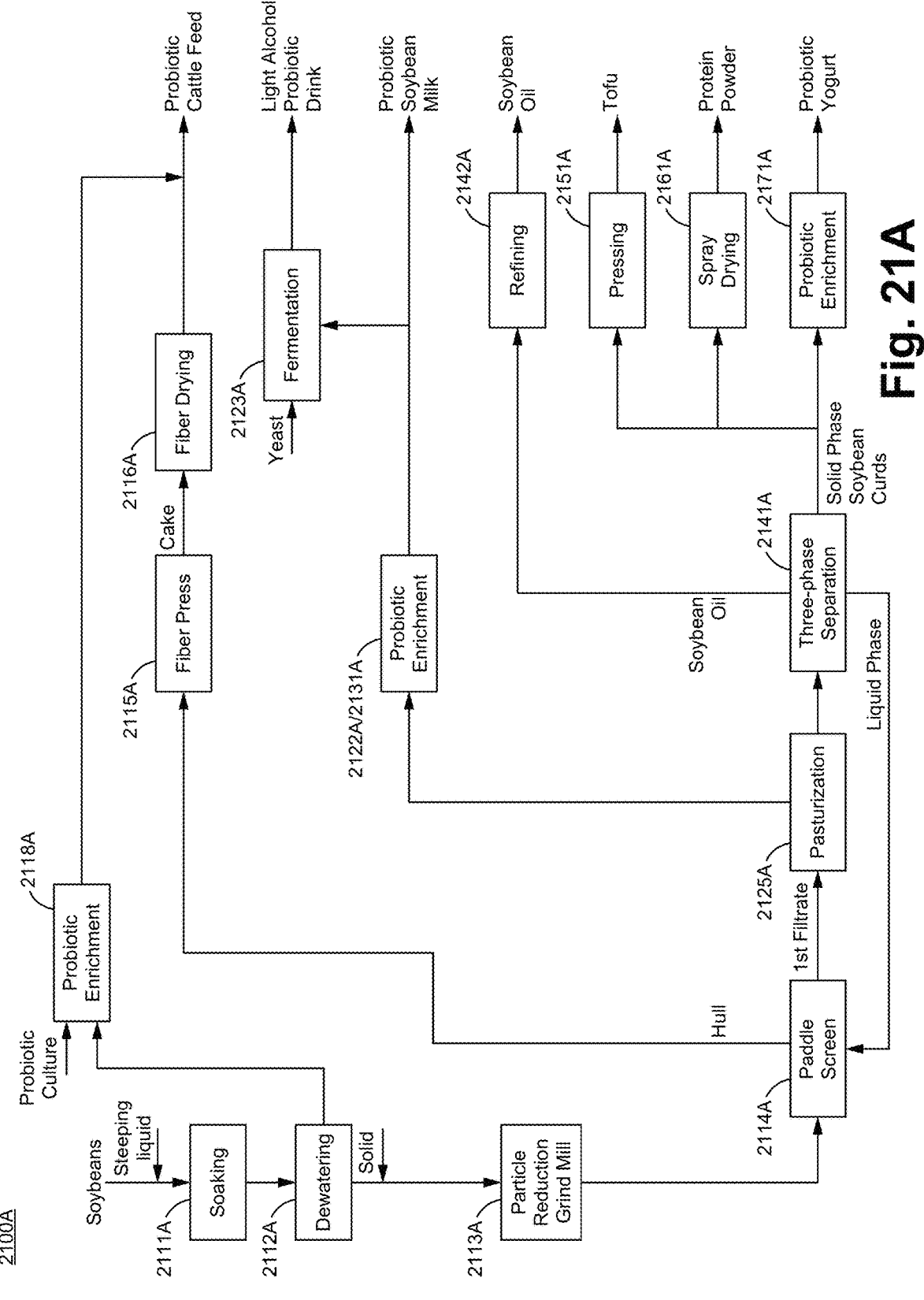
FIG. 21A illustrates a soybean process to produce probiotic food for human consumption in accordance with some embodiments.

FIG. 21A illustrates a soybean process 2100A producing probiotic food products for human consumption in accordance with some embodiments. This variation uses a similar process to what is described above to significantly improve upon the current process for extracting soybean oil from soybeans. This soybean process avoids using the carcinogenic solvent hexane, maintains the protein structure for greater digestibility and creates options for producing a variety of probiotic foods safe for human consumption. In the following, the key variation processes are illustrated.

At Step 2111A, soybeans enter the process and are soaked in either a batch or continuous steeping process.

At Step 2112A of dewatering, free water is separated from the swollen soybeans.

At Step 2113A of a grind mill for a $1^{st}$ milling, a grind mill or other milling device reduces the soybeans into smaller particles (less than 35 microns). LeeTech's patented solid ring design grind mill (U.S. Pat. No. 9,352,326) is suitable for this step, as it enables greater control over the level of grind, and is incorporated by reference for all purposes.

At Step 2114A of a Paddle Screen for liquid/solid separation, a paddle screen or other separation device separates the mixture (which contains protein, fiber and water) into two streams: one with liquid, protein and starch, and the other fiber from the soybean hull with 80% moisture (and no starch). LeeTech's patented paddle screen (U.S. Pat. No. 9,718,006) would be ideal for this step, and is incorporated by reference for all purposes.

At Step 2115A of fiber pressing, a fiber press reduces moisture in the cake from 80% to 60% moisture.

At Step 2116A of DDGS drying, a dryer further dries the cake.

At Step 2117A of probiotic enrichment, water from the dewatering (Step 2112A) is combined with a probiotic culture and added to the cake to produce a probiotic DDGS for cattle feed.

At Step 2121A of pasteurization, the filtrate from the paddle screen (step 2114A) is pasteurized.

At Step 2122A/2131A of probiotic enrichment, a probiotic culture is added to produce probiotic soymilk.

At Step 2123A of fermentation, yeast can be added to the mixture and fermented to create a slightly alcoholic probiotic drink.

At Step 2141A of three-phase separation, after pasteurization, a three-phase decanter or other separation device separates the mixture into an oil phase, solid phase and liquid phase. The liquid can be diverted back to the paddle screen (Step 2114A).

At Step 2142A of oil refining, the oil phase from three phase separation is further refined to create hexane-free soybean oil.

At Step 2151A of tofu pressing, the solid phase from three phase separation (Step 2141A), which is comprised mainly of soybean curds, is pressed to make tofu.

At Step 2161A of spray drying, a spray dryer can also convert the solid phase from three phase separation (Step 2141A) into a soy-based powder as a shelf-stable protein-rich ingredient for smoothies.

At Step 2171A of probiotic enrichment, the solid phase from three phase separation (Step 2141A) can be combined with a culture to make a probiotic non-dairy yogurt.

Abbreviations

The meanings for the abbreviations can be used throughout or selected portion of the Specification or drawings.

U/F—under flow; O/F—over flow.

Features and advantageous aspects of the processes disclosed herein include: (1) using a continual steeping tank design (FIG. 18) to provide a less energy-intensive approach over the current batch operation typically used in U.S. corn wet mills, (2) decreasing steeping time from 50 to 30 hours because of the increased lactic acid concentration in the steeping liquid, (3) increasing efficiency of production by separating and processing separately the easy-to-access starch in the flour endosperm from the harder-to-access starch in the horny endosperm, (4) creating an additional higher value co-product that includes yeast and germ protein that can be used as feed for aquaculture, (5) creating a pure sugar solution that can be used as feedstock for synthetic biology or other bio-based processes, (6) creating a more efficient process to turn starch into ethanol, (7) avoiding using solvent extraction of germ, thereby preventing the solvent toxicity problem and maintaining digestible protein (not denatured) so that the germ protein can be used in aquaculture feed, (8) using less energy over the traditional wet mill process to produce more valuable co-products, (9)

requiring less capital investment over the traditional wet mill process to produce more valuable co-products, (10) producing starch and sugar with higher purity and therefore better as a carbohydrate feedstock for biochemical, synthetic biology, renewal chemical and other green technology processes, (11) producing a syrup with high lactic acid that can used as a natural insecticide, and (12) producing alcohol which can be used to break an oil/protein emulsion.

In operation, a continuous steeping is performed, corn kernels and their parts are milled twice, liquifying and saccharifying are performed, starch in the different part of the corn are separated for different purposes with different processes, and co-products are generated including starch, sugar, animal feed, oil, ethanol and other alcohols such as butanol.

In utilization, pure starch is used in a biotech process as a raw material. When the starch slurry contains less than 0.2% soluble protein, it is a better feedstock for biochemical, synthetic biology, renewable chemical and other green technology processes.

What is claimed is:

1. A continuous steeping tank comprising:
a) a tank body;
b) multiple internal chambers inside the tank body; and
c) one or more paddles in each of the multiple internal chambers configured to move grains progressively through and between chambers; and
d) a steeping liquid inlet coupling with the tank body.

2. The continuous steeping tank of claim 1, wherein the one or more paddles move the grains outwards.

3. The continuous steeping tank of claim 1, wherein the one or more paddles move the grains in different directions in alternating pattern in each of the multiple internal chambers.

4. The continuous steeping tank of claim 1, wherein the one or more paddles comprises 4-8 paddles.

5. The continuous steeping tank of claim 4, wherein the 4-8 paddles are controlled by a variable speed motor connected to a central shaft.

6. The continuous steeping tank of claim 1, wherein the multiple internal chambers comprise 6-12 internal chambers.

7. The continuous steeping tank of claim 1, wherein the steeping liquid inlet is at a bottom of the tank body configured to have a steeping liquid flowing in from the bottom of the tank in a countercurrent flow containing multiple probiotic microorganisms in a predetermined concentration to reduce steeping time.

8. A continuous steeping tank comprising:
a) a tank body;
b) multiple internal chambers inside the tank body; and
c) a plurality of paddles, wherein at least one of the plurality of paddles is positioned in each of the multiple internal chambers configured to move grains progressively through and between chambers; and
d) a steeping liquid inlet coupling with the tank body.

9. The continuous steeping tank of claim 8, wherein the plurality of paddles move the grains outwards.

10. The continuous steeping tank of claim 8, wherein the plurality of paddles move the grains in different directions in alternating pattern in each of the multiple internal chambers.

11. The continuous steeping tank of claim 8, wherein the plurality of paddles comprises 4-8 paddles.

12. The continuous steeping tank of claim 11, wherein the 4-8 paddles are controlled by a variable speed motor connected to a central shaft.

13. The continuous steeping tank of claim 8, wherein the multiple internal chambers comprise 6-12 internal chambers.

14. The continuous steeping tank of claim 8, wherein the steeping liquid inlet is at a bottom of the tank body configured to have a steeping liquid flowing in from the bottom of the tank in a countercurrent flow containing multiple probiotic microorganisms in a predetermined concentration to reduce steeping time.

15. A continuous steeping tank comprising:
e) a tank body;
f) multiple internal chambers inside the tank body; and
g) a plurality of paddles, wherein at least one of the plurality of paddles is positioned in each of the multiple internal chambers configured to move grains progressively through and between chambers; and
h) a steeping liquid inlet coupling with the tank body, wherein the steeping liquid inlet is at a bottom of the tank body configured to have a steeping liquid flowing in from the bottom of the tank in a countercurrent flow containing multiple probiotic microorganisms in a predetermined concentration to reduce steeping time.

16. The continuous steeping tank of claim 15, wherein the plurality of paddles move the grains outwards.

17. The continuous steeping tank of claim 15, wherein the plurality of paddles move the grains in different directions in alternating pattern in each of the multiple internal chambers.

18. The continuous steeping tank of claim 15, wherein the plurality of paddles comprises 4-8 paddles.

19. The continuous steeping tank of claim 18, wherein the 4-8 paddles are controlled by a variable speed motor connected to a central shaft.

* * * * *